(12) United States Patent
Johnson et al.

(10) Patent No.: US 11,867,660 B2
(45) Date of Patent: Jan. 9, 2024

(54) ELECTRONIC CONTROL OF THE PH OF A SOLUTION CLOSE TO AN ELECTRODE SURFACE

(71) Applicant: Robert Bosch GmbH, Stuttgart (DE)

(72) Inventors: Christopher Johnson, San Carlos, CA (US); Sam Kavusi, Menlo Park, CA (US); Nadezda Fomina, Redwood City, CA (US); Habib Ahmad, Sunnyvale, CA (US); Autumn Maruniak, Sunnyvale, CA (US); Christoph Lang, Sunnyvale, CA (US); Ashwin Raghunathan, San Francisco, CA (US); Young Shik Shin, Mountain View, CA (US); Armin Darvish, Brisbane, CA (US); Efthymios Papageorgiou, San Jose, CA (US)

(73) Assignee: ROBERT BOSCH GMBH, Stuttgart (DE)

( * ) Notice: Subject to any disclaimer, the term of this patent is extended or adjusted under 35 U.S.C. 154(b) by 770 days.

(21) Appl. No.: 16/932,096

(22) Filed: Jul. 17, 2020

(65) Prior Publication Data

US 2020/0363371 A1  Nov. 19, 2020

Related U.S. Application Data

(60) Continuation-in-part of application No. 16/227,466, filed on Dec. 20, 2018, now Pat. No. 11,561,198.
(Continued)

(51) Int. Cl.
*G01N 27/416* (2006.01)
*C12Q 1/00* (2006.01)
(Continued)

(52) U.S. Cl.
CPC ......... *G01N 27/4167* (2013.01); *C12Q 1/001* (2013.01); *G01N 27/302* (2013.01);
(Continued)

(58) Field of Classification Search
CPC .. G01N 27/4167; G01N 27/302; G01N 27/34; G01N 27/36; C12Q 1/001; G05D 21/02
See application file for complete search history.

(56) References Cited

U.S. PATENT DOCUMENTS 4,360,415 A * 11/1982 Brezinski ........... G01N 27/4035
204/406
5,063,081 A * 11/1991 Cozzette ............. G01N 35/0099
435/7.1
(Continued)

FOREIGN PATENT DOCUMENTS

CN       1098502     2/1995
CN     102023181     4/2011
(Continued)

OTHER PUBLICATIONS

G.A. S. Minero et al, Electronic pH switching of DNA triplex reactions, RSC Adv., vol. 5 pp. 27313-27325 (2015).
(Continued)

*Primary Examiner* — Alexander S Noguerola
(74) *Attorney, Agent, or Firm* — NORTON ROSE FULBRIGHT US LLP; Gerard A. Messina

(57) ABSTRACT

Device and methods for controlling pH or ionic gradient comprising a multisite array of feedback electrode sets comprising electrodes and pH sensing elements. The electrodes can include a reference electrode, counter electrode, and a working electrode. The device and methods iteratively select an amount of current and/or voltage to be applied to each working electrode, apply the selected amount of current and/or voltage to each working electrode to change pH of a
(Continued)

solution close to the working electrode, and measure the signal output of the sensing element. The multisite array can include feedback and non-feedback electrode sets.

20 Claims, 57 Drawing Sheets

Related U.S. Application Data which is a division of application No. 14/792,576, filed on Jul. 6, 2015, now Pat. No. 10,379,080.

(51) Int. Cl.
| | |
|---|---|
| *G05D 21/02* | (2006.01) |
| *G01N 27/34* | (2006.01) |
| *G01N 27/30* | (2006.01) |
| *G01N 27/36* | (2006.01) |

(52) U.S. Cl.
CPC ............. *G01N 27/34* (2013.01); *G01N 27/36* (2013.01); *G05D 21/02* (2013.01)

(56) References Cited

U.S. PATENT DOCUMENTS

| | | | |
|---|---|---|---|
| 6,618,934 | B1 | 9/2003 | Feldman et al. |
| 6,753,312 | B2 | 6/2004 | Yatcilla et al. |
| 6,797,152 | B2 * | 9/2004 | Freund .................. G01N 21/78 |
| | | | 205/792 |
| 6,887,714 | B2 | 5/2005 | Fritsch et al. |
| 6,976,982 | B2 | 12/2005 | Santini, Jr. et al. |
| 7,195,913 | B2 | 3/2007 | Guire et al. |
| 7,785,785 | B2 | 8/2010 | Pourmand et al. |
| 8,097,134 | B2 * | 1/2012 | Li ...................... G01N 27/3276 |
| | | | 204/267 |
| 8,436,621 | B2 | 5/2013 | Lee et al. |
| 8,552,730 | B2 | 10/2013 | Chiao et al. |
| 8,648,016 | B2 | 2/2014 | Kavusi et al. |
| 8,906,617 | B2 | 12/2014 | Rothberg et al. |
| 8,932,868 | B2 | 1/2015 | Van Grinsven et al. |
| 2003/0228523 | A1 | 12/2003 | Delongchamp et al. |
| 2005/0247559 | A1 * | 11/2005 | Frey .................. G01N 27/3276 |
| | | | 204/403.01 |
| 2007/0138011 | A1 | 6/2007 | Hofmann et al. |
| 2008/0044911 | A1 | 2/2008 | Bock et al. |
| 2008/0305486 | A1 | 12/2008 | Tan et al. |
| 2009/0026082 | A1 | 1/2009 | Rothberg et al. |
| 2009/0061524 | A1 | 3/2009 | Rishpon et al. |
| 2009/0117551 | A1 | 5/2009 | Miho et al. |
| 2009/0205974 | A1 * | 8/2009 | Sivan ................ B01D 15/3885 |
| | | | 205/687 |
| 2010/0105035 | A1 | 4/2010 | Hashsham et al. |
| 2010/0116691 | A1 | 5/2010 | Papadimitrakopoulos et al. |
| 2010/0285601 | A1 | 11/2010 | Kong et al. |
| 2011/0087315 | A1 | 4/2011 | Richardson-Burns et al. |
| 2011/0091870 | A1 | 4/2011 | Lang et al. |
| 2011/0278258 | A1 | 11/2011 | Kavusi et al. |
| 2012/0079897 | A1 * | 4/2012 | Kavusi ............. G01N 33/48707 |
| | | | 73/865.6 |
| 2012/0085660 | A1 | 4/2012 | Rothberg et al. |
| 2012/0115236 | A1 | 5/2012 | Chen et al. |
| 2012/0164351 | A1 | 6/2012 | Gindilis et al. |
| 2012/0222958 | A1 | 9/2012 | Pourmand et al. |
| 2013/0334467 | A1 | 12/2013 | Zhou et al. |
| 2014/0008244 | A1 | 1/2014 | Kavusi et al. |
| 2014/0274760 | A1 | 9/2014 | Fomina et al. |
| 2014/0318958 | A1 | 10/2014 | Hassibi et al. |
| 2014/0370636 | A1 | 12/2014 | Dalton et al. |
| 2017/0010238 | A1 | 1/2017 | Johnson et al. |
| 2019/0134632 | A1 | 5/2019 | Ebejer et al. |

FOREIGN PATENT DOCUMENTS

| | | | |
|---|---|---|---|
| JP | 2005506527 | 3/2005 | |
| JP | 2008241409 | 10/2008 | |
| JP | 20100035555 | 2/2010 | |
| JP | 2011135781 | 7/2011 | |
| WO | 1001011080 A1 | 2/2001 | |
| WO | 2011047020 A1 | 4/2011 | |
| WO | WO 2011082837 A1 * | 7/2011 | ........... G01N 27/333 |
| WO | 2011143188 | 11/2011 | |
| WO | 2014008038 | 1/2012 | |
| WO | 2012076350 A1 | 6/2012 | |
| WO | 2012116385 A1 | 9/2012 | |

OTHER PUBLICATIONS

L. Li et al., Fluorescence from Alexa 488 Fluorophore Immobilized on a Modified gold Electrode, Langmuir, vol. 15., pp. 6358-6363 (1999).

Katsuya, Morimoto et. al.: "Automatic Electrochemical Micro-pH-Stat for Biomicrosystems", Analytical Chemistry, vol. 80, No. 4, Jan. 11, 2008 (Jan. 11, 2008), pp. 905-914.

Chenhao, Ge et. al.: "pH-Sensing Properties of Poly(aniline) Ultrathin Films Self-Assembled on Indium-Tin Oxide", Analytical Chemistry, vol. 79, No. 4, Jan. 11, 2007 (Jan. 11, 2007), pp. 1401-1410.

Wang et. al.: "An electrochemical approach to monitor pH change in agar media during plant tissue culture", Biosensors and Bioelectronics, Elsevier BV, NL, vol. 22, No. 11, Mar. 30, 2007 (Mar. 30, 2007), pp. 2718-2723.

Li-Te, Yin et. al.: "Study of indium tin oxide thin film for separative extended gate ISFET" Materials Chemistry and Physics, vol. 70, No. 1, Feb. 13, 2001 (Feb. 13, 2001), pp. 12-16.

International Search Report dated Sep. 27, 2016 of the corresponding International Application PCT/US2016/065249 filed Jun. 30, 2016.

"Simazine" entry obtained from the EXTOXNET Extension Toxicology Network) website http:pmep.cce.cornell.edu/profiles/extoxnet/pyrethrins-ziram/simazine-ext.html, published Sep. 1993.

Amaro et al., "Metabolic Activation of PCBs to Quinones: Reactivity toward Nitrogen and Sulfur Nucleophiled and Influence of Superoxide Dismutase," American Chemical Society, 1996, vol. 9(3), pp. 623-629.

Anderson et al., "A System for Multiplexed Direct Electrical Detection of DNA Synthesis," Sens Actuators B Chem., 2008, 129(1).

Artzy-Schnirman et al., "A Two-State Electronic Antigen and an antibody Selected to Discriminate Between These States," Nano letters, 2008, vol. No. 10, pp. 3398-3403.

Bazin, Damien et al., "Electrodesposition of Polymer Nanodots with Controlled Density and Their Reversible Functions by Polyhistidine-Tag Proteins," Langmuir, vol. 28, No. 39, Oct. 2, 2012, pp. 13968-13975.

Bizzarri et al., "Green Fluorescent Protein Based pH Indicators for in Vivo Use: A Review," Anal. Bioanal. Chem., 2009, p. 393, pp. 1107-1122.

Cannan et al., "Three-dimensional imaging of proton gradients at microelectrode surfaces using confocal laser scanning miscroscopy," Electrochemistry Communications 4 (2002), pp. 886-892.

Chambers, J.Q., "Elecrochemistry of quinones," The Chemistry of the Quinonoid Compounds, Chapter 12, Pt. 2, pp. 719-757.

Chambers, J.Q., "Elecrochemistry of quinones," The Chemistry of the Quinonoid Compounds, Chapter 14, Pt. 2, pp. 737-791.

Chang et al., "Glucose concentration determination based on silica sol-gel encapsulated glucose oxidase optical biosensor arrays," Talanta, Elsevier, Amsterdam, NL, vol. 83, No. 1, Nov. 15, 2010, pp. 61-65.

Choi, JW et al., "Charge trap in self-assembled monolayer of cytochrome b562-green fluorescent protein chimera," Current Applied Physics, North-Holland, Amsterdam, NL, vol. 6, No. 4, Jul. 1, 2006, pp. 760-765.

Crone et al., "GFP-Based Biosensors," Intech, Chapter 1, State of the Art in Biosensors—General Aspects, 2013, pp. 1-34.

(56) References Cited

OTHER PUBLICATIONS

Elsen et al., "Determination of the capacitance of solid-state potentiometric sensors: An electrochemical time-of-flight method method," Analytical Chemistry, vol. 78, No. 18, pp. 6356-6363 (2006).
Evens, D.H., Encyclopedia Electrochem. Elem. 1978, vol. 12, pp. 1-259.
Frasconi et al., "Electrochemically Stimulated pH Changes: A Route to Control Chemical Reactivity," J. Am. Chem. Soc. (2010) 132(6), pp. 2029-2036.
Gao et al., "A DNA biosensor based on a morpholino oligomer coated indium-tin oxide electrode and a cationic redox polymer," The Analyst, col. 134, No. 5, Jan. 1, 2009, p. 952.
Ge et al., "pH-sensing properties of poly(aniline) ultrathin films self-assembled on indium-tin oxide," Analytical Chmistry, vol. 79(4), pp. 1401-1410 (2007).
Hodneland et al., "Biomolecular surfaces that release ligands under electrochemical control," J. Am. Chem Soc., pp. 4235-4236 (2000).
Hotta et al., "In situ monitoring of the H<+> concentration change near an electrode surface through electrolysis using slab optical waveguide pH sensor," Electrochemistry Communications, Elsevier, Amsterdam, NL, vol. 10, No. 9, Sep. 1, 2008, pp. 1351-1354.
Kirk-Othmer Encyclopedia of Chemical Technology, "Hydrogen-Ion Activity," Copyright John Wiley & Sons, Inc., pp. 1-15.
Kirk-Othmer Encyclopedia of Chemical Technology. "Quinones," Copyright John Wiley & Sons, Inc., pp. 1-35.
Korostynska, Olga et al., "Review on State-of-the-art in Polymer Based pH sensors," Sensors, Jan. 1, 2007, pp. 3027-3042. Retrieved from the Internet: URL: <http://www.ncbi.nlm.nih.gov/pmc/articles/PMC3841878/pdf/sensors-07-03027.pdf>.
Kozlovskaja et al., "Response of hydrogen peroxide, ascorbic acid, and paracetamol at a platinum electrode coated with microfilms of polyaniline," Microchimica Acta; An International Journal on Micro and traceanalysis, springer-Verlag, VI, vol. 166, No. 3-4, Jul. 28, 2009, pp. 229-234.
Liu et al., "pH-switchable bioelectratalysis based on layer-by-layer films assembled with glucose oxidase and branched poly(ethyleneimine)," Sensors and Actuators B: Chemical: International Journal Devoted to Research and Development of Physical and Chemical Transducers, Elsevier S.A., Switzerland, vol. 156, No. 2, Feb. 7, 2011, pp. 645-650.
Loomis et al., "Plamt Phenolic Compounds and the Isolation of Plant Enzymes," Phytochemistry, vol. 5, pp. 423-438, (1966).
Maurer, K. et al., "Electrochemically Generated Acid and Its Containment to 100 Micron Reaction areas for the Production of DNA Microarrays," PLOS One 2006, Issue 1, e34, pp. 1-7.
Mu et al., "Catechol sensors using poly(aniline-co-o-aminophenol) as an electron transfer mediator," Biosensors and Bioelectronics, Elsevier BV, NL, vol. 21, No. 7, Jan. 15, 2006, pp. 1237-1243.
Oshige, Masahiko et al., "Immobilization of His-Tagged Proteins on Various Solid Surfaces Using NTA-Modified Chitosan," Open Journal of Polymer Chemistry, Feb. 1, 2013, pp. 3, 6-10.
Borgmann et al., Amperometric Biosensors, Advances in Elecrochemical Science and Engineering, 2011, pp. 1-84.
Turner, "Biosensors: Sense and Sensibility," Chem Soc Rev, 2013, 42(8), pp. 3125-3638.
Yotter et al., Sensor technologies For Monitoring Activity in Single Cells—Part I: Optical Methods, IEEE Sensors Journal, 2004, 4(4), pp. 395-411.
Bocharova et al., "Reversible gating contorlled by enzymes at nanostructured interface," Chemical Communications—CHEMCOM., vol. 46, No. 12, Jan. 1, 2010, pp. 645-650.
Tam et al., "Biochemically Controlled Bioelectrocatalytic Interface," Journal of the American Chemical Society,vol. 130,No. 33, Aug. 1, 2008, pp. 10888-10889.
Quan et al., "Voltammetry of Quinones in Unbuffered Aqueonus Solution: reassessing the roles of proton transfer and hydrogen bonding in the aqueous electrochemistry of quinones," J. Am. Chem. Soc. 129(42), pp. 12847-12856 (2007).
Ribereau-Gayon et al., "The Microbiology of Wine and Vinifications," Handbook of Enology, vol. 1, 2nd ed. John Wiley Sons, Ltd. 2006, p. 234.
Slowinska et al., "An electrochemical time of-flight technique with galvanostatic generation and potentiometric sensing," Journal of Electroanalytical Chemistry, vol. 554-555, pp. 61-69 (2003).
Steenken, S., "One-Electron-Reduction Potentials of Pyrimidine Bases, Nucleosides, and Nucleotides in Aqueous Solution. Consequences for DNA Redox Chemistry," J. Am. Chem. Soc., 19992, 114:4701-09.
Yin, Li-Te et al., "Study of indium tin oxide thin film for separative extended gate ISFET," Materials Chemistry and Physics, 70(1), pp. 12-16 (2001).
Yin.D.X, et al., "Tetracycline-Controlled Gene Expression System Achieves High-Level and Quantitative Control of Gene Expression," Analytical Biochemistry, 1996, 235: pp. 195-201.
Zeravik et al., "A highly sensitive flow-through amperometric immunosensor based on the Peroxidase chip and enzyme-channeling principle," Biosensors and Bioelectronics, vol. 18 No. 11, Oct. 1, 2003, pp. 1321-1327.
Zhang, J., Protein-Protein Interactions in Salt Solutions, Intech, 2012, pp. 359-377.
International Search Report dated Sep. 17, 2013 of the corresponding International Application PCT/US2013/047563 filed Jun. 25, 2013.
International Search Report dated Jul. 29, 2014 of the corresponding International Application PCT/US2014/026250 filed Mar. 13, 2014.

\* cited by examiner

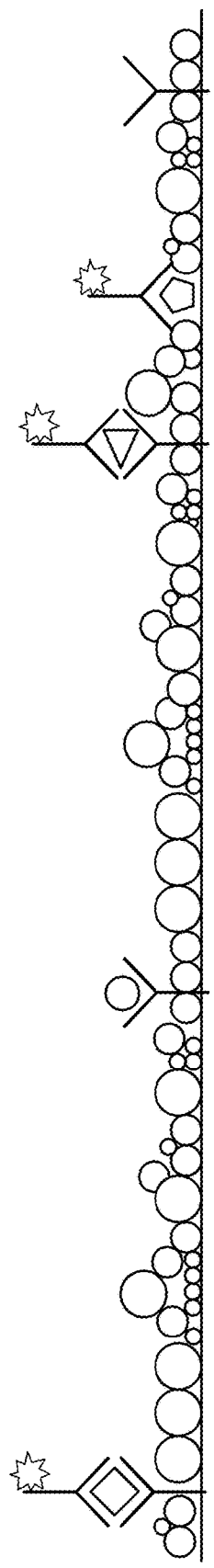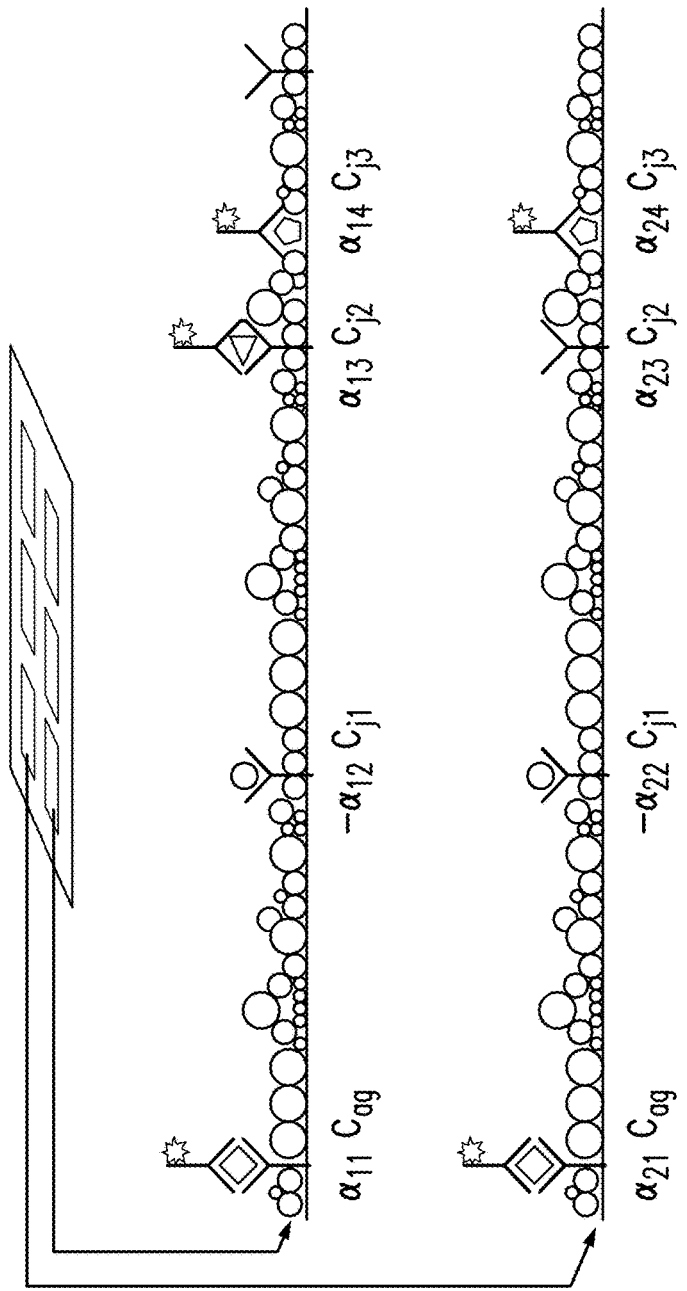

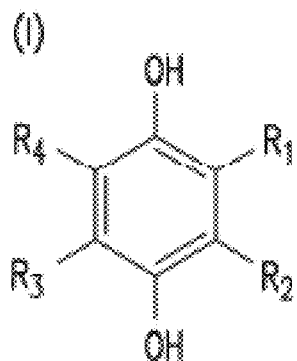
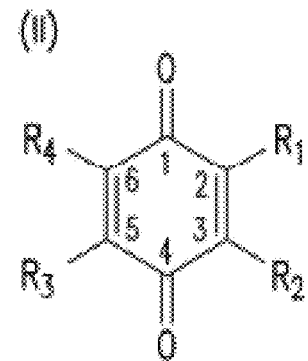
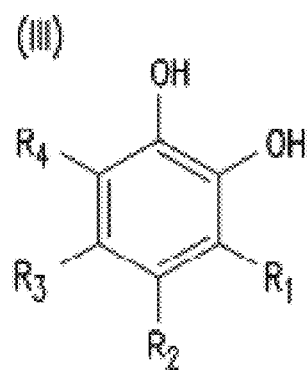
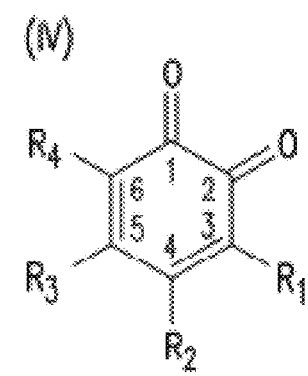
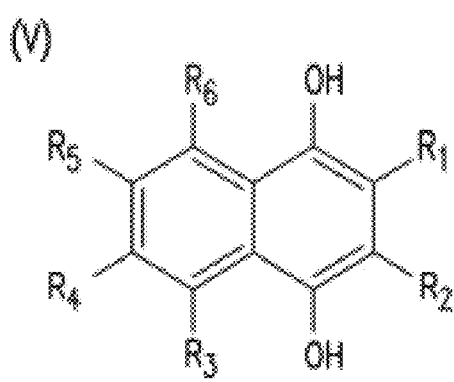
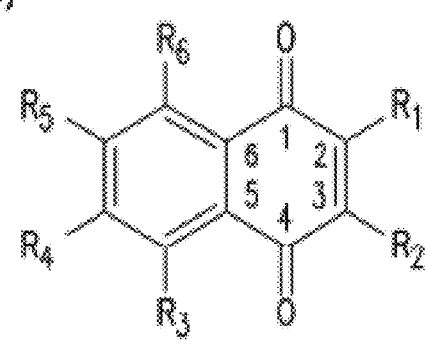
Figure 22

(VII) 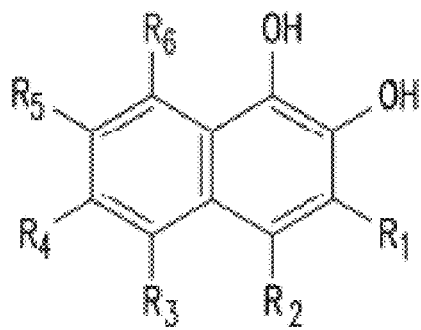
(VIII) 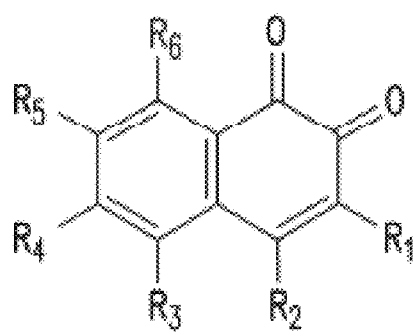
(IX) 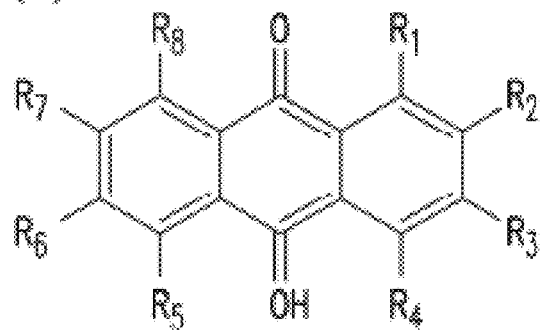
(X) 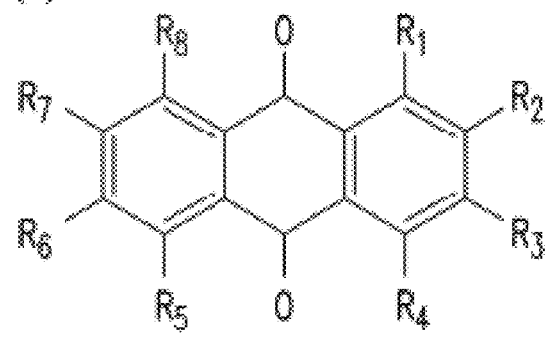
(XI) 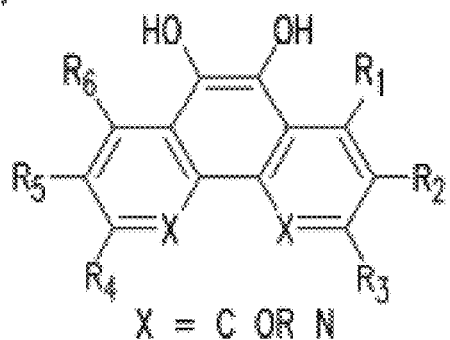
X = C OR N
(XII) 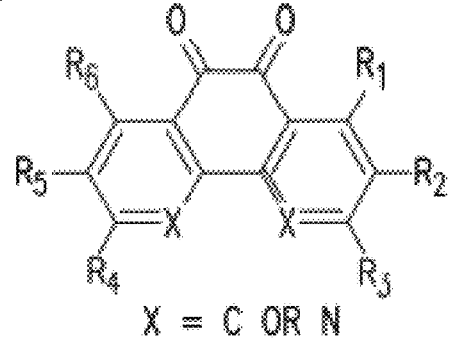
X = C OR N
Figure 22 Continued

$R_1, R_2, R_3, R_4, R_5, R_6, R_7, R_8$: H, $C_xH_{2x+1}$, Cl, F, I, Br, OM, $NO_2$,

OH, $OC_xH_{2x}$, $OC_xH_{2x}OH$, $O(C_xH_{2x}O)_yOH$, $O(C_xH_{2x}O)_yOC_xH_{2x+1}$, $O(C_xH_{2x}O)_yCOOH$, $O(C_xH_{2x}O)_yCOOM$,

COOH, COOM, $COOC_xH_{2x+1}$, $CONHC_xH_{2x+1}$, $CON(C_xH_{2x+1})_2$, $SO_3H$, $SO_3M$, $NH_2$, $NHC_xH_{2x+1}$, $N(C_xH_{2x+1})_2$, $NHC_xH_{2x}OH$, $NHC_xH_{2x}NH_2$, $N(C_xH_{2x}OH)_2$, $N(C_xH_{2x}NH_2)_2$, $NHCOC_xH_{2x+1}$, $NC_xH_{2x+1}COC_xH_{2x+1}$, $NC_xH_{2x+1}COC_xH_{2x}OH$, $NC_xH_{2x+1}COC_xH_{2x}NH_2$, $NC_xH_{2x+1}COC_xH_{2x}SH$, SH, $SC_xH_{2x}$, $SC_xH_{2x}OH$, $S(C_xH_{2x}O)_yOH$, $S(C_xH_{2x}O)_yOC_xH_{2x+1}$, $S(C_xH_{2x}O)_yCOOH$, $S(C_xH_{2x}O)_yCOOM$, $OC_xH_{2x}SH$, $O(C_xH_{2x}O)_ySH$, $O(C_xH_{2x}O)_ySC_xH_{2x+1}$, $C_xH_{2x}$, $C_xH_{2x}OC_xH_{2x}$, $C_xH_{2x}SC_xH_{2x}$, $C_xH_{2x}NHC_xH_{2x}$, $C_xH_{2x}N(C_xH_{2x+1})C_xH_{2x}$ $C_xH_{2x+1}$, $C_xH_{2x+1}OH$, $C_xH_{2x+1}OC_xH_{2x}$, $C_xH_{2x+1}OC_xH_{2x}OH$, $C_xH_{2x+1}O(C_xH_{2x}O)_yOH$, $C_xH_{2x+1}O(C_xH_{2x}O)_yOC_xH_{2x+1}$, $C_xH_{2x+1}O(C_xH_{2x}O)_yCOOH$, $C_xH_{2x+1}O(C_xH_{2x}O)_yCOOM$, $C_xH_{2x+1}COOH$, $C_xH_{2x+1}COOM$, $C_xH_{2x+1}COOC_xH_{2x+1}$, $C_xH_{2x+1}CONHC_xH_{2x+1}$, $C_xH_{2x+1}CON(C_xH_{2x+1})_2$, $C_xH_{2x+1}SO_3H$, $C_xH_{2x+1}SO_3M$, $C_xH_{2x+1}NH_2$, $C_xH_{2x+1}NHC_xH_{2x+1}$, $C_xH_{2x+1}N(C_xH_{2x+1})_2$, $C_xH_{2x+1}NHC_xH_{2x}OH$, $C_xH_{2x+1}NHC_xH_{2x}NH_2$, $C_xH_{2x+1}N(C_xH_{2x}OH)_2$, $C_xH_{2x+1}N(C_xH_{2x}NH_2)_2$, $C_xH_{2x+1}NHCOH_xH_{2x+1}$, $C_xH_{2x+1}NC_xH_{2x+1}COC_xH_{2x+1}$, $C_xH_{2x+1}NC_xH_{2x+1}COC_xH_{2x}OH$, $C_xH_{2x+1}NC_xH_{2x+1}COC_xH_{2x}NH_2$, $C_xH_{2x+1}NC_xH_{2x+1}COC_xH_{2x}SH$, $C_xH_{2x+1}SH$, $C_xH_{2x+1}SC_xH_{2x}$, $C_xH_{2x+1}SC_xH_{2x}OH$, $C_xH_{2x+1}S(C_xH_{2x}O)_yOH$, $C_xH_{2x+1}S(C_xH_{2x}O)_yOC_xH_{2x+1}$, $C_xH_{2x+1}S(C_xH_{2x}O)_yCOOH$, $C_xH_{2x+1}S(C_xH_{2x}O)_yCOOM$ sugars, peptides, aminoacids M: any metal cation or NH4+ x: from 1 to $1*10^9$   y: from 1 to $1*10^9$

Figure 22
Continued

*para*-quinones
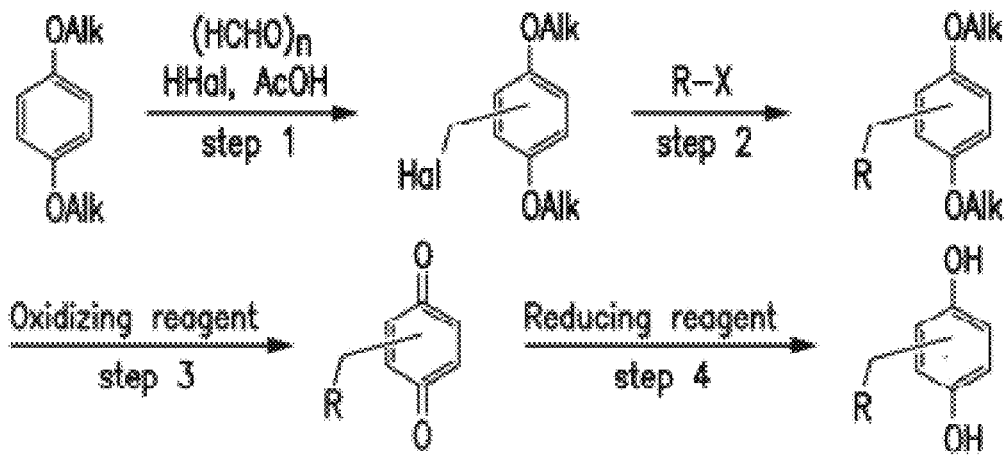
*ortho*-quinones
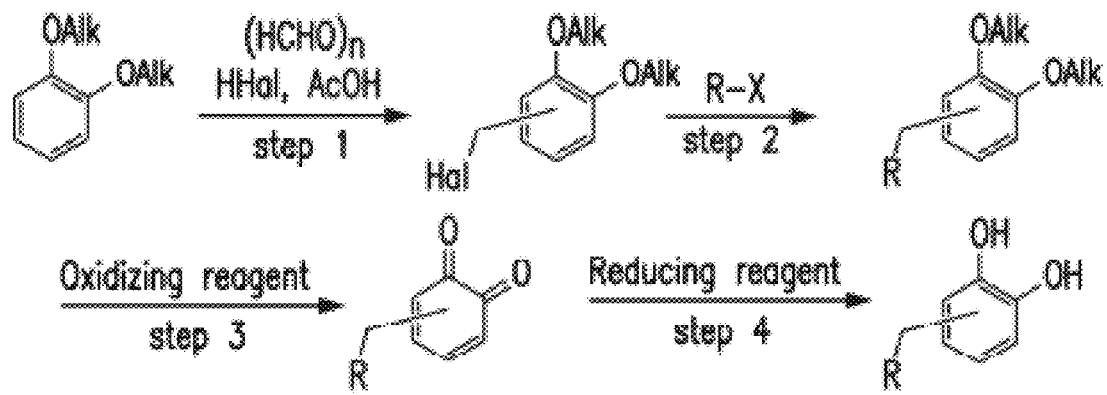
*para*-naphthaquinones
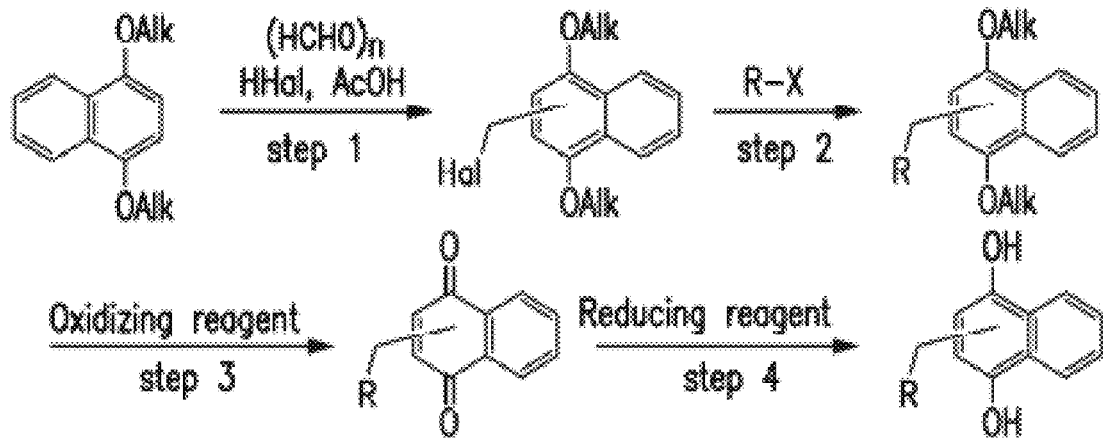
Figure 25

Alk = $C_xH_{2x+1}$
Hal = Cl, Br, or I
R = R1, R2, R3, R4, R5, R6, R7, or R8 in Figure 31
X = OH, $NH_2$, NHR, SH, $O^-$, $S^-$
Oxidizing reagent = $(NH_4)_2Ce(NO_3)_6$, $PhI(OAc)_2$
Reducing reagent = $Na_2S_2O_4$, $KBH_4$, $NaBH_4$, $Cl_3SiH$

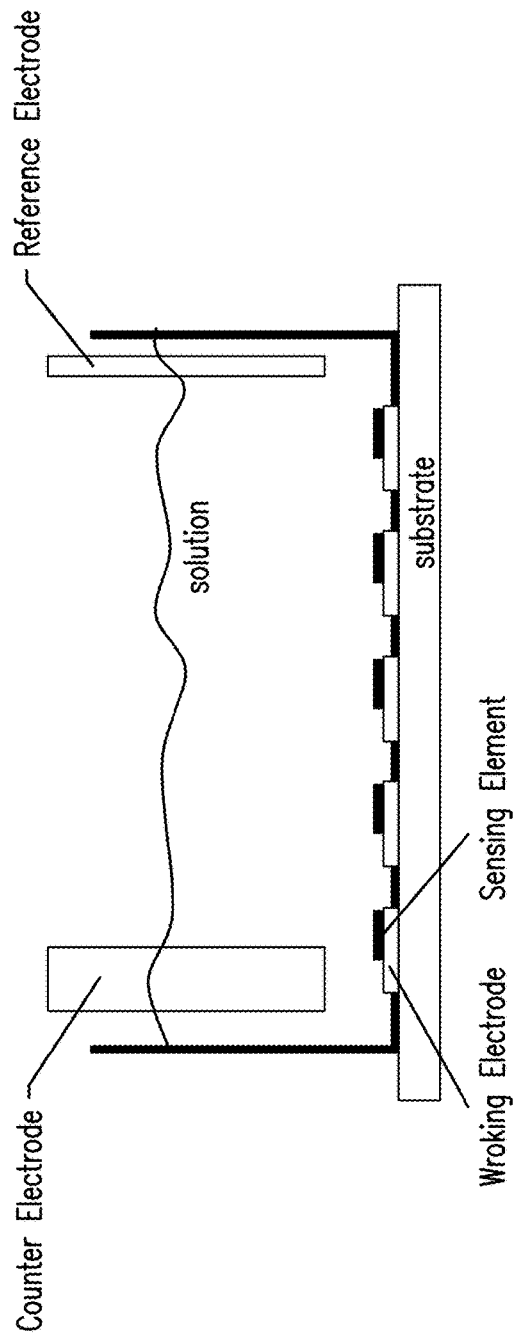
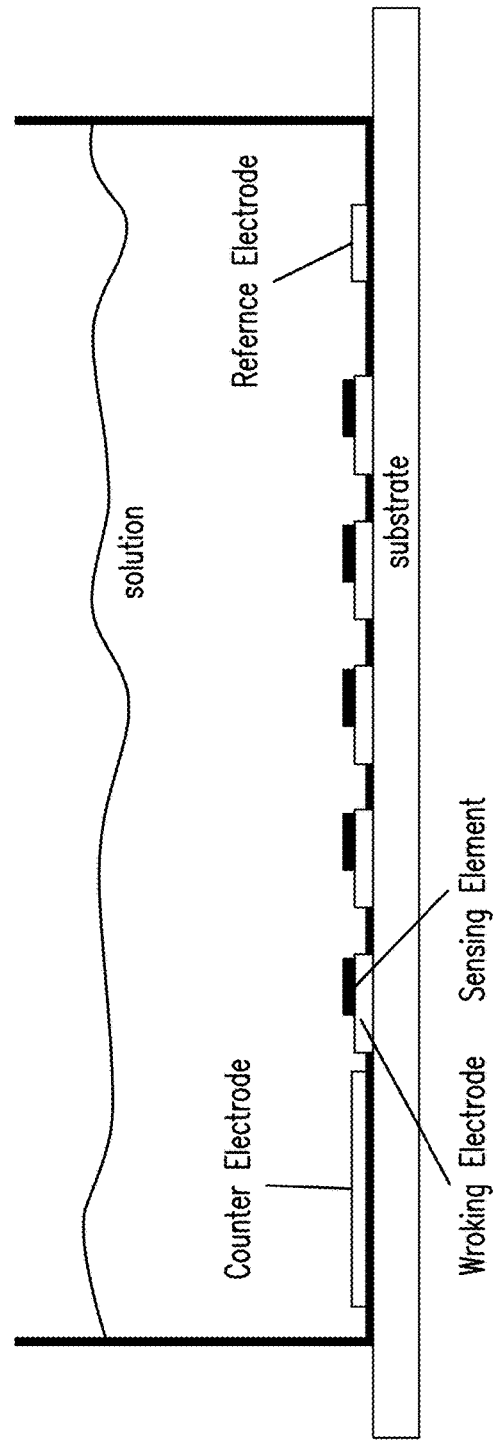
FIG. 54A
FIG. 54B

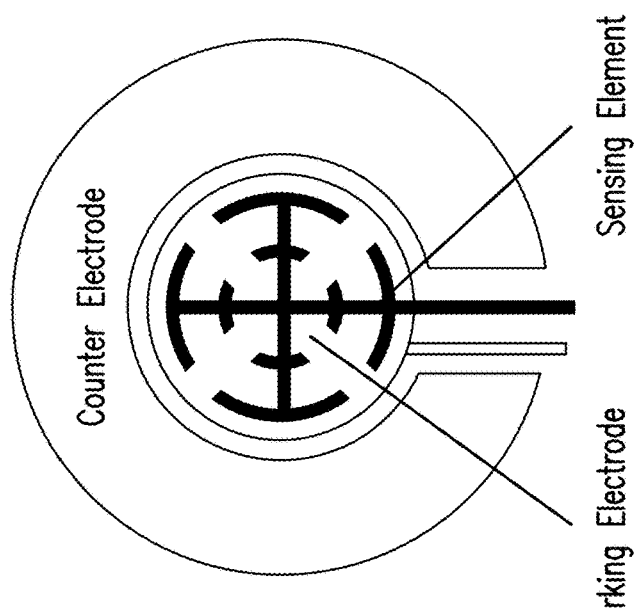
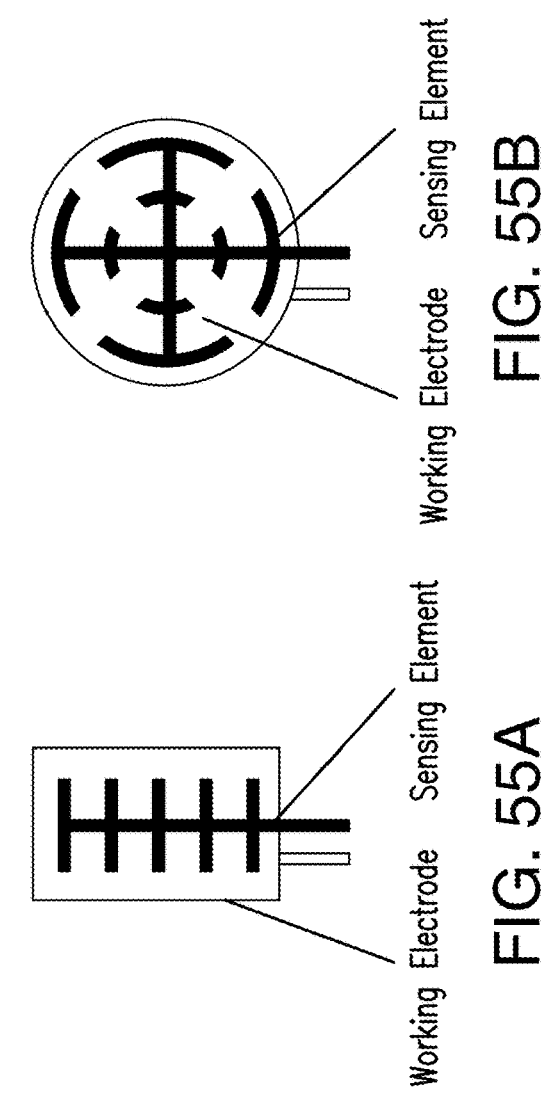
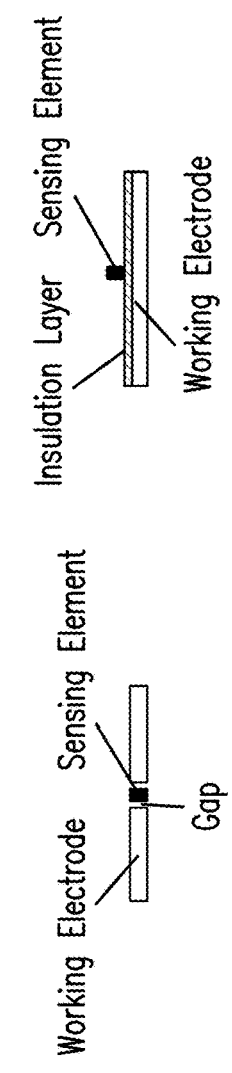
FIG. 55A  FIG. 55B  FIG. 55C  FIG. 55D  FIG. 55E

ELECTRONIC CONTROL OF THE PH OF A SOLUTION CLOSE TO AN ELECTRODE SURFACE

CROSS-REFERENCE TO RELATED APPLICATION

The present application is a continuation-in-part of U.S. patent application Ser. No. 16/227,466, filed Dec. 20, 2018, which is a divisional application of U.S. patent application Ser. No. 14/792,576, filed on Jul. 6, 2015, now U.S. Pat. No. 10,379,080. The entire contents of each of the above-referenced disclosures is hereby incorporated by reference herein without disclaimer.

FIELD OF THE INVENTION

The invention relates to a biosensor device for use in diagnostic methods for biomolecules. The invention also relates to a method and corresponding devices and systems for detecting the presence of bubbles in an aqueous solution; and glass slides for performing life science experiments, in which at least some of the processing of data measured at the slide is performed by a computer processor located on the slide or by a processor on a peripheral component connected to a body of, or wirelessly coupled to the slide. The invention also relates to the use of electrochemical reactions, in particular redox reactions, in a solution to modulate the pH of the solution using electric current. The invention also relates to biological buffers and in particular electrochemically active agents that are compatible for use in biological buffers and are usable to facilitate pH modulation in biological buffers. Moreover, the invention relates to a method for generating a pH concentration gradient near electrode surfaces. The inventions can be used for modulating biomolecular interactions in biosensors, a method for using integrated electronic systems for improving the accuracy, precision, and reliability in controlling a pH gradient near electrode surfaces, methods for controlling the pH in order to modulate biomolecular interactions in such biosensor, a diagnostic method for biomolecules using a biosensor, and methods of improving such biosensor.

BACKGROUND INFORMATION

Recently there has been an increased interest in predictive, preventative, and particularly personalized medicine which requires diagnostic tests with higher fidelity, e.g., sensitivity and specificity. Multiplexed measurement platforms, e.g., protein arrays currently used in research, are among the promising diagnostics technologies for the near future. The samples in these tests can be human body fluids such as blood, serum, saliva, biological cells, urine, or other biomolecules but can also be consumables such as milk, baby food, or water. Within this field there is a growing need for low-cost, multiplexed tests for biomolecules such as nucleic acids, proteins, and also small molecules. Achieving the sensitivity and specificity needed in such tests is not without difficult challenges. Combining these tests with integrated electronics and using Complementary Metal Oxide Semiconductors (CMOS) technology has provided solutions to some of the challenges.

The two main limitations in a detection assay include sensitivity and cross-reactivity. Both of these factors affect the minimum detectable concentration and therefore the diagnostic error rate. The sensitivity in such tests is generally limited by label detection accuracy, association factor of the probe-analyte pair (for example an antibody-antigen pair), and the effective density of probe molecule (for example probe antibody) on the surface (as shown in FIG. 1). Other molecules in the biological sample can also affect the minimum detectable concentration by binding to the probe molecule (for example the primary antibody), or by physisorption of the analyte to the surface at the test site (as shown in FIG. 2). The detection agent (for example a secondary antibody) may also physisorb to the surface causing an increase in the background signal (as shown in FIG. 2). Solving the cross-reactivity and background problem can take a significant amount of time in the assay development of a new test and increases the cost and complexity of the overall test. The assay is typically optimized by finding the best reagents and conditions and also by manufacturing the most specific probe molecule (for example antibody). This results in a long development time, the infeasibility of tests in some cases, and a higher manufacturing cost. For example a typical development of an ELISA assay requires several scientists working for more than a year finding the correct antibody as part of the assay development. Cross-reactivity of the proteins may be the source of the failure of such an effort.

A biosensor providing a multiple site testing platform was thought to provide a solution to some of the above described limitations in assay development. US Published Patent Applications US2011/0091870 and US2012/0115236 (the contents of which are incorporated herein by reference in their entirety) describe such biosensors having multiple sites that could be subjected to different reaction conditions to modulate the binding of the biomolecular analyte (for example proteins) to the probe molecule. For example, the signal detected in a biosensor having four sites also can have several components, e.g. four. These four terms may correspond to the concentration of the biomarker of interest, concentration of interfering analytes in the sample that bind non-specifically to primary antibody (probe molecule) sites and prevent the biomarker to bind, concentration of interfering analytes in the sample that form a sandwich and produce wrong signal, and finally the concentration of interfering analytes in the sample that physisorb to the surface and produce wrong signal. Each term is also proportional to a binding efficiency factor, $\alpha_{ij}$, which is a function of the molecule affinities and other assay conditions, e.g., mass transport. By controlling the condition at each site separately, different sites will have different efficiency factors.

Accurate and precise control of the assay conditions at different sites to generate large changes in the binding efficiency factors is important in the performance of such biosensor as a detection system for a biomolecular analyte of interest. In US2014/0008244 (the content of which is incorporated herein by reference in its entirety) such biosensors and such methods are described that can be readily integrated with a CMOS, electrode array, or TFT based setup to generate large change in binding efficiencies between test sites in a biosensor having an array of multiple test sites. In order to accurately measure the biomolecular analyte of interest the biosensor requires a high degree of reliability and reproducibility. Variations in the modulation of the local pH due to repeated use of the biosensor and variations between subsequent measurements may decrease the accuracy of the determination of the biomolecular analyte of interest by such biosensor.

In addition, pH is a factor that plays an important role for the binding interactions among biomolecules, enzymatic activities, chemical modification such as protection/deprotection of a functional group, chemical/biochemical reaction kinetics, and visualization of pH sensitive reporter molecules. Since pH can serve as a universal switch or a controller for various types of processes, precise control of pH, especially for controlling multiple conditions in parallel, can offer great opportunities in various applications. As such the modulation of the pH at each site of the multisite array of the biosensor needs to be accurately controlled and variations in such pH modulation need to be corrected. Therefore, there is a need for a biosensor in which the pH can be accurately, reliably, and reproducibly controlled at each of the multisite array test sites.

General methods for measuring and controlling pH are known in the art. (Durst et al., "Hydrogen-Ion Activity," Kirk-Othmer Encyclopedia of Chemical Technology, pp. 1-15 (2009)). Currently, the pH of a sample is commonly changed by exchanging the whole buffer solution with the target pH or adding acid or base to the solution. This process is time consuming, prone to error, and, in many cases, induces a significant dilution to the sample. If the sample volume is small or multiple rounds of pH changes during the course of an assay or a reaction are required, currently commercially available technology cannot provide a good solution. Therefore, a technical solution that enables to control pH with flexible temporal and spatial target values and a minimal dilution factor can benefit multiple research and industrial applications.

Active pH control of a solution in contact with an electrode surface has potential applications in protein-protein interactions, isoelectric focusing, electrophoresis, combinatorial pH studies of chemical and biochemical processes, DNA denaturation and renaturation, controlling enzymatic processes, cell manipulations, as a means for accelerating or inhibiting chemical reactions with high spatial and temporal resolution, or in other processes involving pH as a variable. For example, US2014/0008244 describes a biosensor capable of modulating the pH or ionic concentration gradient near electrodes in the biosensor in order to modulate the binding interactions of biological samples of interest. In another example, US2014/0274760 (hereby incorporated by reference in its entirety) describes an improved biosensor with increased accuracy, reliability, and reproducibility.

Attempts to control solution properties through electrochemical agents attached to the surface have been described. Electrochemically triggered release of biotin from a modified gold electrode surface via reduction and subsequent lactonization of quinone tether was demonstrated (Hodneland et al., "Biomolecular surfaces that release ligands under electrochemical control," J. Am. Chem. Soc. 122, pp. 4235-36 (2000)). Electrochemical control of self-assembly and release of antibodies from the surface into solution was achieved by reduction and oxidation of n-decanethiol-benzoquinones (Artzy-Schnirman et al., Nano Lett. 8, pp. 3398-3403 (2008)). Release of protons from a 3D layer of electroactive material was demonstrated by Frasconi et al. using materials composed of gold nanoparticles and thioanilines (Frasconi et al., "Electrochemically Stimulated pH Changes: A Route To Control Chemical Reactivity," J. Am. Chem. Soc. 132(6), pp. 2029-36 (2010)). Electrochemical oxidation of thioaniline groups produced protons that diffused from electrode surface into the surrounding solution, thus altering its pH.

Electrochemical pH modulation in biological solutions presents a significant challenge due to complex nature of the system. The limitations include: presence of buffer components that restrict pH changes, limitations on co-solvents that can be used, presence of strong nucleophiles, such as amines and thiols, and presence of interfering electrochemically active components, such as DNA bases, ascorbic acid and glutathione.

Quinones are one of the most widely studied classes of electrochemically active molecules (See Thomas Finley, "Quinones," Kirk-Othmer Encyclopedia of Chemical Technology, 1-35 (2005), which is incorporated by reference in its entirety. See also, Chambers, J. Q. Chem. Quinonoid Compd. 1974, Pt. 2:737-91; Chambers, J. Q. Chem. Quinonoid Compd. 1988, 2:719-57; Evans, D. H. Encycl. Electrochem. Elem. 1978, 12: 1-259). Hydroquinone/benzoquinone transformation has been used as a model system to produce proton gradients at electrode surface (Cannan et al., Electrochem. Communications 2002, 4:886-92). A combination of para-hydroquinone and anthraquinone was used for generation of acidic pH in organic solution as a first step of DNA synthesis, and organic base was added to the solution in order to confine the acidic pH to electrode surface (Maurer, PLOS One 2006, 1:e34). However, those systems cannot be adopted for use in biological solutions due to reactivity of benzoquinone (the product of hydroquinone oxidation) towards nucleophiles that are often present in biological systems, such as peptides, proteins and glutathione (Amaro et al., Chem Res Toxicol 1996, 9(3):623-629); and further due to the insufficient solubility of unsubstituted anthraquinone in water.

Electrochemical time of flight measurements have demonstrated that $H^+$ ions generated on electrodes will diffuse out (Slowinska et al., "An electrochemical time-of-flight technique with galvanostatic generation and potentiometric sensing," J. Electroanal. Chem. Vol. 554-555, pp. 61-69 (2003); Eisen et al., "Determination of the capacitance of solid-state potentiometric sensors: An electrochemical time-of-flight method," Anal. Chem. 78(18), pp. 6356-63 (2006)). It has also been shown that the open circuit potential of an electrode surface is a function of the ionic concentration in a solution, including the $H^+$ concentration in the solution, and therefore of the pH of the solution (Yin et al., "Study of indium tin oxide thin film for separative extended gate ISFT," Mat. Chem. Phys. 70(1), pp. 12-16 (2001)). Similarly, the redox reaction rates of electrochemical species are also pH dependent (Quan et al., "Voltammetry of quinones in unbuffered aqueous solution: reassessing the roles of proton transfer and hydrogen bonding in the aqueous electrochemistry of quinones," J. Am. Chem. Soc. 129(42), pp. 12847-56 (2007)). There has also been work done on improving the pH sensitivity of an electrode by incorporation of novel pH sensitive coatings to improve the accuracy of pH sensing (Ge et al., "pH-sensing properties of poly (aniline) ultrathin films self-assembled on indium-tin oxide," Anal. Chem. 79(4), pp. 1401-10 (2007)).

Many life science applications (proteomics, genomics, microfluidics, cell culture, etc.) use glass slides as a substrate for performing experiments. Examples of glass slides include protein microarrays, lysate arrays, DNA microarrays and cell culture platforms. One use of a protein microarray is to analyze biological substances (e.g., blood serum) from patients with a specific disease in comparison to corresponding substances from healthy or control subjects. The biological substances are applied to a microarray containing many (often thousands of) human proteins. Antibodies in diseased substances may react (bind) with certain antigens in the microarray, thereby identifying the antigens as disease-specific biomarkers. In addition to protein detection, other types of detection such as colorimetric, chemiluminescence and fluorescence detection are also possible with glass slides.

Often the experiments are performed under aqueous conditions, in which a substance-of-interest is combined with water or a water-containing liquid and placed onto a slide for analysis. In many cases the presence of bubbles (formed of air or other gases) disturbs the experiment, adversely affecting the results. One example of an adverse effect is when a bubble causes the test solution to dry out. This can create a false binding event where the substance-of-interest (e.g., a biomolecular analyte) fails to bind with a molecule with which the biomolecular analyte is supposed to interact. Another example is where the bubbles change the effective flow rate of the test solution and the flow rate is being measured as part of the experiment. Therefore, it is desirable to detect bubbles and to output an indication of their presence, so that experiment results can be interpreted correctly.

One way to detect bubbles is to manually check each slide under a microscope. However, microscopy is not always practical because the field of view is typically limited to a small area of the slide, so that checking the entire slide is time-consuming. Additionally, the use of light to illuminate the slide under the microscope can sometimes have a destructive effect on the substance-of-interest.

Electronic pH control described in U.S. Pat. No. 10,379,080 (hereby incorporated by reference in its entirety) can provide solutions for some of these problems. A similar pH control scheme can be used in various design formats, especially in an array format to perform highly multiplexed, independent measurements and reactions in parallel within the same sample solution. When using an array of electrodes to locally control the microenvironment near each of the electrodes, "cross-talk" or "bleed-over" between different sites is a concern. This problem is addressed either through spacing out the individual sites, or with a buffering reagent added to the bulk solution. The former approach results in the reduced density of the array (larger device size), and the latter requires that the rate of electrochemical reaction is high enough to overcome the buffering capacity of the bulk solution. In practice, it means applying higher voltage or current, or using higher concentration of electroactive molecules. These measures may lead to side reactions involving other components of the reaction system.

SUMMARY OF INVENTION

Herein are provided closed-loop controls to solve many of the problems described above. Several implementations of the closed-loop in a high-density array of individually addressable electrodes are described herein. Devices and methods for modulating pH or ionic gradient near the electrode surface in an array format are disclosed herein. The device can contain one or more working electrode(s), pH sensing element(s) that can in some instances be a/an electrode(s), counter electrode(s), and reference electrode(s). Each individual working electrode can introduce pH change electrochemically within a small physical space close to the surface in on-demand format. A counter electrode and a reference electrode can be shared by multiple working and sensing elements. pH modulation reagent can be electrochemically oxidized or reduced to generate a pH modulation zone covering a nano- to micro-meter distance from the surface. Electrical output parameters for the working electrodes can be modulated based on the feedback from the sensing elements to achieve faster and more precise pH control.

Some aspects disclosed herein include array-based pH control, a device containing an array-based pH control, and method of use thereof. In some instances, a multi-electrode array contains feedback-controlling electrode sets composed of a working electrode, a reference electrode, a counter electrode, and a sensing element. The reference and the counter electrode can be shared by multiple sets of electrodes. In some instances, each set contains at least a working electrode and a sensing element to be controlled independently. In some instances, each set of electrodes can be programmed for specific pH conditions with temporal variations. The number of electrodes in an array can range from one to hundreds of millions. In some instances, the array is contained in a single or multi-layer device. The device can have various fabrication schemes that include or exclude Complementary Metal Oxide Semiconductors (CMOS), Thin-Film-Transistors (TFT), etc.

In some aspects, a device can contain an array of electrodes in a single device. The device can contain one single section of feedback-controlling electrode sets, or multiple sections of feedback-controlling electrode sets. The feedback-controlling electrode sets can contain a working, a reference, and a counter electrode, and a sensing element that can be an electrode. The reference and counter electrodes can be shared by multiple electrode sets. The section(s) containing feedback-controlling electrode sets can be a feedback-controlling section. This section can be used to identify required electrical parameters to achieve the target pH values. The target pH values can be different and/or changed over time or between different feedback-controlling electrode sets. In some instances, various pH conditions can be tested and/or provided at the same time with the array of electrodes in a single device. The device can also contain electrode sets that do not contain a sensing element and/or are not feedback-controlling electrode sets. The section(s) containing electrode sets that are not feedback-controlling electrode sets can be a non-feedback-controlling section. The electrical parameters identified by use of the feedback-controlling section can be applied to the non-feedback controlling section. A non-feedback-controlling electrode set can have at least one electrode as a working electrode optionally with a reference electrode, and a counter electrode.

In some instances, the device can be used to modify pH values for multiple rounds of reaction steps, some of which require distinct pH values to be allocated to specifically selected electrodes in the array. Non-limiting examples of reactions with multiple round of reaction steps include making a library array of polymers, such as peptides and nucleic acids. In some instances, the device can be used to visualize the pH of one or more area(s) continuously and/or one or more times.

In some aspects, feedback-controlling electrode sets are distributed throughout a substrate, each of one or more being surrounded by non-feedback-controlling electrode sets. In some instances, the non-feedback-controlling electrode sets have various target pH values between non-feedback-controlling electrode sets and/or over time. In some instances, the electrical parameters identified by use of the feedback-controlling electrode sets can be modified before application to the non-feedback-controlling electrode sets to overcome the effect, if any, from the neighboring electrodes. The electrical parameters applied can be modified by averaging the impact from various pH values. In some instances, this configuration can help minimize the influence of the pH control from the adjacent electrode sets.

In some aspects, disclosed herein is a closed-loop pH control, a device containing a closed-loop pH control, and method of use thereof. In some instances, the closed-loop pH control comprises a feedback-controlling electrode set of any of the arrays disclosed herein. In some instances, the array-based pH control contains a closed-loop pH control or a device containing a closed-loop pH control. In some instances, the closed-loop pH control modulates pH electrochemically. The closed-loop pH control can contain a sensing element, a working electrode, a counter electrode, and a reference electrode. In some instances, a sensing element is used as a reference electrode, such as, but not limited to, when the sensing element is stable and/or is placed in a stable pH solution. The counter electrode and the reference electrode can be shared for multiple working electrodes and/or sensing elements. In some instances, an external counter electrode and/or reference electrode can be used. In some instances, a patterned on-chip counter and/or reference electrode can be used. In some instances an external and/or on-chip counter and/or reference electrode can be used. In some instances, a counter electrode is positioned around the working electrode. Positioning the counter electrode around the working electrode may improve precision of pH control in some instances.

A solution can be in contact with the device and/or closed-loop pH control. In some instances, pH modulation reagents are present in the solution. The pH sensing element can be configured to measure the initial pH values of the solution. The initial pH values of the solution can be used to calculate the amount of current or voltage to apply to the working electrode. When the current or voltage is applied to the working electrode, electrochemical oxidation and/or reduction of pH modulation reagents can occur. The oxidation and/or reduction can introduce a local pH change. The local pH change can occur through an equilibration between generation or consumption of protons and buffering capacity of a buffer solution. In some instances, pH changes can occur in an unbuffered solution. In some instances, the local pH change generates a pH modulation zone with a short vertical distance-several nm to several mm—from the surface of the electrode. In some instances, the pH modulation zone allows pH-dependent chemical/biochemical reactions to occur. In some instances, the pH-dependent reactions in the solution only occur within the pH modulation zone. The size of the modulation zone can be dependent on the buffering capacity of the solution. In some instances, the modulation zone is smaller in stronger buffers than in weaker buffers or in a non-buffered solution. In some instance, the pH sensing element monitors actual pH during the modulation of the pH. In some instances, electrical output is continuous through the closed-loop control when the pH sensing element monitors actual pH. Monitoring and modulating pH at the same time can enable a faster and/or more precise control of pH.

The working electrode and sensing element can have various types of shape and size. In some instances, the shape and size depends on the applications and/or the requirement of the array format. In some instances, the working electrode and sensing element are arranged in a slide design. In some instances, the working electrode and the sensing element are in contact with each other. In some instances, the sensing element is physically separated from the working electrode. In some instances, the sensing element is physically separated from the working electrode by a gap. In some instances, the gap can be from 1 nm to 100 microns. In some instances, an insulating layer is placed in between the sensing element and the working electrode. In some instances, a counter electrode at least partially surrounds the working electrode. In some instances, the counter electrode at least partially surrounds the working electrode when the working electrode is configured to contact, or is in contact with a nonbuffered solution.

In some instances, the sensing element contains an electrode coated with a pH sensitive material. In some instances, the sensing element contains a semiconductor-based electrical component. In some instances, the sensing element contains a field-effect transistor. In some instances, the sensing element contains a polymer semiconductor.

These closed-loop controls and devices containing them can be used in methods that can be integrated with for example a CMOS, electrode array, or TFT based biosensor to generate large changes in binding efficiencies between test sites in the biosensor having an array of multiple test sites. In some instances, the current application provides methods to modulate the pH or ionic concentration near electrode surfaces of the array, such as a biosensor. In some instances, the array is used to modulate biomolecular interactions between a probe biomolecule and a biomolecular analyte of interest.

The array-based pH control and devices disclosed herein can be used for various types of applications that include:
controlling and/or monitoring binding interactions among biomolecules;
controlling and/or switching enzymatic activities on/off, controlling chemistry for surface modification;
chemically modifying a molecule;
building a polymer structure through repetitive steps of blocking and de-blocking along with conjugation;
controlling and/or monitoring chemical reaction kinetics; and/or
visualizing pH sensitive reporter molecules.

According to example embodiments, one or more of the following aspects 1 to 52 are provided.

Aspect 1 is a device for controlling pH of a solution on an array of electrodes, the device comprising:
a support; and
an array of electrodes comprising one or more feedback-controlling electrode sets that each includes:
one or more reference electrode;
one or more counter electrode; and
one or more subset comprising a pH sensing element electrically coupled to a working electrode, wherein a reference electrode and/or a counter electrode is electrically coupled with at least one subset,
where the device is configured to iteratively perform the following:
a) select an amount of current and/or voltage to be applied to each working electrode in order to minimize a difference between a signal output of the sensing element and a target sensing value;
b) apply the selected amount of current and/or voltage to each working electrode to change pH of a solution close to the working electrode; and
c) measure the signal output of the sensing element.

Aspect 2 is the device of aspect 1, wherein the one or more reference electrode and one or more counter electrode are electrically coupled with at least one subset through a processor.

Aspect 3 is the device of any one of aspects 1 to 2, wherein the support comprises a glass slide, plastic plate, silicon wafer, glass wafer, quartz wafer, flexible plastic sheet, polymer layer, paper, or a mixture thereof.

Aspect 4 is the device of any one of aspects 1 to 3, wherein the one or more working electrode, reference electrode, counter electrode, and/or sensing element independently comprises a material selected from the group consisting of: metal oxide, glassy carbon, graphene, metal, conducting polymer, silver chloride, saturated calomel, and combinations thereof.

Aspect 5 is the device of any one of aspects 1 to 4, wherein the one or more working electrode, reference electrode, counter electrode, and/or sensing element independently comprises a gold electrode, silver electrode, platinum electrode, normal hydrogen electrode, mercury drop electrode, or a combination thereof.

Aspect 6 is the device of any one of aspects 1 to 5, wherein the sensing element comprises a field-effect transistor, polymer semiconductor, metal electrode, inorganic electrode, organic electrode, or pH sensitive coating material, or combination thereof.

Aspect 7 is the device of aspect 6, wherein the pH sensitive coating material comprises polyaniline, polypyrrole, iridium oxide, indium tin oxide, ion-selective polymer, or a combination thereof.

Aspect 8 is the device of any one of aspects 1 to 7, wherein one or more of the reference electrode(s) is also a sensing element.

Aspect 9 is the device of any one of aspects 1 to 8, wherein the solution is buffered, unbuffered, aqueous, organic, or a mixture thereof.

Aspect 10 is the device of any one of aspects 1 to 9, wherein the solution contains one or more redox active species selected from the group consisting of: quinones, catechols, aminophenols, hydrazines, derivatives thereof, and combinations thereof.

Aspect 11 is the device of any one of aspects 1 to 10, wherein the selected current and/or voltage applied to the working electrode is applied galvanostatically or potentiostatically.

Aspect 12 is the device of any one of aspects 1 to 11, wherein the device comprises or is communicatively coupled to a processor, and wherein selecting an amount of current and/or voltage to be applied comprises applying an algorithm using an input comprising the signal output of the sensing element.

Aspect 13 is the device of any one of aspects 1 to 12, wherein the working electrode, reference electrode, counter electrode, and/or sensing element is electrically coupled to a switch-matrix module.

Aspect 14 is the device of aspect 13, wherein the switch-matrix module comprises Complementary Metal Oxide Semiconductors (CMOS) and/or thin-film transistors (TFT).

Aspect 15 is the device of any one of aspects 1 to 14, wherein the feedback-controlling electrode set is electrically coupled to the device through physical couplings.

Aspect 16 is the device of any one of aspects 1 to 15, wherein at least one of the reference electrode and/or at least one of the counter electrode is electrically coupled to multiple subsets.

Aspect 17 is the device of any one of aspects 1 to 16, wherein the array of electrodes further comprises one or more non-feedback-controlling electrode set(s) comprising:
one or more reference electrode;
one or more counter electrode; and
one or more working electrode, wherein a reference electrode of a non-feedback-controlling electrode set and/or a counter electrode of a non-feedback-controlling electrode set is electrically coupled with at least one working electrode of a non-feedback-controlling electrode set,
wherein the one or more non-feedback-controlling electrode set(s) does not comprise a pH sensing element, wherein:
i. all of the one or more feedback-controlling electrode set(s) is comprised in one section of the device and all of the one or more non-feedback-controlling electrode set(s) is arranged in a physically separate second section of the device; or
ii. the one or more feedback-controlling electrode set(s) is interspersed between two or more non-feedback-controlling electrode sets, and
wherein one or more of the feedback-controlling electrode set(s) is electrically coupled to one or more of the non-feedback-controlling electrode set(s) and the coupled electrode sets are configured to apply the selected amount of current and/or voltage applied to the one or more working electrode of the coupled feedback-controlling electrode set also to the one or more working electrode of the coupled non-feedback-controlling electrode set.

Aspect 18 is a method of controlling a pH of a solution, the method comprising:
a. obtaining a device comprising a feedback-controlling electrode set comprising:
one or more reference electrode;
one or more counter electrode; and
one or more subset comprising a pH sensing element electrically coupled to a working electrode, wherein a reference electrode and/or a counter electrode is electrically coupled with at least one subset;
b. selecting target sensing values for a sensing element based on one or more signal output from a sensing element in a solution comprising a target pH; and
c. iteratively performing the following:
i. selecting an amount of current and/or voltage to be applied to each working electrode in order to minimize a difference between a signal output of the sensing element and a target sensing value;
ii. applying the selected amount of current and/or voltage to each working electrode to change pH of a solution close to the working electrode; and
iii. measuring the signal output of the sensing element.

Aspect 19 is the method of aspect 18, wherein the solution comprises water and/or one or more redox active species, and wherein the current and/or voltage applied to a working electrode electrochemically generates and/or consumes hydrogen ions by an electrochemical reaction of the water and/or the one or more redox active species.

Aspect 20 is the method of any one of aspects 18 to 19, wherein the solution is buffered, unbuffered, aqueous, organic, or a mixture thereof.

Aspect 21 is the method of aspects 19 to 20, wherein the one or more redox active species is selected from the group consisting of: quinones, catechols, aminophenols, hydrazines, derivatives thereof, and combinations thereof.

Aspect 22 is the method of any one of aspects 18 to 21, wherein the one or more working electrode, reference electrode, counter electrode, and/or sensing element independently comprise(s) a material selected from the group consisting of: metal oxide, glassy carbon, graphene, metal, conducting polymer, silver chloride, saturated calomel, and combinations thereof.

Aspect 23 is the method of any one of aspects 18 to 22, wherein the one or more working electrode, reference electrode, counter electrode, and/or sensing element independently comprise(s) a gold electrode, silver electrode, platinum electrode, normal hydrogen electrode, mercury drop electrode, or a combination thereof.

Aspect 24 is the method of any one of aspects 18 to 23, wherein the sensing element comprises a field-effect transistor, polymer semiconductor, metal electrode, inorganic electrode, organic electrode, pH sensitive coating material, or combination thereof.

Aspect 25 is the method of aspect 24, wherein the pH sensitive coating material comprises polyaniline, polypyrrole, iridium oxide, indium tin oxide, ion-selective polymer, or a combination thereof.

Aspect 26 is the method of any one of aspects 18 to 25, comprising determining pH of the solution by comparing the signal output of the sensing element to predetermined calibration data that correlates pH to values of a signal output of the sensing element.

Aspect 27 is the method of any one of aspects 18 to 26, wherein the selected current and/or voltage applied to the working electrode is applied galvanostatically or potentiostatically.

Aspect 28 is the method of any one of aspects 18 to 27, wherein the device obtained comprises an array of two or more feedback-controlling electrode sets.

Aspect 29 is the method of any one of aspects 18 to 28, wherein at least two of the feedback-controlling electrode sets are controlled individually with independent target pH values and/or independent temporal programs for applying the selected amount of current and/or voltage.

Aspect 30 is the method of any one of aspects 18 to 29, wherein the feedback-controlling electrode set is electrically coupled to a switch-matrix module and control of each feedback-controlling electrode set is performed by a switch-matrix module.

Aspect 31 is the method of aspect 30, wherein the switch-matrix module comprises Complementary Metal Oxide Semiconductors (CMOS) and/or thin-film transistors (TFT).

Aspect 32 is the method of any one of aspects 18 to 31, wherein the feedback-controlling electrode set is electrically coupled to the device through physical couplings.

Aspect 33 is the method of any one of aspects 18 to 32, wherein at least one of the reference electrode and/or at least one of the counter electrode is electrically coupled to multiple subsets.

Aspect 34 is the method of any one of aspects 18 to 33, wherein the device obtained is the device of any one of aspects 1 to 16.

Aspect 35 is a method of controlling a pH of a solution, the method comprising:
a. obtaining a device comprising an array of:
one or more feedback-controlling electrode set(s) comprising:
one or more reference electrode;
one or more counter electrode; and
one or more subset comprising a pH sensing element electrically coupled to a working electrode, wherein a reference electrode and/or a counter electrode is electrically coupled with at least one subset; and
one or more non-feedback-controlling electrode set(s) electrically coupled to a feedback-controlling electrode set, the one or more non-feedback-controlling electrode set(s) comprising:
one or more reference electrode;
one or more counter electrode; and
one or more working electrode, wherein a reference electrode of the non-feedback-controlling electrode set(s) and/or a counter electrode of the non-feedback-controlling electrode set(s) is electrically coupled with at least one working electrode of the non-feedback-controlling electrode set(s),
wherein the one or more non-feedback-controlling electrode set(s) does not comprise a pH sensing element;
b. selecting target sensing values for a sensing element based on one or more signal output from a sensing element in a solution comprising a target pH; and
c. iteratively performing the following:
i. selecting an amount of current and/or voltage to be applied to each working electrode of the one or more feedback-controlling electrode set(s) in order to minimize a difference between a signal output of the sensing element and the target sensing value;
ii. applying the selected amount of current and/or voltage to each working electrode of the one or more coupled feedback-controlling electrode set and also to the one or more working electrode of the non-feedback-controlling electrode set coupled to the one or more coupled feedback-controlling electrode set to change pH of a solution close to the working electrodes; and
iii. measuring the signal output of the sensing element.

Aspect 36 is the method of aspect 35, wherein the solution comprises water and/or one or more redox active species, and wherein the current and/or voltage applied to working electrodes electrochemically generates and/or consumes hydrogen ions by an electrochemical reaction of the water and/or the one or more redox active species.

Aspect 37 is the method of any one of aspects 35 to 36, wherein the solution is buffered, unbuffered, aqueous, organic, or a mixture thereof.

Aspect 38 is the method of any one of aspects 36 to 37, wherein the one or more redox active species is selected from the group consisting of: quinones, catechols, aminophenols, hydrazines, derivatives thereof, and combinations thereof.

Aspect 39 is the method of any one of aspects 35 to 38, wherein the one or more working electrode, reference electrode, counter electrode, and/or sensing element independently comprises a material selected from the group consisting of: metal oxide, glassy carbon, graphene, metal, conducting polymer, silver chloride, saturated calomel, and combinations thereof.

Aspect 40 is the method of any one of aspects 35 to 39, wherein the one or more working electrode, reference electrode, counter electrode, and/or sensing element independently comprises a gold electrode, silver electrode, platinum electrode, normal hydrogen electrode, mercury drop electrode, or a combination thereof.

Aspect 41 is the method of any one of aspects 35 to 40, wherein the sensing element comprises a field-effect transistor, polymer semiconductor, metal electrode, inorganic electrode, organic electrode, pH sensitive coating material, or combination thereof.

Aspect 42 is the method of aspect 41, wherein the pH sensitive coating material comprises polyaniline, polypyrrole, iridium oxide, indium tin oxide, ion-selective polymer, or a combination thereof.

Aspect 43 is the method of any one of aspects 35 to 42, comprising determining pH of the solution by comparing the signal output of the sensing element to predetermined calibration data that correlates pH to values of a signal output of the sensing element.

Aspect 44 is the method of any one of aspects 35 to 43, wherein the selected current and/or voltage applied to the working electrode is applied galvanostatically or potentiostatically.

Aspect 45 is the method of any one of aspects 35 to 44, wherein the device obtained comprises an array of two or more feedback-controlling electrode sets.

Aspect 46 is the method of aspect 45, wherein at least two of the feedback-controlling electrode sets are controlled individually with independent target pH values and/or independent temporal programs for applying the selected amount of current and/or voltage to the working electrode of the feedback-controlling electrode set and the working electrode of the coupled non-feedback-controlling electrode set.

Aspect 47 is the method of any one of aspects 35 to 46, wherein the feedback-controlling electrode set is electrically coupled to a switch-matrix module and control of each feedback-controlling electrode set is performed by a switch-matrix module.

Aspect 48 is the method of aspect 47, wherein the switch-matrix module comprises Complementary Metal Oxide Semiconductors (CMOS) and/or thin-film transistors (TFT).

Aspect 49 is the method of any one of aspects 35 to 48, wherein the feedback-controlling electrode set and non-feedback-controlling electrode set are electrically coupled to the device through physical couplings.

Aspect 50 is the method of any one of aspects 35 to 49, wherein the reference electrode and/or the counter electrode of one or more of the feedback-controlling electrode set is electrically coupled to multiple subsets of the feedback-controlling electrode set and/or to multiple working electrodes of the non-feedback-controlling electrode set.

Aspect 51 is the method of any one of aspects 35 to 50, wherein the working electrode of the coupled non-feedback-controlling electrode set has a similar shape and design to the working electrode of the coupled feedback-controlling electrode.

Aspect 52 is the method of any one of aspects 35 to 51, wherein the device obtained is the device of aspect 17.

As used herein, various terminology is used for the purpose of describing particular implementations only and is not intended to be limiting of implementations.

For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term).

The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" and "about" may be substituted with "within 10 percent of" what is specified. Additionally, the term "substantially" and "about" may be substituted with "within [a percentage] of" what is specified, where the percentage includes 0.1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), "contain" (and any form of contain, such as "contains" and "containing") and "include" (and any form of include, such as "includes" and "including") are non-limiting and open ended and can include additional steps, material, etc. with its scope. As a result, an apparatus that "comprises," "has," "contains," or "includes" one or more elements possesses those one or more elements, but is not limited to possessing only those one or more elements. Likewise, a method that "comprises," "has," "contains," or "includes" one or more steps possesses those one or more steps, but is not limited to possessing only those one or more steps.

Any aspect of any of the material, compositions, systems, methods, and article of manufacture can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE FIGURES

FIG. 2: Illustration of the undesired cross-reactivity. Molecules other than the antigen of interest (diamond) can bind to primary antibody or the surface and either create incorrect signal or prevent the antigen in forming a sandwich.

FIG. 3: Illustration of the multisite sensor and the components in the detected signal. The two schematics on the bottom correspond to two of the sites.

In FIG. 12A, the profile of fluorescence intensity across the spot is shown. In FIG. 12B, the changes in the GFP spot fluorescence intensity are shown before (0 sec), during (40 sec), and after (110 sec) applying a current through an electrode.

FIG. 22: provides structures of hydroquinones and benzoquinones that can be used for pH generation in biological solutions, according to an example embodiment of the present invention.

FIGS. 54A-54B: FIG. 54A illustrates a pH control device setting with an external counter and a reference electrode, according to an example embodiment of the present invention. FIG. 54B illustrates a pH control device setting with a counter and a reference electrode on the substrate, according to an example embodiment of the present invention. The device can have one or more sets of working electrode and sensing element that are controlled individually.

FIGS. 55A-54D: illustrate examples of pH control electrode designs, according to an example embodiment of the present invention. Working and sensing electrodes can have various types of shape and size depending on the application (Figure A and Figure B). The sensing electrode can be positioned on the same plane with the working electrode Figure C or on top of the working electrode with an insulation layer in-between Figure D. The counter electrode can be patterned around the working electrode, which minimizes the diffusion effect and helps control pH within a more definitive physical space Figure E.

DETAILED DESCRIPTION

Figure 1:
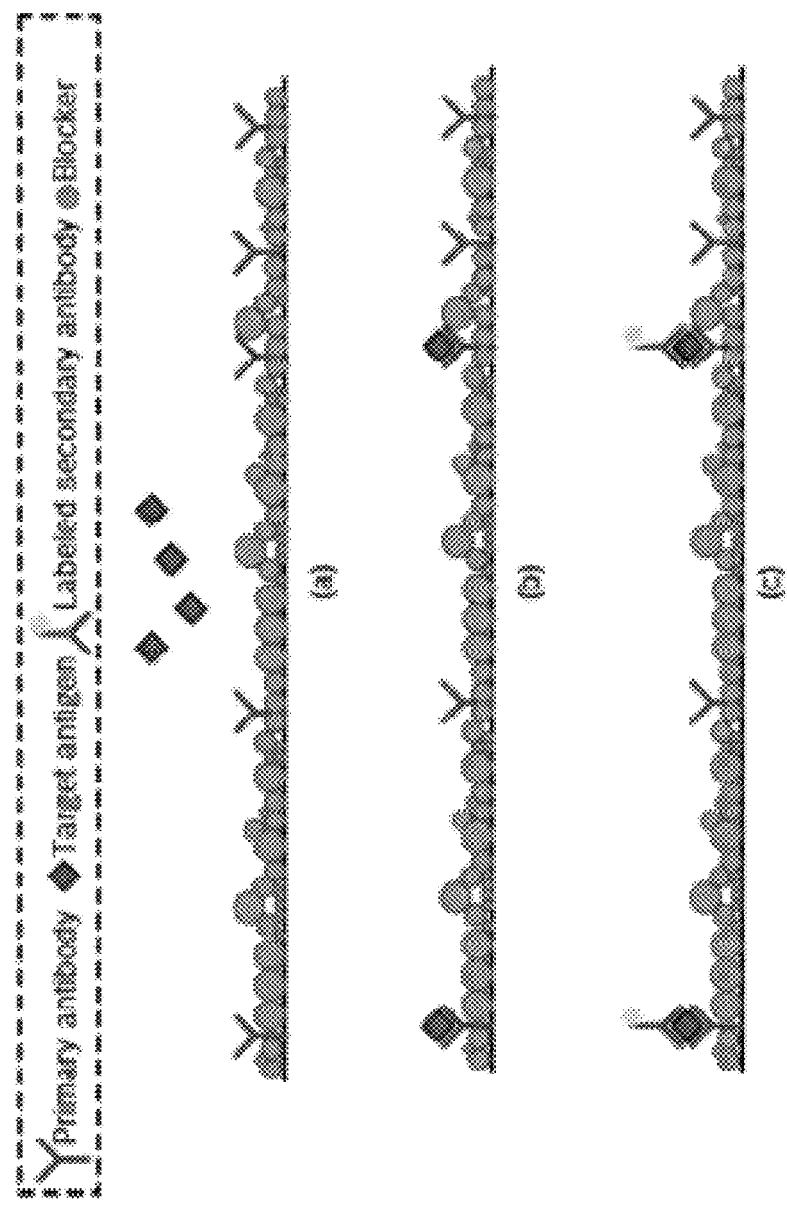
FIG. 1: Illustration of the steps of a typical and well known ELISA assay: a) Sample introduced to immobilized primary antibody on a blocked surface and incubated, b) Sample washed, and c) labeled secondary antibody is added. The number of labels is proportional to the concentration of target antigen.

Herein are provided closed-loop controls to address problems associated with electronic control of pH. Several implementations of the closed-loop in a high-density array of individually addressable electrodes are described herein. Devices and methods for modulating pH or ionic gradient near the electrode surface in an array format are disclosed herein. Each individual working electrode can introduce pH change electrochemically within a small physical space close to the surface in on-demand format. The electrical configuration can be composed of one or more working electrodes, pH sensing elements such as sensing electrodes, counter electrodes, and reference electrodes. A counter electrode and a reference electrode can be shared by multiple working electrodes and sensing elements. pH modulation reagent can be electrochemically oxidized or reduced to generate a pH modulation zone covering a nano- to micrometer distance from the surface. Electrical output parameters for the working electrodes can be modulated based on the feedback from the sensing elements to achieve faster and more precise pH control.

In order to vary the pH or ionic concentration gradient in a multisite array there is provided a device comprising:
 a support; and
 an array of electrodes comprising one or more feedback-controlling electrode set comprising:
  one or more reference electrode;
  one or more counter electrode; and
  one or more subset comprising a pH sensing element electrically coupled to a working electrode, wherein a reference electrode and/or a counter electrode is electrically coupled with at least one subset.

The device is configured to iteratively perform the following:
 a.) select an amount of current and/or voltage to be applied to each working electrode in order to minimize a difference between a signal output of the sensing element and a target sensing value;
 b.) apply the selected amount of current and/or voltage to each working electrode to change pH of a solution close to the working electrode; and
 c.) measure the signal output of the sensing element.

The device can further comprise one or more non-feedback-controlling electrode set comprising:
 one or more reference electrode;
 one or more counter electrode; and
 one or more working electrode, wherein a reference electrode and/or a counter electrode is electrically coupled with at least one working electrode,
 wherein the one or more non-feedback-controlling electrode set does not comprise a pH sensing element,
 wherein:
  all of the one or more feedback-controlling electrode set(s) is comprised in one section of the device and all of the one or more non-feedback-controlling electrode set(s) is arranged in a physically separate second section of the device; or
  the one or more feedback-controlling electrode set(s) are interspersed between two or more non-feedback-controlling electrode sets, and
  wherein one or more feedback-controlling electrode set is electrically coupled to one or more non-feedback-controlling electrode set and the coupled one or more feedback-controlling electrode set and one or more non-feedback-controlling electrode set are configured to apply the selected amount of current and/or voltage applied to the one or more working electrode of the feedback-controlling electrode set also to the one or more working electrode of the coupled non-feedback-controlling electrode set.

Also disclosed herein is a method of controlling a pH of a solution, the method comprising:
 a. obtaining a device comprising a feedback-controlling electrode set comprising:
  one or more reference electrode;
  one or more counter electrode; and
  one or more subset comprising a pH sensing element electrically coupled to a working electrode, wherein a reference electrode and/or a counter electrode is electrically coupled with at least one subset;
 b. selecting target sensing values for a sensing element based on one or more signal output from a sensing element in a solution comprising a target pH; and
 c. iteratively performing the following:
  i. selecting an amount of current and/or voltage to be applied to each working electrode in order to minimize a difference between a signal output of the sensing element and a target sensing value;
  ii. applying the selected amount of current and/or voltage to each working electrode to change pH of a solution close to the working electrode; and
  iii. measuring the signal output of the sensing element.

Further disclosed herein is a method of controlling a pH of a solution, the method comprising:
 a. obtaining a device comprising an array of:
  one or more feedback-controlling electrode set(s) comprising:
   one or more reference electrode;
   one or more counter electrode; and
   one or more subset comprising a pH sensing element electrically coupled to a working electrode, wherein a reference electrode and/or a counter electrode is electrically coupled with at least one subset; and
  one or more non-feedback-controlling electrode set(s) electrically coupled to a feedback-controlling electrode set, the one or more non-feedback-controlling electrode set(s) comprising:
   one or more reference electrode;
   one or more counter electrode; and
   one or more working electrode, wherein a reference electrode and/or a counter electrode is electrically coupled with at least one working electrode, and wherein the one or more non-feedback-controlling electrode set does not comprise a pH sensing element;
 b. selecting target sensing values for a sensing element based on one or more signal output from a sensing element in a solution comprising a target pH; and
 c. iteratively performing the following:
  i. selecting an amount of current and/or voltage to be applied to each working electrode of the one or more feedback-controlling electrode set(s) in order to minimize a difference between a signal output of the sensing element and the target sensing value;
  ii. applying the selected amount of current and/or voltage to each working electrode of the one or more coupled feedback-controlling electrode set and also to the one or more working electrode of the non-feedback-controlling electrode set coupled to the one or more coupled feedback-controlling electrode set to change pH of a solution close to the working electrodes; and
  iii. measuring the signal output of the sensing element.

The methods can utilize the device described above.

In the above described method and by use of the above described device, a local pH or ionic concentration gradient can be obtained in the various working electrode sites, such as in a multisite array like a biosensor or reactor for producing libraries of compounds or reactor for quickly producing large amounts of compounds. As a non-limiting example, the variation of the local pH and/or ionic concentration gradient at the electrode, and in particular in the vicinity of a probe, such as a biomolecular probe, in a biomolecular interface layer, over subsets of the multisite array of the biosensor, allows for modulating the binding efficiency of the probe and an analyte to be tested from a biological sample. The analyte of interest, when bound to the probe, can be then detected using a detection agent, such as for example a labeled secondary antibody. The modulation of binding efficiencies in a subset of a multisite array provides a method for the accurate determination of such analyte of interest.

As another non-limiting example, the device and methods can be used to modify pH values for multiple rounds of reaction steps, some of which require distinct pH values to be allocated to specifically selected electrodes in the array. Non-limiting examples of reactions with multiple round of reaction steps include making a library array of polymers, such as peptides and nucleic acids.

As yet another non-limiting example, the device and methods can be used to visualize the pH of one or more areas continuously or one or more times.

The device preferably comprises a multisite array of feedback-controlling electrode sets. Such a multisite array preferably includes a number of different test sites, reaction sites, or other means for varying pH at the different feedback-controlling electrode sets sites. Each site can represents a site for performing an analysis of a (biomolecular) analyte from a biological sample through the detection of the (biomolecular) analyte using a (biomolecular) probe. The analytical conditions in each site in each of the feedback-controlling electrode sets may be varied to obtain a collection of varied signals that will result in multiple equations and multiple unknowns from which the concentration of the (biomolecular) analyte can be determined in order to obtain an accurate measurement of the (biomolecular) analyte. Each site can also represent a site for preforming a different chemical reaction that requires one or more different steps with different pH requirements. The analytical conditions in each site in each of the feedback-controlling electrode sets can be varied to obtain a collection of varied chemical reaction products that will result in production of a library of chemicals, such as a protein library, a nucleic acid library, or an organic chemical library.

For visualizations, testing of concentrations of analytes, etc., the multiple unknowns in the obtained varied signals each includes a term that is proportional to a binding efficiency factor, $\alpha_{ij}$, and the concentrations of the various molecules in the biological sample binding that are detected at the test site. The multiple equations with multiple unknowns may be represented for example as follows, $$\begin{cases} S_1 = \alpha_{11}C_{an} - \alpha_{12}C_{j1} + \alpha_{13}C_{j2} + \alpha_{14}C_{j3} \\ S_2 = \alpha_{21}C_{an} - \alpha_{22}C_{j1} + \alpha_{23}C_{j2} + \alpha_{24}C_{j3} \\ S_3 = \alpha_{31}C_{an} - \alpha_{32}C_{j1} + \alpha_{33}C_{j2} + \alpha_{34}C_{j3} \\ S_4 = \alpha_{41}C_{an} - \alpha_{42}C_{j1} + \alpha_{43}C_{j2} + \alpha_{44}C_{j3} \end{cases} \Longrightarrow C_{an}$$

where $C_{an}$ corresponds to the targeted biomolecular analyte concentration and $C_{j1}$, $C_{j2}$, $C_{j3}$ correspond to the total concentration of molecules which result in different terms in background signal, from which collection of multiple equations the concentration of the targeted biomolecular analyte can be determined.

The number of feedback-controlling electrode sets, as well as the number of sites within each feedback-controlling electrode sets can be varied, as needed. Some of these analytical conditions include parameters such as for example temperature, shear stress, and pressure. For example the temperature of the solution in which the biomolecular probe and analyte of interest in the biological sample interact or the reaction takes place can be varied using the electromagnetic heat at the test site. Another important condition for the interaction between the biomolecular probe and the analyte of interest or for the reaction is the pH or ionic concentration. The method and devices described herein modulate this pH or ionic concentration in the local environment of site in order to affect, for example the binding efficiency in the vicinity of the biomolecular probe or the reaction rate in the vicinity of the reactants.

Figure 52:
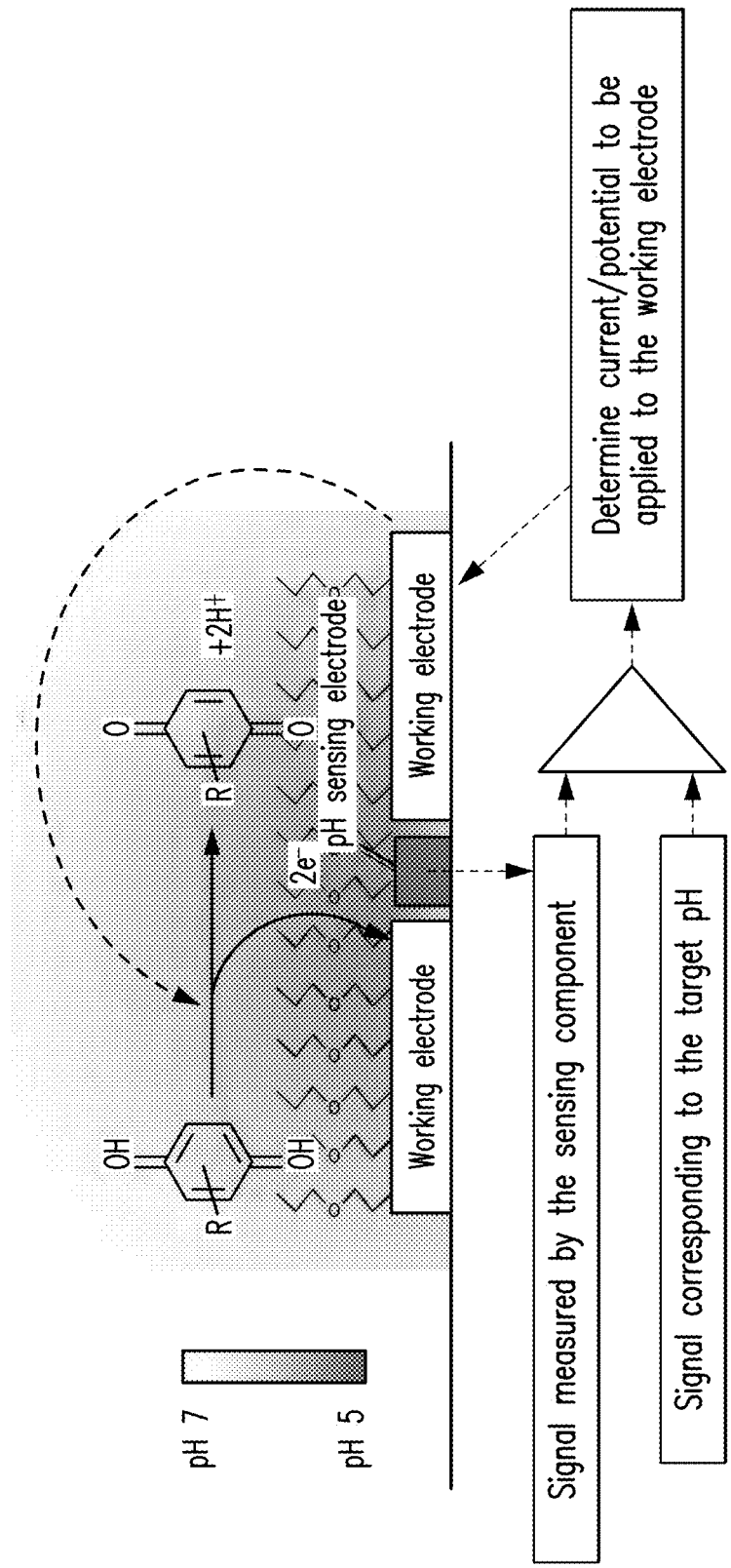
FIG. 52: illustrates a schematic for modulating pH of a solution via oxidation/reduction of redox active species (in this example, quinones) with a closed-loop control, according to an example embodiment of the present invention.

As a non-limiting example of a device disclosed herein, each site in the multi-site array can comprise a support onto which one or more electrodes and/or pH sensors are placed. Biomolecular probe(s) or reactants can be immobilized or bound on the surface as well. This immobilization of probes or a reactant to a solid surface or support assists in reducing the amount of probe or reactant needed for the analytical method and also localizes the detection/reaction area to make accurate measurements and/or reduce bleed over to different reaction sites. The probes and/or reactants can be attached to solid surfaces of the support and/or electrodes such as those of silicon, glass, metal and semiconductor materials (as shown in FIGS. 3, 4, and 52).

Figure 4:
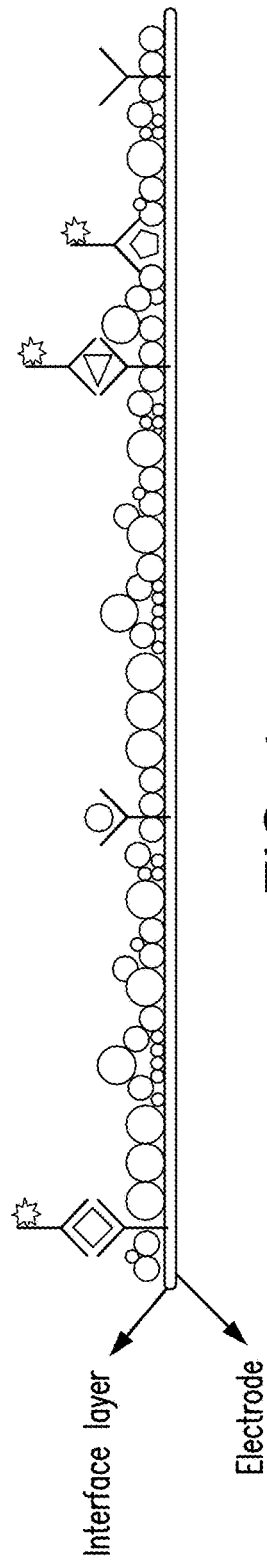
FIG. 4: Illustration of the composition of a sensor test site in a multisite sensor.
Figure 5:
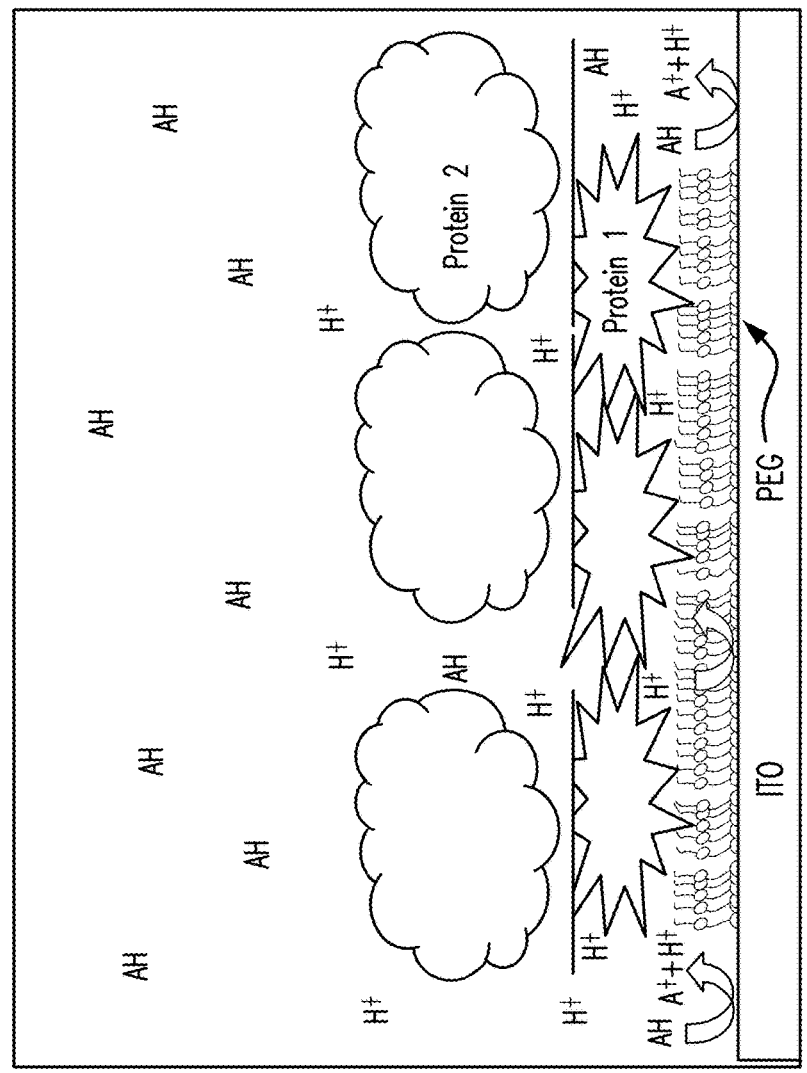
FIG. 5: Schematic of the pH change on an electrode surface using electrochemical method.

The probe and/or reactant can be attached or immobilized onto the support and/or electrode(s) within a biomolecular interface layer (as shown in FIG. 4). The biomolecular layer can include a layer of immobilized polymers, preferably a silane immobilized polyethylene glycol (PEG). Surface-immobilized polyethylene glycol (PEG) can be used to prevent non-specific adsorption of biomolecular analytes and/or reactant onto surfaces. At least a portion of the surface-immobilized PEG can comprise terminal functional groups such as N-hydroxysuccinimide (NHS) ester, maleimide, alkynes, azides, streptavidin or biotin that are capable of conjugating. The probe and/or reactant can be immobilized by conjugating with the surface-immobilized PEG. It is important that the method used to change the pH does not impair the covalent binding of, for example, the PEG onto the surface of a solid support, or the linker that conjugated the probe or reactant to the PEG (as shown in FIG. 5). The method of modulating the pH or ionic concentration as described herein can protect these surface chemistries, while affecting a pH/ionic concentration change in the environment of the probe and/or reactant.

A suitable biomolecular probe can be a carbohydrate, a protein, a glycoprotein, a glycoconjugate, a nucleic acid, a cell, or a ligand for which the analyte of interest has a specific affinity. Such probe can for example be an antibody, an antibody fragment, a peptide, an oligonucleotide, a DNA oligonucleotide, a RNA oligonucleotide, a lipid, a lectin that binds with glycoproteins and glycolipids on the surface of a cell, a sugar, an agonist, or antagonist. In a specific example, the biomolecular probe is a protein antibody which interacts with an antigen that is present for example in a biological sample, the antigen being a biomolecular analyte of interest.

In the analytical method described herein the analyte of interest in a biological sample can be for example a protein, such as an antigen or enzyme or peptide, a whole cell, components of a cell membrane, a nucleic acid, such as DNA or RNA, or a DNA oligonucleotide, or a RNA oligonucleotide.

A suitable reactant can, for non-limiting examples, be a carbohydrate, a protein, a glycoprotein, a glycoconjugate, a nucleic acid, a nucleotide, an amino acid, or another organic chemical precursor for which a further reactant can react to produce the desired product or intermediate. Such reactant can, for non-limiting examples, be a peptide, an oligonucleotide, a DNA oligonucleotide, a RNA oligonucleotide, a lipid, or a sugar.

A biosensor comprising the device provided herein can be used in an analytical method for determining a biomolecular analyte of interest in a biological sample, which can be for example a protein, such as an antigen or enzyme or peptide, a whole cell, components of a cell membrane, a nucleic acid, such as DNA or RNA, or a DNA oligonucleotide, or a RNA oligonucleotide.

In such method a local pH or ionic concentration gradient can be obtained at various test sites in a multisite array biosensor. The variation of the local pH and/or ionic concentration gradient at the working electrode, and in particular in the vicinity of the (biomolecular) probe in a biomolecular interface layer, over subsets of the multisite array of the biosensor, allows for modulating the binding efficiency of the (biomolecular) probe and an analyte to be tested from a biological sample. The analyte of interest, when bound to the (biomolecular) probe, can be then detected using a detection agent, such as for example a labeled secondary antibody. The modulation of binding efficiencies in a subset of a multisite array provides a method for the accurate determination of such analyte of interest.

A reaction vessel comprising the device provided herein can be used in an analytical method for producing a library of compounds, which can be for example a protein, such as a peptide, or a nucleic acid, such as DNA or RNA, DNA oligonucleotide, RNA oligonucleotide, or a protein and nucleic acid conjugate, or an organic compound, such as a polymer or pharmaceutical.

In such method, a local pH or ionic concentration gradient can be obtained at various sites in a multisite array. The variation of the local pH and/or ionic concentration gradient at the working electrode, and in particular in the vicinity of the (biomolecular) probe in a biomolecular interface layer or a reactant bound to a surface, over subsets of the multisite array, allows for modulating the binding efficiency of the (biomolecular) probe and an analyte to be tested from a biological sample or modulating the reaction rate of reactants. In some instances, an analyte of interest, when bound to the (biomolecular) probe, can then be detected using a detection agent, such as for example a labeled secondary antibody. The modulation of binding efficiencies in a subset of a multisite array provides a method for the accurate determination of such analyte of interest. In some instances, the product of interest produced from the reactions facilitated near the working electrodes can be released from the surface by a further reaction.

The electrodes can each be any electrode suitable for the intended purpose of the device, for example metal oxide, glassy carbon, graphene, metal, gold, silver, platinum, conducting polymer, silver chloride, normal hydrogen, mercury drop, saturated calomel, or combinations thereof. For biosensors, the electrodes can include indium tin oxide (ITO), gold, silver electrodes, or combinations thereof. In a preferred embodiment the electrodes in a biosensor in the method described herein are indium tin oxide (ITO) electrodes.

The pH sensing element can be any element suitable for sensing pH, for example, it can be formed by a combination of one or more electrical components that include field-effect transistors, polymer semiconductor, metal electrode, inorganic electrode, organic electrode, and pH sensitive coating materials that include polyaniline, polypyrrole, iridium oxide, indium tin oxide, and ion-selective polymer. In some instances, the pH at each site is determined by the fluorescence intensity of a pH sensitive Fluorescent Protein.

The solution contacting the working electrode can be any solution suitable for the intended purpose of the device, for example, a buffered, unbuffered, aqueous, organic solution, or a mixture thereof. In some instances, the solution contains one or more redox active species. The redox active species can be any species suitable for the intended purpose of the device, such as quinones, catechols, aminophenols, hydrazines, derivatives thereof, and combinations thereof. The solution can contain water, a buffer inhibitor, a probe, a target, a reactant, suspended particles, a reporting molecule, an enzyme, a substrate, a cell, a virus, a solvent, a co-solvent, a catalyst, etc. In some instances, the solution is a biological sample. In some instances, the solution contains a pH sensitive fluorescent protein, such as Green Fluorescent Protein (GFP). In some instances, the solvent or co-solvent is water, acetonitrile, dimethyl sulfoxide (DMSO), dimethyl formamide (DMF), and/or N,N-dimethyl acetamide (DMAc). In some instances, the solution contains a buffer, such as a phosphate buffer. In some instances, the solution contains an electrolyte, such as a salt, such as sodium sulfate, sodium chloride, or potassium chloride. The amount of water in the solution in some instances can be from 0.0001 wt. % to 100 wt. %, such as 0.001, 0.01, 0.1, 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.9 wt. %, or any range or percentage thereof or therebetween.

The support can be any support suitable for the intended purpose of the device, for example, a material that can have patterned electrodes. The surface can be materials such as a glass slide, plastic plate, silicon wafer, glass wafer, quartz wafer, flexible plastic sheet, polymer layer, paper, or a mixture thereof. The support can contain thereon or therein one or more electrodes, sensors, electromagnets, an interface layer having one or more immobilized detection agents, probes, reactants, enzymes, cells, catalysts, cells, viruses, substrates, reporting molecules, etc. In some instances, the surface has immobilized thereon a pH sensitive fluorescent protein, such as Green Fluorescent Protein (GFP). In some instances, the support is coated with PEG. The surface and the things contained thereon or therein can vary from site to site to facilitate detection of different targets or product of different products.

A biomolecular analyte can be detected using any suitable detection method. Known detection methods of such analyte include luminescence, fluorescence, colorimetric methods, electrochemical methods, impedance measurements, or magnetic induction measurements. In various of such methods, the analyte binds to an immobilized biomolecular probe and a detection agent such as for example a secondary labeled probe that specifically binds to the analyte, bound to the immobilized probe, is introduced. This detection agent or secondary labeled probe can give rise to a detectable signal such as for example luminescence or fluorescence.

In analytical methods, such as biomolecular probe detection and chemical reactions, the pH of the solution surrounding the biomolecular probe or reactants has been known to influence the binding/activity between the probe and the analyte to a great extent or the reaction rate. Concentration of other ions can also heavily influence the binding/activity/reaction. Herein are provided devices and methods to modulate the pH and/or ionic concentration in the vicinity of the probe or reactants close to a working electrode. The modulation of the pH near the working electrode can also affect the non-specific interactions of analytes and reactants to other molecules other than the probe or intended reactants and the interactions of other molecules in the solution with the probe, analyte, or reactant. The modulation of pH or ionic concentration however can be controlled to not impair any of the surface chemistries, such as those that immobilize the biomolecular probe or a reactant to a solid support in a site of a multisite array. The method of modulating the pH or ionic concentration as described herein can protect these surface chemistries, while affecting a pH/ionic concentration change in the environment of the probe or reactants.

Surface chemistry compatibility can be considered when the methods described herein are practiced. pH change is caused by changes in hydrogen ion or hydroxyl ion concentrations. A variety of chemical reactions taken place at electrode-liquid, electrode-cross linker, cross linker-protein, and protein-protein interfaces as shown in FIG. 5 can also become a hindrance to pH changes happening near the solid surfaces to reach the probes or reactants on top of them. They can act as diffusion barriers for the ions and hinder the pH changes around the probes, analytes, and reactants. These methods of modulating the pH or ionic concentration described herein helps in maximizing the changes in hydrogen or hydroxyl ion concentration so that they can overcome any diffusion barrier imposed by the surface chemistry.

Another important aspect is the buffering capacity of the solution in contact with the solid interface. The buffering effect can be large enough that the pH change at the interface would never reach the probes or reactants that are immobilized away from it. The distance can vary based on the interface layer deposited on top of the solid interface. Such interface layer may have a thickness of 300 nm or less, preferable between 1-150 nm, even more preferably between 5-100 nm. As such the distance between the solid interface and the probe or reactant within the interface layer can range between 0.1-300 nm. Use of buffer inhibitors in the solution or on the surface that extend the pH change on the electrode interface to reach the interacting probe-analyte pair or reactants may contribute to modulating the pH or ionic concentration in the vicinity of the probe and/or reactants.

Following are examples of methods for modulating the pH/ionic concentration at the solid-liquid interfaces. These include: 1) the electrochemical generation of ions at electrode surfaces by adding an electrochemically active species to the solution which generates ions of interest (e.g., $H^+$, $Mg^+$, $OH^-$) upon electrochemical oxidation/reduction; 2) bringing enzymes close to the site of interest, which release such ions of interest from an enzyme substrate that is reacted with the enzyme; 3) the introduction of buffer inhibitors, for example, by mixing polymers that selectively reduce the diffusion rate of ions in the solution (e.g., phosphate). U.S. Pat. No. 7,948,015 describes the use of such inhibitors for applications in which measuring small local pH changes is of interest (e.g., in DNA sequencing). However in the methods of locally modulating the pH similar inhibitors can be used in order to extend the local pH changes further away from the electrode-liquid interface; and 4) the redistribution of preexisting ions near the electrode surface due to electrostatic forces.

In one embodiment of a method for modulating the pH or ionic concentration as described herein, an electrochemically active agent is added to the solution at a site in a multisite array, wherein the site has an interface layer comprising a probe, detection agent, or reactant and oxidizing or reducing the electrochemically active agent. The electrochemically active agent may be added at a concentration of 1 nM to 100 mM, preferably at a concentration between 10 nM and 10 mM, more preferably at a concentration of 100 nM and 5 mM. The electrochemically active agent may be electro-oxidized or electro-reduced at an electrode potential in the range of −2V to +2V (vs. Ag/AgCl reference electrode). Preferably the electrode potential is in the range of −1V to +1V, even more preferably the electrode potential is in the range of −0.5V to +0.5V. The voltage required to drive the redox reaction can be used as a real time feedback method to monitor pH that is produced at the electrode surface.

The device provided herein can comprise such arrays of multiple sites in solution in order to modulate the pH at each test site. In some instances, this is used to determine the presence and concentration of a biomolecular analyte of interest in a biological sample or to facilitate a multistep chemical reaction. In such uses, the device can be in contact with a solution comprising a phosphate buffer, preferably a diluted phosphate buffer which preferably has a concentration of 0.1 mM to 100 mM. In a preferred embodiment, the pH of the diluted phosphate buffer is between 5 and 8, preferably between 7 and 8, and more preferably between 7 and 7.5.

Modulation of the pH or ionic concentration on a device described herein by electrochemical reaction at the one or more working electrode can be carried out in a galvanostatic mode or potentiostatic mode. In addition, any type of electrical pulse may be applied on the electrodes of the device in the method for modulating the pH. Such pulse can be in the form of an annealing pulse and can vary by pulse frequency, pulse width, and pulse shape. In an annealing pulse a sufficient voltage is applied to change the pH to such that non-covalently bound molecules are removed from the device. Such annealing pulse eliminates or reduces the need for washing the substrate following first contact with a sample or reactant solution in order to remove non-covalently bound material. Another advantage is that the annealing pulse may be more efficient to remove such non-covalently bound material from the device than a simple washing. A preferred pulse width for modulating the pH is in the range of 1 nanosecond to 60 minutes.

The solution can further comprise one or more electrolytes, such as for example sodium sulfate, or any other suitable strong electrolyte. Preferably, the electrolyte is selected from sodium sulfate, sodium or potassium chloride, sodium or potassium bromide, sodium or potassium iodide, sodium or potassium perchlorate, sodium or potassium nitrate, tetraalkylammonium bromide and tetraalkylammonium iodide. Buffer-inhibitors can also be used in the solution. Suitable buffer inhibitors may be selected from poly(allylamine hydrochloride), poly (diallyldimethyl ammonium chloride), poly(vinylpyrroldone), poly(ethyleneimine), poly(vinylamine), poly(4-vinylpyridine) and tris(2-carboxyethyl)phosphine hydrochloride. When used in a method to modulate the pH such as described in U.S. patent application Ser. No. 13/543,300, the aqueous solution preferably also comprises a water-miscible organic co-solvent selected from the groups consisting of acetonitrile, dimethyl sulfoxide (DMSO), dimethyl formamide (DMF), N,N-dimethyl acetamide (DMAc), and mixtures thereof.

Suitable electrochemically active agents include dopamine hydrochloride, ascorbic acid, phenol and derivatives, benzoquinones and derivatives, for example, 2,5-dihydroxy-1,4-benzoquinone, 2,3,5,6-tetrahydroxy-1,4-benzoquinone and 2,6-dichloroquinone-4-chloroimide; naphthoquinones and derivatives, for example, hydroxy-1,4-naphthoquinone, 5,8-dihydroxy-1,4-naphthoquinone, and potassium 1,4-naphthoquinone-2-sulfonate; and 9,10-anthraquinone and derivatives, for example, sodium anthraquinone-2-carboxylate, potassium 9,10-anthraquinone-2,6-disulfonate. Preferably the concentration of the electrochemically active agent in the aqueous solution is from 1 nM to 100 mM.

In another embodiment of a method for modulating the pH or ionic concentration in a solution, an enzyme is immobilized in an interface layer or magnetic particle. The interface layer or magnetic particle can also have one or more immobilized biomolecular probes or reactants therein or thereon. An enzyme substrate is then added to the solution at a site in a multisite array, wherein the site has the interface layer and enzymatically oxidizes the enzyme substrate.

Figure 6:
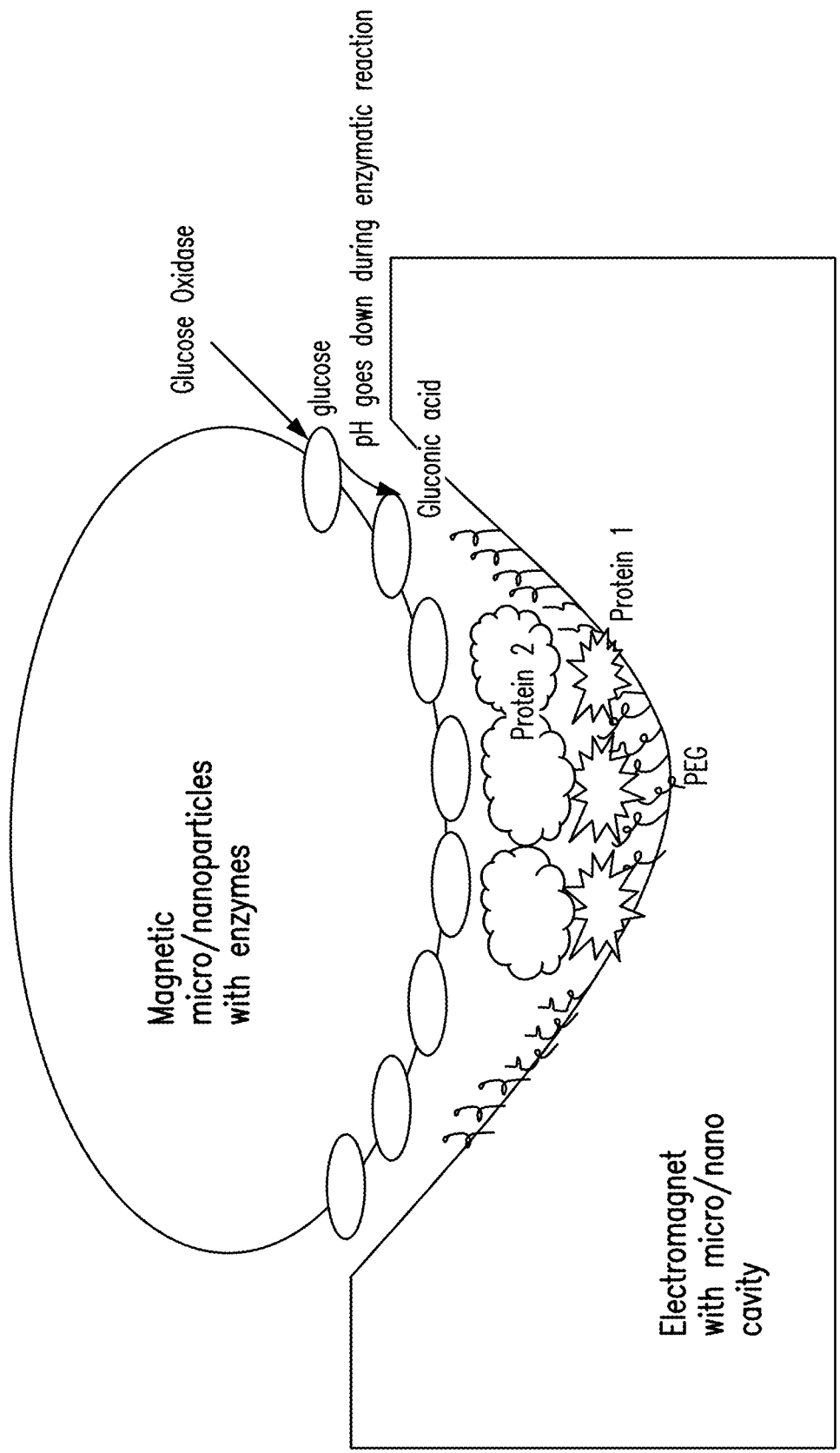
FIG. 6: Illustration of pH change by enzymatic reactions when they are brought close to the protein surface using magnetic micro/nanoparticles. The micro/nano cavity helps in localizing the pH change.

Suitable enzymes for immobilization in the interface layer or onto magnetic micro- or nano-particles include for example oxidases, ureases, or dehydrogenases. Such immobilized oxidase can be, for example, a glucose oxidase with the enzyme substrate as glucose (as shown in FIG. 6). The amounts of immobilized enzyme and enzyme substrate added can be varied in the different sites of the multisite array so as to provide a pH or ionic concentration gradient in the multisite array.

Alternatively the enzyme is not immobilized onto a solid surface such as in the above methods being immobilized into an interface layer or onto a magnetic micro- or nano-particle but is added to the solution in the sites of a multisite array. Through electrolysis, the enzyme undergoes a redox reaction at the electrode surface and perturbs the local pH.

In each of these embodiments the pH or ionic concentration can be further modulated by adding a buffer inhibitor to the solution. Such addition of a buffer inhibitor either assists in diffusing the produced ions of interest to the location of the probe, reactant, detection agent or the addition inhibits the interaction of such produced ions with buffering salts. Alternatively, in the method of modulating the pH or ionic concentration as described herein, the buffer inhibitor is added to the solution of the site in the absence of an electrochemical active agent or immobilized enzyme. In such embodiment the buffer inhibitor is added to the solution, and facilitates the diffusion of $H^+$ ions or $OH^-$ ions that are produced at the working electrodes in the site or inhibits the interaction between $H^+$ ions or $OH^-$ ions and buffering salts.

Suitable buffer inhibitors include soluble polymers selected from poly(allylamine hydrochloride), poly (diallyldimethyl ammonium chloride), poly(vinylpyrrolidone), poly(ethyleneimine), poly(vinylamine), poly(4-vinylpyridine) and tris(2-carboxyethyl)phosphine hydrochloride. The amounts of buffer inhibitor added can be varied in the different sites in each of the subsets of the multisite array so as to provide a pH or ionic concentration gradient in the multisite array.

When methods for modulating the pH in a multisite array of sites are used in a biosensor or reactor, the accuracy, reliability and reproducibility of the modulation of the pH at each site is important. However, the modulation of the pH at each site may vary between subsequent uses. In order to accurately determine the amount of an analyte of interest in a sample or to accurately prepare the reaction conditions using the device and method described above, the pH at each site should be accurately modulated or controlled. The device provided herein allows for accurate determination and control of the pH at each site.

Figure 10:
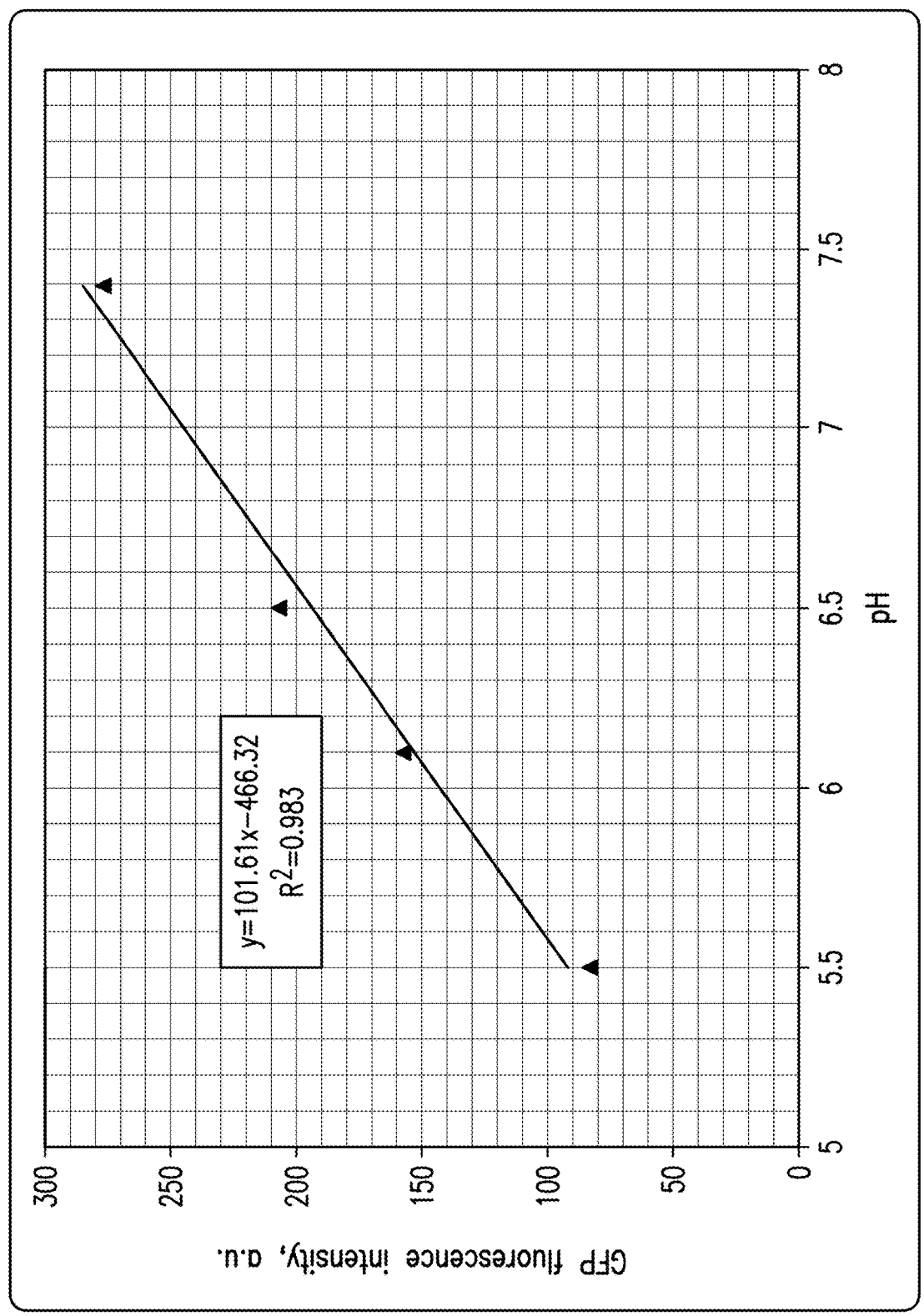
FIG. 10: shows the change in the fluorescence intensity of GFP covalently bound to the PEG-coated ITO in response to the change in solution pH. The solution pH was adjusted by adding HCl to a dilute phosphate buffer (pH 7.4).

The pH sensor allows for sensing the pH at an electrode once the electrode (working electrode) causes modulation of the pH at a particular site in a multisite array. In an example, fluorescence intensity of a fluorescent protein is used by the sensor. The fluorescence intensity can change due to modulation of the pH. The change in fluorescence intensity of the fluorescent protein can be proportional to the change in the pH (e.g., when there is a linear relationship between the pH and the fluorescence intensity). Therefore, as is also shown in FIG. 10, the pH value at each location at any time can be readily obtained by correlating the fluorescence intensity of the fluorescent protein with the pH. An accurate calibration of the correlation between pH and fluorescence intensity can be carried out before or during use of the device. Preferably, the fluorescent protein is selected from green fluorescent protein, yellow fluorescent protein, and cyan fluorescent protein. More preferably, the fluorescent protein is immobilized Green Fluorescent Protein (GFP). In an alternative embodiment pH sensitive dyes can be used instead of a pH sensitive fluorescent protein. In another alternative embodiment pH sensitive binding proteins can be used.

Figure 12A:
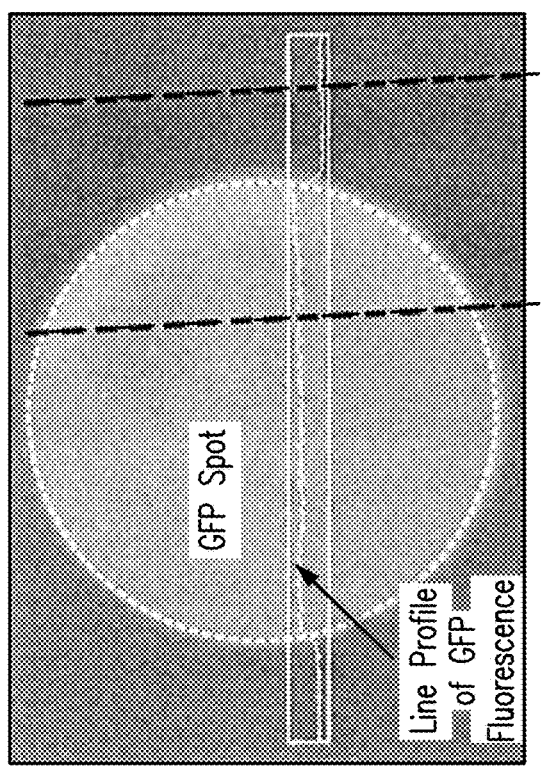
FIGS. 12A-12B: illustrate the visual changes in the GFP spot before, during and after pH modulation experiment.

In a multisite array of sites, a pH sensor can cover on the surface an area that is also covered by an electrode and an area that is not covered with an electrode. The electrode covered by the pH sensor is either a working electrode or a counter electrode. Preferably, the pH sensor is applied onto the surface at a distinct spot, wherein each spot overlaps with only one site and an area not covered by an electrode as shown in FIG. 12A. The presence of a pH sensor on an area that is not covered by an electrode allows for the determination of the pH sensor output when the pH is not modulated by the electrode. This pH sensor output can be used as a standard and control in determining whether, after ceasing modulation of the pH by an electrode, the pH sensor output will revert back to its original intensity. Accordingly, the pH sensor not located on or near an electrode can be used as an internal reference for signal normalization.

When the calibration is carried out during use of the device, one or more sites within a multisite array can be dedicated to calibration of the pH sensor output to pH correlation. When the pH is no longer modulated at such site by the electrode (working electrode) the pH sensor output can revert back to its intensity before a current was applied through the electrode.

The device includes one or more counter electrodes and one or more working electrodes. In the device, one or more electrodes can be arranged in a multisite array, each site of the multisite array can comprise a working electrode and/or counter electrode. The electrodes can be any electrode suitable for the intended purpose of the device, for example indium tin oxide (ITO), gold, or silver electrodes. In a preferred embodiment the electrodes in the device are indium tin oxide (ITO) electrodes. In an alternative embodiment the working electrode is an indium tin oxide electrode and the counter electrode(s) is selected from an indium oxide electrode, a gold electrode, a platinum electrode, a silver electrode, and a carbon electrode.

The electrodes in the device may be used either for modulating the pH or as sensing electrodes or both. In the device or biosensor using the device, the one or more electrodes can be connected to an electronic board via pogo-pins, a chip on foil via z-axis adhesive, or a chip on the substrate. The electronic board or chip can be powered by a printed battery, a small battery bound to the substrate, a magnetically coupled power transfer using coils on the substrate, or a rf-coupled power transfer using coils on the substrate.

Figure 9:
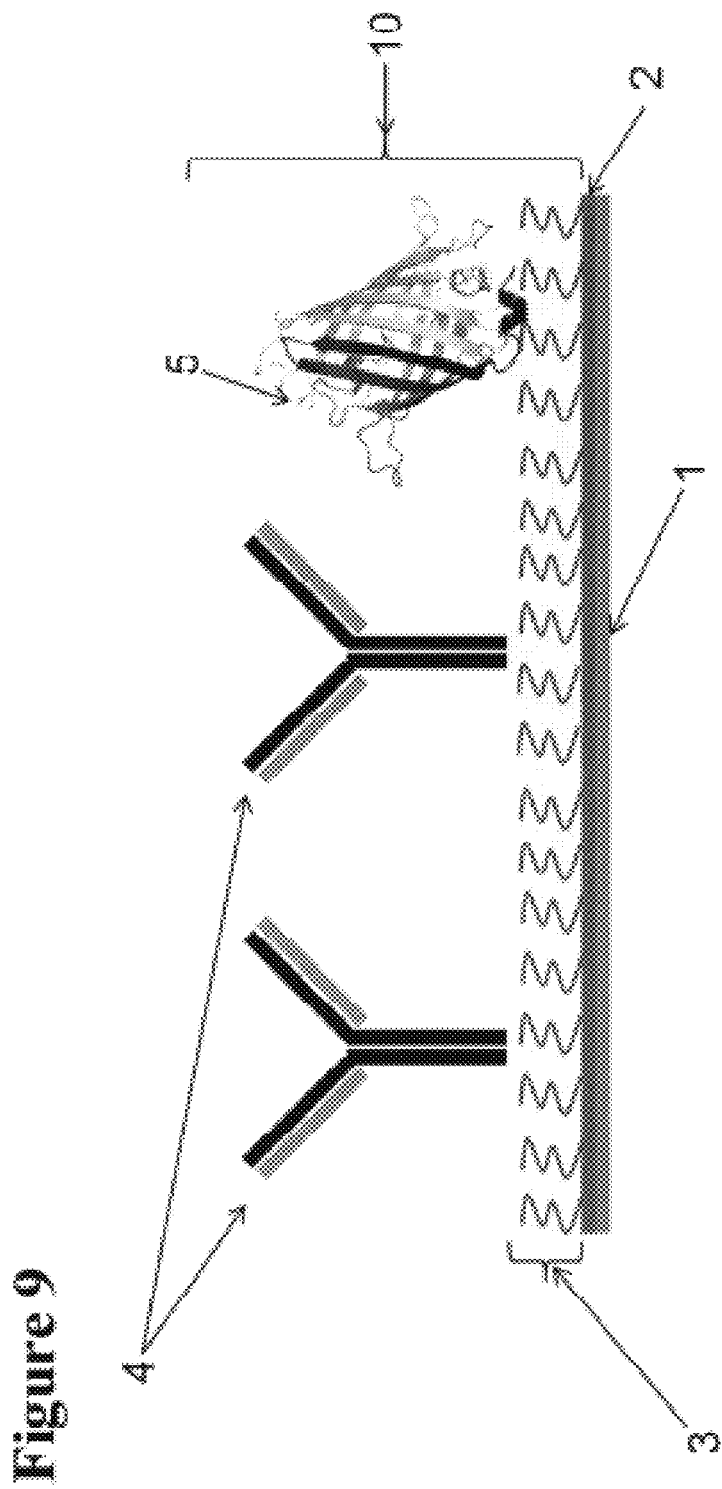
FIG. 9: Illustration of a substrate (glass or plastic) (1) with an array of electrodes (2) onto which a biomolecular interface layer (10) is applied which include fluorescence protein (such as Green Fluorescence Protein (GFP)) spots (5), and immobilized probes (4), immobilized using a polyethylene glycol (PEG) linker (3).

The following description is an illustration of a specific embodiment which may be modified within the scope of the description as would be understood from the prevailing knowledge. FIG. 9, shows a side view of a part of a device which includes a substrate (1) for example glass or plastic. One or more electrodes (2) are covered onto the substrate (1) which is also covered with a biomolecular interface layer (10). The biomolecular interface layer (10) comprises immobilized PEG (3), immobilized probe (4) and immobilized pH sensitive fluorescent protein in the form of Green Fluorescent Protein spots (5). The GFP spots (5) overlap with an electrode (2) and an area that is not covered by an electrode. The electrodes (2) and the GFP spots (5) are arranged in a multisite array so as to provide multiple test sites on the device.

The location of luminescence signals generated luminescent molecules can be controlled by directly controlling the location of the luminescent molecules themselves. This includes for example immobilizing the luminescent molecule. However, by incorporating the ability to control the pH of a solution near an electrode with pH sensitive luminescent molecules the location of luminescence signals generated by free floating luminescent molecules can also be controlled.

Figure 14:
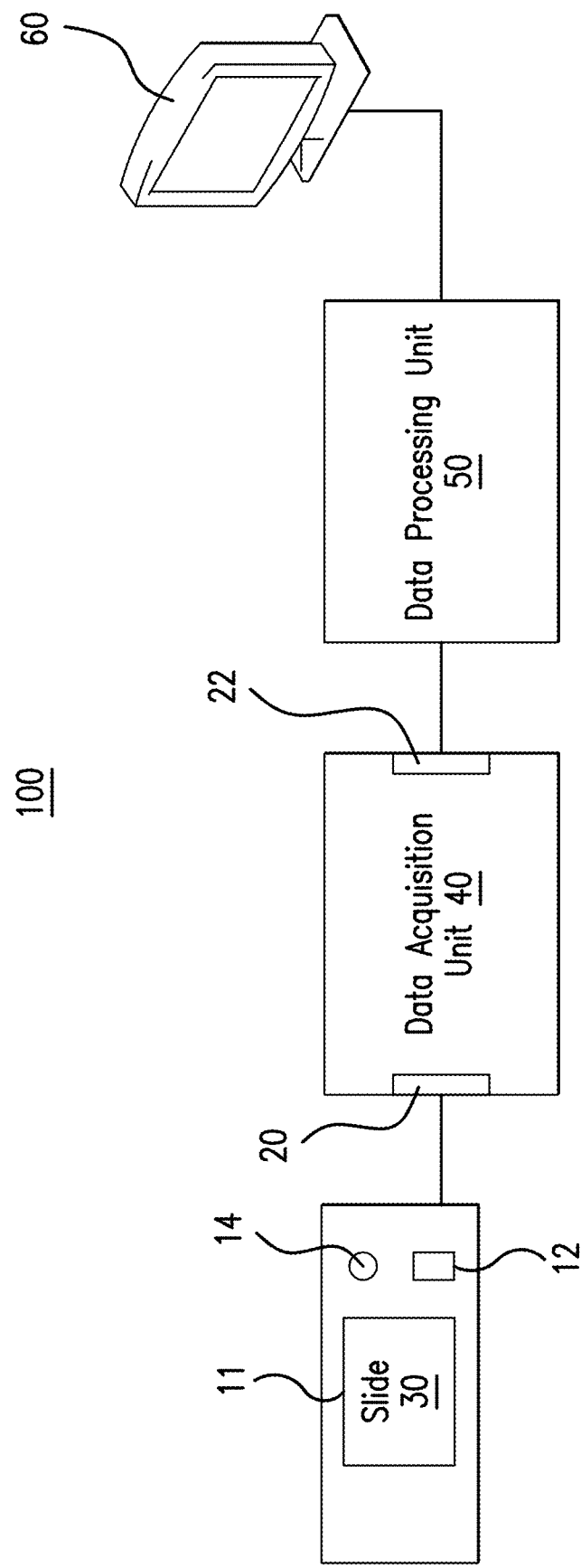
FIG. 14: is a block diagram of a system for bubble detection and/or controlling pH, according to an example embodiment of the present invention.

FIG. 14 shows an example system 100 for controlling pH according to an example embodiment of the present invention. In the example shown in FIG. 14, the system 100 includes a slide 30 that includes an area 11 in which a test solution containing a substance-of-interest is placed, a control unit 12 and a power source 14. The slide 30 can be formed of any electrically insulating material. For example, glass would typically be used for this purpose and to serve as a substrate, on top of which the area 11, control unit 12 and power source 14 are formed. The glass can be formed, for example, of silicon dioxide ($SiO_2$), possibly with additives. Alternatively, other types of silicate glasses may be used.

The area 11 includes an array of electrodes used for controlling pH. In an example embodiment, at least some of the electrodes in the area 11 are used for detecting a pH level of the test solution. (For example, U.S. patent application Ser. No. 13/543,300, mentioned earlier, describes the use of electrodes for pH modulation in a biosensor, which modulation can be performed using the electrodes discussed herein.)

Figure 15:
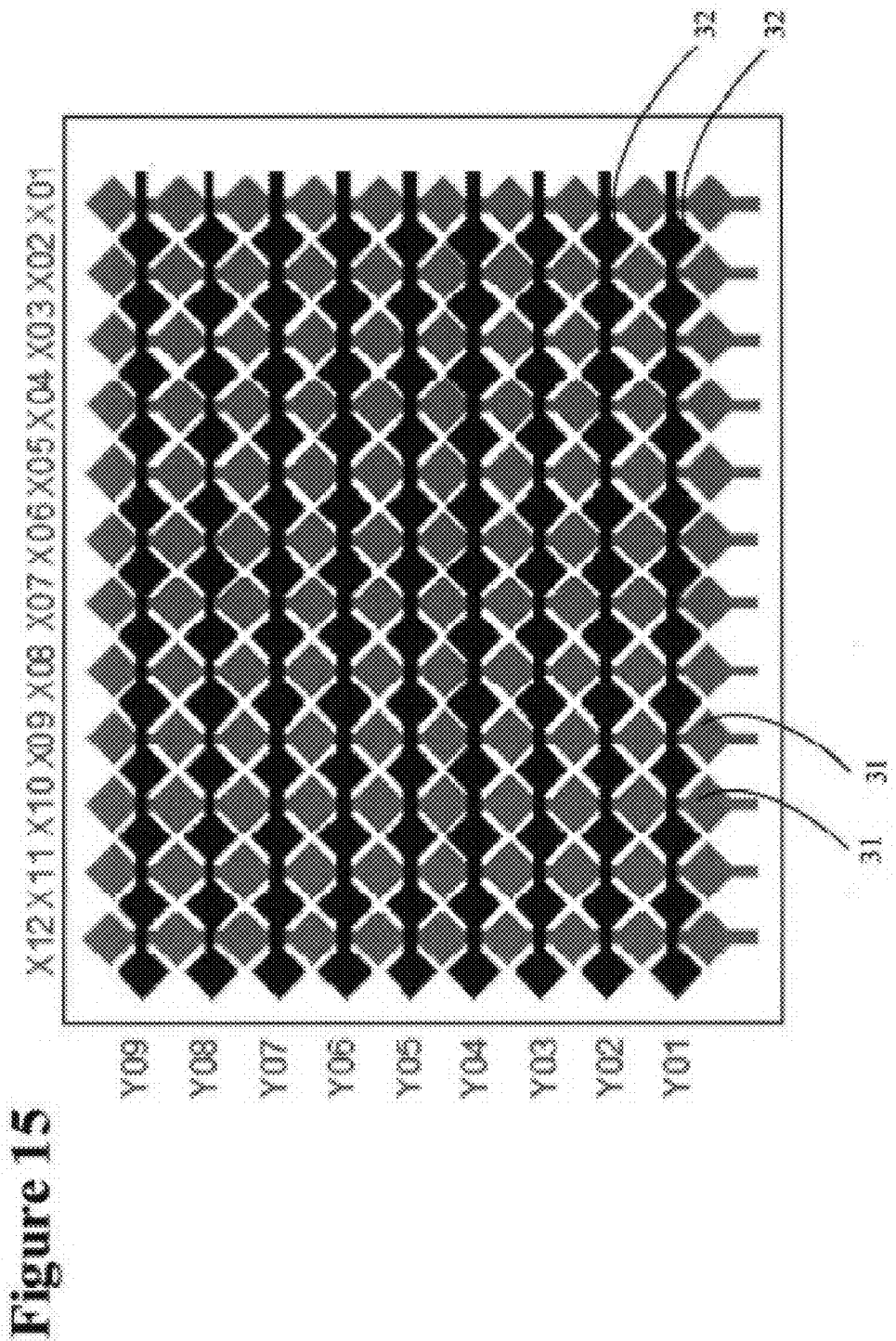
FIG. 15: is a top view of an example electrode array, according to an example embodiment of the present invention.
Figure 17:
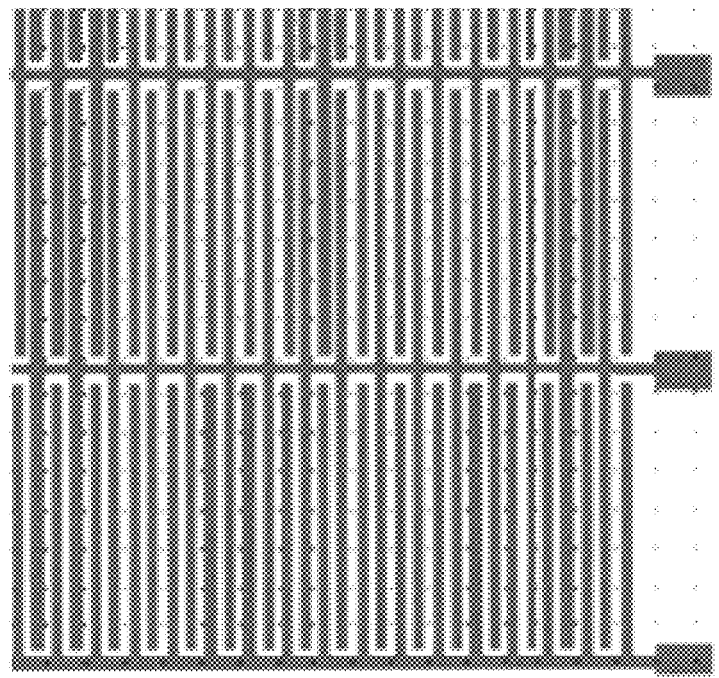
FIG. 16 and FIG. 17: show different electrode shapes, according to example embodiments of the present invention.
Figure 16:
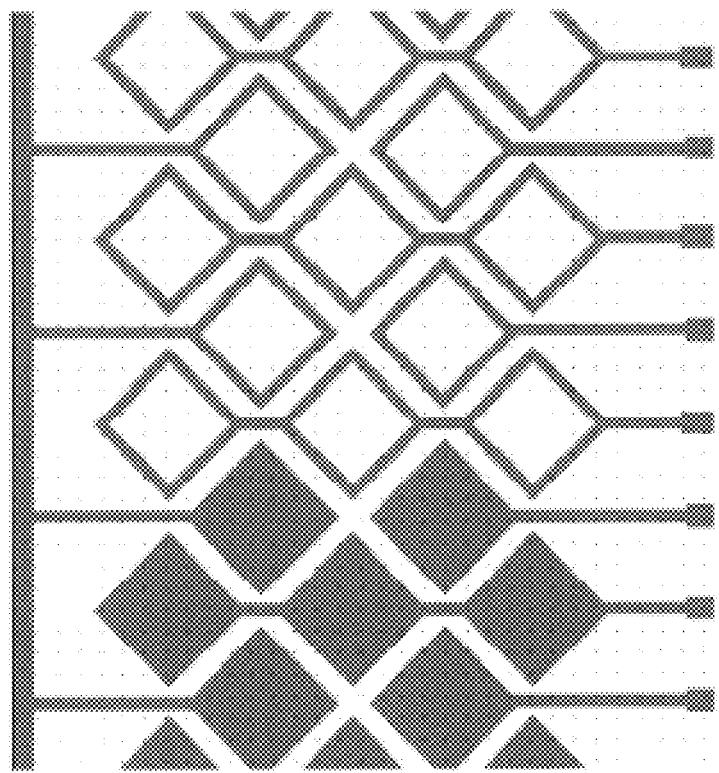

FIG. 15 shows a top view of an example electrode array, in which a set of column electrodes X01 to X12 are arranged at regularly spaced distances from each other. A set of row electrodes Y01 to Y09 are also arranged at regularly spaced distances and are separated from the column electrodes X01 to X12, e.g., by an intervening layer of glass. Each electrode includes one or more contact pads 31, 32 for use in pH modulation. The shape of the pads is variable and, in an example embodiment, is substantially square. FIG. 16 shows a close-up view of example square-shaped pads. FIG. 17 shows an alternative embodiment in which the pads form an interdigitated structure, and are therefore frame-shaped.

In the example illustrated in FIG. 14, the control unit 12 is electrically connected to the electrode array 11 and controls the array 11 to perform pH modulation. The control unit 12 can be, for example, a microprocessor or an application specific integrated circuit (ASIC). In an example embodiment, the control unit 12 is located on an electronic circuit board that is detachably connected to the slide 30, e.g., using pogo pins. The control unit 12 can be located within a packaged chip bonded directly to a rigid glass substrate, e.g., using a chip-on-glass process. In an alternative example embodiment, the slide 30 is formed of a flexible foil-type substrate and the control unit 12 is glued to the slide 30 using a z-axis adhesive to form a chip-on-foil, in a manner similar to how chips are bonded in certain liquid crystal displays. The control unit 12 can include, for example, a non-transitory computer readable storage medium containing program code that implements the pH modulation techniques described herein. In addition to pH modulation, the control unit 12 can control the electrodes to perform other types of sensing or to control other sensing structures, such as bubble detection, or other sensing or controls as is known in the art of biosensors.

In an example embodiment, the control unit 12 transmits control signals that cause input pulses to be applied at specified electrodes. Capacitance and/or pH values can be measured at the control unit 12 based, in some instances, on the responses of the electrodes to the input pulses. The measurement of capacitance is known in the art of touch screen displays, which utilize measurements of self-capacitance (e.g., a single electrode) or mutual capacitance (e.g., between two electrodes). In some instances, to also support bubble detection, the control unit 12 has a capacitance detection range that is greater than that of typical control units that measure capacitance in life science experiments. Control signals can be used to apply input pulses for pH modulation. Control signals for pH modulation can be initiated by the control unit 12, e.g., in accordance with a predefined program sequence designed for pH modulation. Alternatively, the control signals for pH modulation is initiated externally, e.g., in response to a command from a data processing unit 50. In an example, the control unit 12 includes hardware and/or software components that perform preliminary signal processing on the measured capacitance values and/or pH values, including converting the measurements from analog to digital format and/or filtering the measurements. In an example, the processed measurements are then output as raw data to the data acquisition unit 40.

The power source 14 provides power to the control unit 12 and to the electrode array 11. For example, in an example embodiment, the power source 14 is a battery such as a coin-cell or a printed battery. In one example embodiment, the slide 30 is designed for one-time use and is disposable, the battery therefore being provided with a small energy capacity, e.g., sufficient for a single measurement, and the battery can be permanently attached to the slide, e.g., bonded or glued to the glass surface. In an example embodiment where the slide 30 is reusable, the battery can be rechargeable or user replaceable. Other forms of electric power delivery may alternatively be used. In one example embodiment, electrical power is delivered wirelessly through magnetic coupling between an external power supply (e.g., the data acquisition unit 40) and one or more resonant coils in the slide. As an alternative to magnetic coupling, but also using wireless power transfer, the external power supply may couple to the resonant coil using radio-frequency (RF) signals. In yet another example embodiment, the slide 30 receives power through a wired connection to the data acquisition unit 40.

In an example, the data acquisition unit 40 is a device that communicates with the slide 30 to receive the measured capacitance and/or pH values from the control unit 12, in the form of raw data. For example, in an example, the data acquisition unit 40 includes a wired communication interface 20 to a corresponding interface in the slide 30. In one example embodiment, the raw data is output from the control unit 12 in parallel. For example, in an example embodiment, the control unit 12 includes a plurality of output channels, with data from a single row or a single column being output on a corresponding channel. In this embodiment, the interface 20, for example, converts the parallel data into a format suitable for transmission to the data processing unit 50. The conversion may involve parallel-to-serial conversion using a Universal Asynchronous Receiver/Transmitter (UART) or other conventional data conversion apparatus. In an alternative embodiment, the interface 20 communicates wirelessly with the slide 30, e.g., using RF signals.

In an example embodiment, the data processing unit 50 receives the raw data from an output interface 22 of the data acquisition unit 40, e.g., from a transmitter portion of the UART. The output interface 22 can be a wired, serial interface such as a Universal Serial Bus (USB) interface. Alternatively, the output interface 22 can be wireless, e.g., a Bluetooth or WiFi interface. In an example, the interface is a Bluetooth low energy (LE) interface. The data processing unit 50 can be, for example, a general purpose computer in the form of a desktop, a laptop or tablet, and includes, for example, a processor and a memory storing instructions for further processing of the raw data. For example, in an example embodiment, the further processing includes normalizing the raw data to a predefined scale and using the normalized data to generate output images, such as two or three-dimensional graphs, for display at the display device 60. Where the data processing unit 50 is a laptop or tablet, the display device 60 can be integrated into a housing of the data processing unit 50 as a single unit. The display device 60 may alternatively be externally connected, e.g., where the data processing unit 50 is a desktop. The output images may be combined to form a video that shows changes in the data over time. In one embodiment, the output images, which represent the measured capacitance values and/or pH values, are displayed together with additional output images corresponding to other measured data. For example, the output images and the additional output images may be displayed in different portions of the same display screen or overlaid (superimposed) on the same portion of the display screen.

In an example embodiment, the data processing unit 50 is also configured to issue commands to the control unit 12 for pH modulation. The commands may be automatically generated, e.g., when a processor of the data processing unit 50 determines that the pH level of the test solution should be adjusted. Alternatively or additionally, the commands may be user-initiated.

According to an example embodiment, the slide 30 may include a layered structure in which one or more electrode layers are located on top of a glass substrate. The layered structure can be formed, for example, using a lamination technique in which two or more layers are formed separately and then laminated together, e.g., using adhesive or bonding. Alternatively, the layered structure can be monolithically formed as a single unit, using techniques known in the art of semiconductor device fabrication. The layered structure may include one or more passivating layers formed, e.g., of $SiO_2$ (also referred to as oxide). However, it will be understood that the composition and size of passivating layers can vary, e.g., from an atomic layer of $SiO_2$ to several micrometers of $SiO_2$, and formed using various techniques such as low pressure chemical vapor deposition (LPCVD) or plasma-enhanced chemical vapor deposition (PECVD). Silicon nitride ($Si_3N_4$) is another example passivating material. Where the layered structure is formed using lamination, the passivating layer can be formed as a thin film that is laminated.

Figure 13:
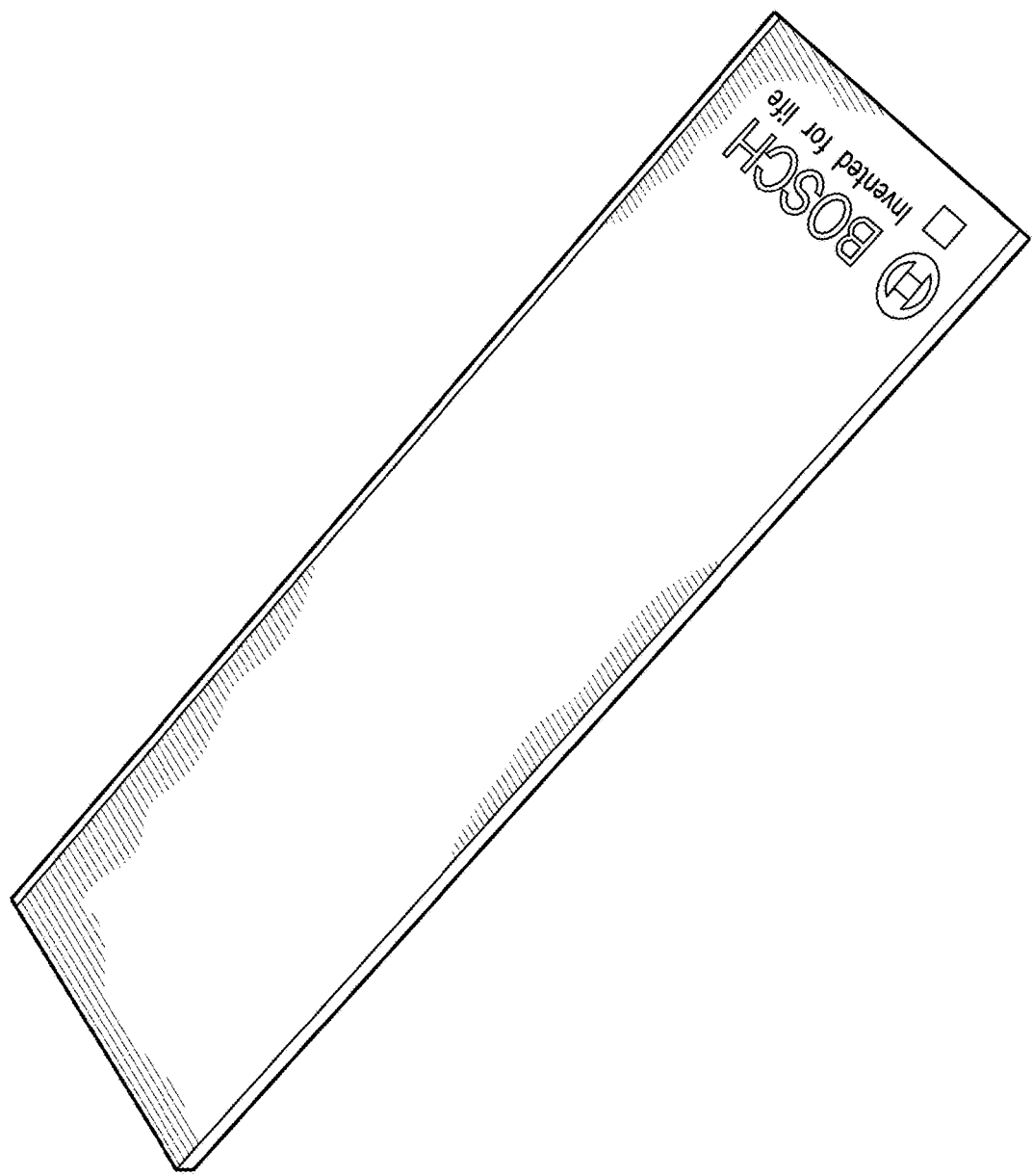
FIG. 13: shows a glass slide with an ASIC chip interfaced to transparent ITO electrodes.

One way to perform pH modulation is to separate the pads of adjacent electrodes so as to form channels that collect the test solution. The channels allow the test solution to come into contact with the electrodes, so that the pH level of the solution can be adjusted by sending a current between the adjacent electrodes. According to an example embodiment, the electrodes can be formed of any suitable conductive material, but are preferably indium tin oxide (ITO) because ITO is transparent and relatively colorless, making it suitable for experiments that involve optical measurements. This allows the entire measurement area 11 to be transparent as shown in FIG. 13. An oxide layer can be used as a passivating layer to cover the electrodes. Where the pH modulation is implemented using channels, in an example embodiment, the oxide layer does not completely fill the channels, but instead a lateral portion of the electrodes is left exposed to allow for contact with the test solution.

The results of pH measurements can be an output for display at the display device 60. According to an example embodiment, raw data values are displayed in the form of a two-dimensional table. Each table entry corresponds to a measured pH value obtained from a corresponding electrode pad. The raw data may be displayed as a three-dimensional graph, e.g., a 3-D mesh where the x and y values correspond to electrode locations and the z values correspond to measured pH values. To facilitate visual recognition, in an example embodiment, the graph can be color coded, e.g., using a gradient scheme, e.g., a gray scale scheme or a heat map in which the color gradually changes as pH changes. In another embodiment, color coding is used to show pH locations on a two-dimensional graph in which the pH values are represented using changes in color. Alternatively or additionally to the display of raw data, the data processing unit 60, according to an example embodiment, processes the raw data by normalizing it to a predefined scale. The above described graphs can be displayed alone or together with additional values from other parameters that are the subject of the experiment, e.g., capacitance value and flow rate. In one embodiment, the additional values are displayed on the same graph, e.g., using a different color scheme and superimposed onto the pH values.

Advantageously, the graphical display of the pH values allows a user to quickly determine the pH as specific locations, and to take appropriate corrective action in response to the pH. The user may decide, for example, to keep those additional values (corresponding to one or more parameters being measured by the experiment) which are not associated with the locations of particular pH values, while discarding values associated with locations of the particular pH values. Alternatively, the user may decide that the entire set of data should be discarded because of an abundance of pH values outside the desired range, thus making the additional values unreliable as a whole.

According to an example embodiment, the pH values are superimposed onto additional measurement data, which additional data is stored in association with layout data representing the physical configuration of the measurement area. The layout data may be stored in an electronic file in the form of an image (e.g., a scanned image of the measurement area) or text (e.g., a configuration file for a microarray spotter used to fabricate the array, or a GenePix Array List (GAL) file). The additional measurement data can also be image or text (e.g., measured capacitance values stored in a GAL file or measured capacitance values rendered in grayscale on a scanned image of the measurement area).

According to an example embodiment in which the pH values are superimposed, a composite display can be generated, which display shows a graphical representation of the array together with the pH values superimposed onto the additional measurement values at corresponding locations in the array. The superimposition can be rendered as text-on-text, text-on-image or image-on-image. An example of text-on-text is displaying a pH value in one half of an array location and additional measurement data in the other half. An example of text-on-image is displaying the pH using a heat map while representing the additional measurement data as numerical values on the heat map. An example of image-on-image is displaying the pH using a heat map while representing the additional measurement data using a 3-D mesh. Superimposed data may be stored in the electronic layout file, prior to or in conjunction with the superimposed display.

According to an example embodiment, a processor on the slide or on an external computer is configured to automatically invalidate the additional measurement data (e.g., by replacing measurement values with null values) in response to pH values outside of the desired range. For example, the processor on the slide can detect the pH of some locations and output an indication of where the pHs are located to the external computer, which then performs the invalidating based on the indicated locations. This spares the user from having to manually review the pH values to decide whether to keep the additional measurement data or products produced by the reactions within those locations.

According to an example embodiment, the electrodes can be used to perform functions in addition to pH detection and pH modulation. For example, electrodes can be used for bubble detection. In some examples, the electrodes can be used for temperature modulation. As another example, capacitance measurements can be used to estimate the dielectric constant of the solution, which dielectric constant is then correlated to a rate of cell growth, rate of production of a reaction product, or a rate with which a substance-of-interest binds to a biomolecule. In some instances the functions of the electrodes can be changed between one function and another.

Example embodiments are described in which the electrodes were arranged in two layers. However, the number of layers can be more or less. In fact, a single layer can be sufficient for both pH modulation and pH measurement. Additionally, not every electrode layer needs to be used for pH modulation or pH measurement. Instead, further electrode layers can be used for other purposes, in accordance with the usage of electrodes in conventional biosensors or reactors.

Figure 18:
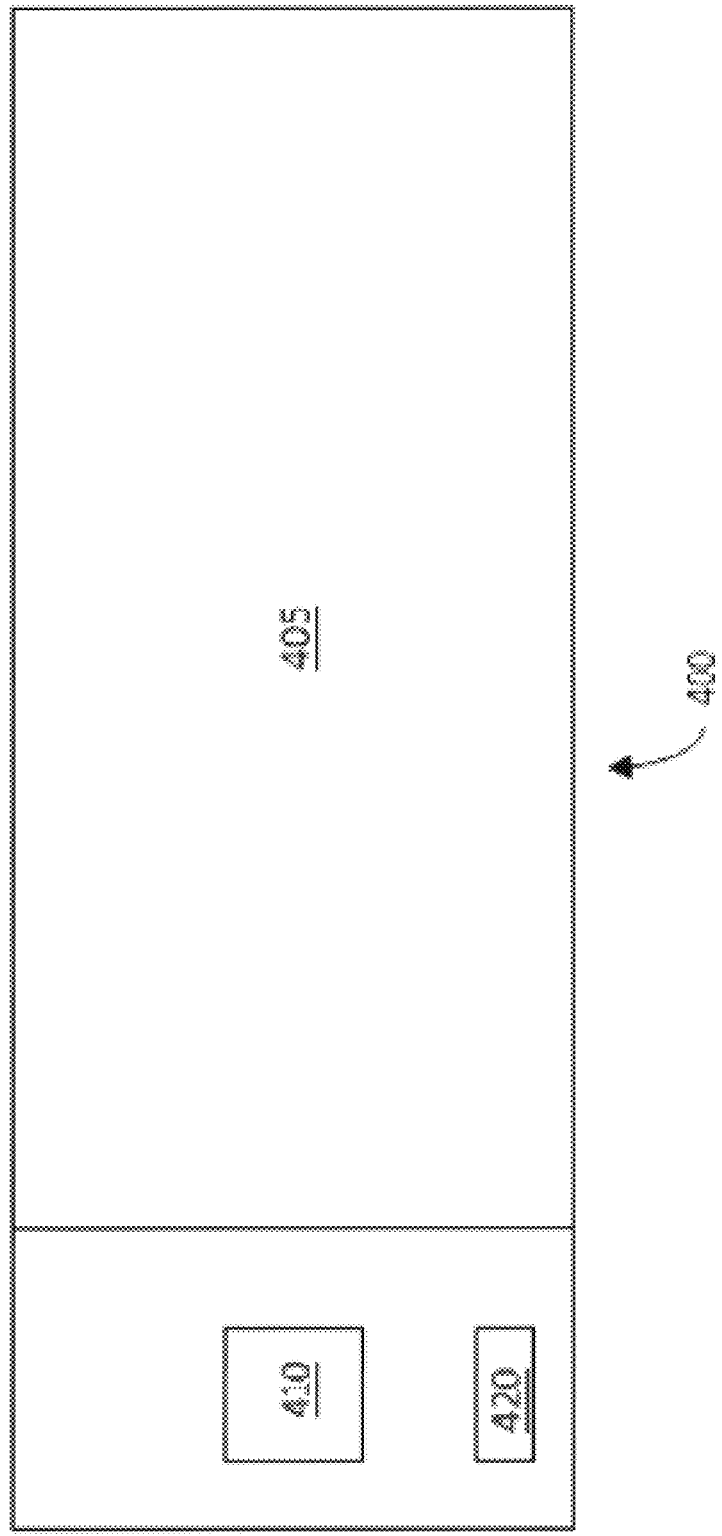
FIG. 18 to FIG. 20: each shows a slide with data processing capability, according to an example embodiment of the present invention.
Figure 19:
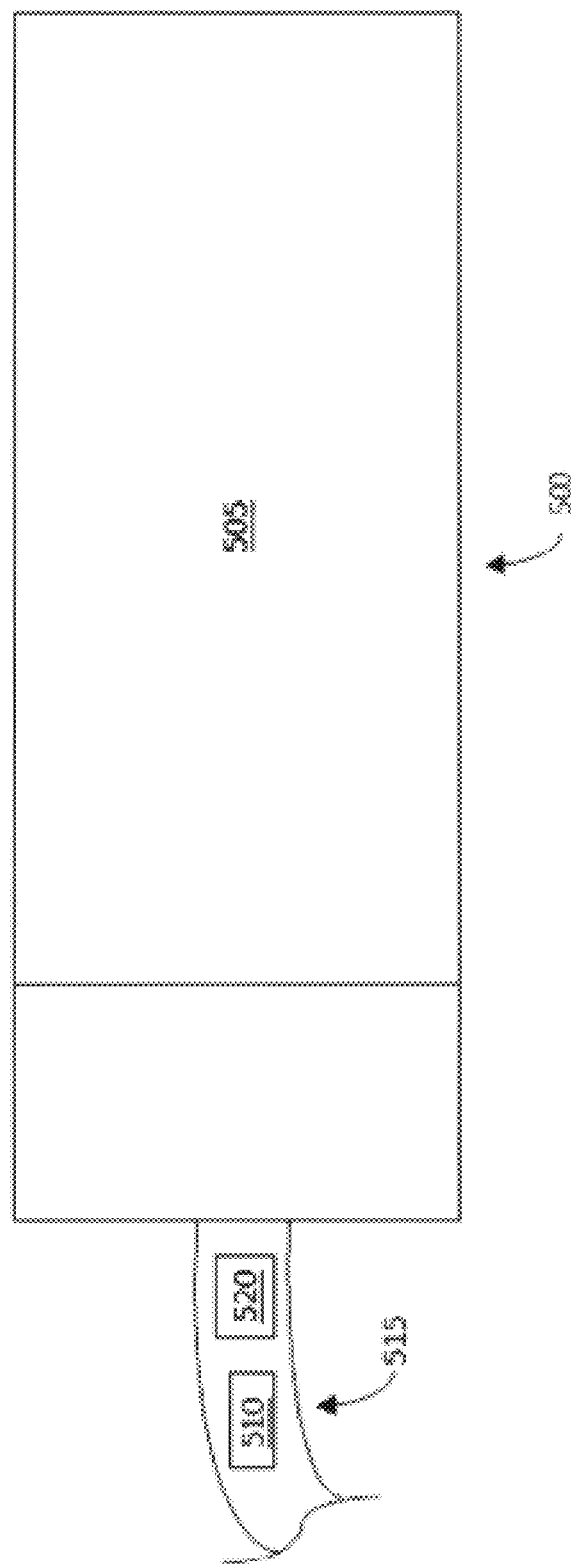
Figure 20:
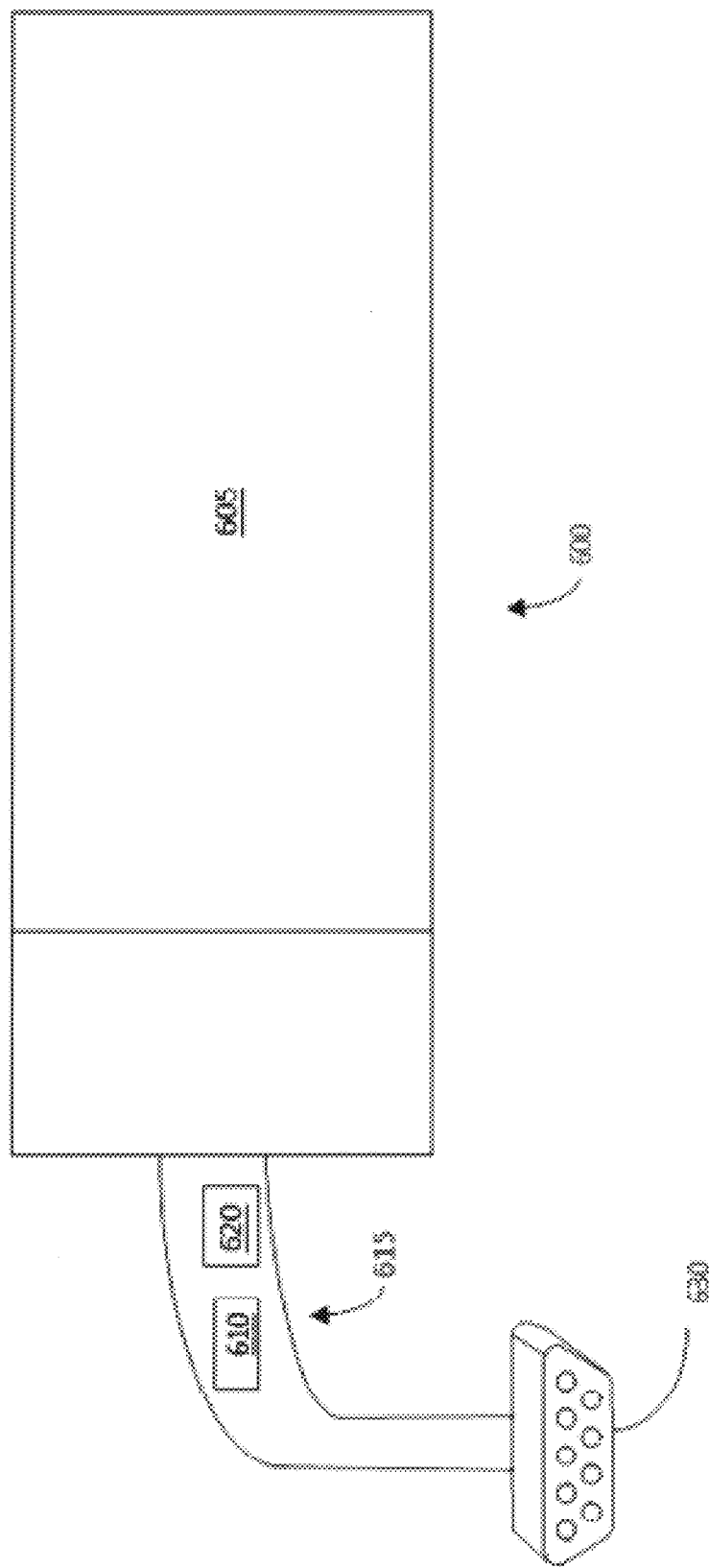

Example embodiments of the present invention relate to glass slides with at least some of the processing of measurement data being performed on the slide itself or on a peripheral device connected to a body of the slide, rather than at an external computer responsible for displaying the processed data. Such slides are referred to herein as an instrument-on-glass. FIG. 18 to FIG. 20 each shows an example embodiment of an instrument-on-glass.

FIG. 18 shows a slide 400 according to an example embodiment of the present invention. The slide 400 includes a pH measurement/modulation area 405, a power source 410 and a processing circuit 420. The area 405 can be formed of TFTs (for the switches) together with ITO (for the electrodes). Alternatively, the area 405 can be formed using only ITO or ITO in combination with other metals. The power source 410 can be analogous to the power source 14 in FIG. 14 and can be a battery or a passive power source powered, e.g., using magnetic or RF coupling.

The processing circuit 420 can be analogous to the control unit 12 in FIG. 14 and can perform preliminary signal processing. Additionally, the processing circuit 420 can perform some of the functions described earlier with respect to the data processing unit 50 (e.g., normalizing or scaling pH values or controlling pH modulation). The processing circuit 420 can include a processor (e.g., one or more CMOS chips) that processes the raw data obtained from area 405. The processing circuit 420 can further include a memory storing instructions or data, used by the processor to process the raw data. The processing circuit 420 can be configured to arrange the raw data into a suitable format for output to an external computer, or to perform preliminary data analysis (e.g., pH detection and invalidating data associated with particular pHs). The processor can control the sensing operation of the area 405 (e.g., driving and reading data out of the array), perform data compression, and perform wired or wireless transmission of the preliminarily processed data to an external computer. Post-processing and output of the data for display may be performed at the external computer.

FIG. 19 shows a slide 500 according to an example embodiment of the present invention. The components 505, 510 and 520 can be analogous to and perform the same functions as the components 405, 410 and 420, respectively, in FIG. 18. However, instead of being located on the body of the slide 500, the power source 510 and the processing circuit 520 are externally connected, e.g., on a peripheral circuit board 515 that fits into a hardware interface of the slide 500.

FIG. 20 shows a slide 600 according to an example embodiment of the present invention. The components 605, 610 and 620 can be analogous to and perform the same functions as the components 405, 410 and 420, respectively, in FIG. 18. In the embodiment of FIG. 20, the power source 610 and the processing circuit are externally connected, similar to FIG. 19. However, the circuit board 615 includes a serial port connector for transmission of data and power between the board 615 and the external computer. Specifically, the serial port may be used to transfer measurement data to the external computer, and to supply power for operating the measurement area 605 or for recharging the power source 610.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a non-transitory hardware computer-readable medium including any conventional memory device, to perform any of the methods described herein, alone or in combination, e.g., to output any one or more of the described graphical user interfaces. The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), flash memory, and magnetic tape.

An example embodiment of the present invention is directed to a non-transitory, hardware computer-readable medium, e.g., as described above, on which are stored instructions executable by a processor to perform any one or more of the methods described herein.

An example embodiment of the present invention is directed to a method, e.g., of a hardware component or machine, of transmitting instructions executable by a processor to perform any one or more of the methods described herein.

Example embodiments of the present invention are directed to one or more of the above-described devices and methods, e.g., computer-implemented methods, alone or in combination.

Example embodiments of the present invention provide devices and methods for using electronics to control the pH of a solution close to an electrode and a device for implementing the methods in an integrated electronic system. Preferably the devices and methods of the present invention are able to control the pH of the solution surrounding the electrode within a distance of about 1 cm. The devices and methods for using electronics to control the pH of a solution can also include detection of pH of the solution by the devices and methods described above and elsewhere herein. In some instances, the pH detection and the pH modulation are both performed by the same device and/or method.

According to an example embodiment, a method for changing the pH of a solution by electronic control includes providing an amount of electric input to the solution using three or more electrodes and a pH sensing element to electrochemically generate and/or consume hydrogen ions in the solution. The generation and/or consumption of the hydrogen ions are achieved by an electrochemical reaction of one or more redox active species in the solution. Preferably, the one or more redox active species is selected from the following: quinones, catechols, aminophenols hydrazines, and derivatives thereof. More preferably, the one or more redox active species is a quinone (See Thomas Finley, "Quinones," Kirk-Othmer Encyclopedia of Chemical Technology, 1-35 (2005)). Even more preferably, the one or more redox active species is selected from the following: hydroquinone, benzoquinone, naphthoquinonenaphthoquinone. Most preferably, the one or more redox active species is a quinone derivative, further defined below.

Preferably, the three or more electrodes comprise a counter electrode, a working electrode, and a reference electrode (RE). In some example embodiments, the sensing element can be a sensing electrode. In certain example embodiments of the present invention, a sense electrode can also function as a working electrode. In certain example embodiments of the present invention, the three or more electrodes are each independently made of metal oxide, gold, glassy carbon, graphene, silver, platinum, silver chloride, normal hydrogen, mercury drop, or saturated calomel. In certain example embodiments of the present invention, the solution is buffered, unbuffered, aqueous, organic, or a mixture thereof. In certain example embodiments of the present invention, the amount of electric input is provided by providing an amount of electric current. In certain example embodiments of the present invention, an electric source waveform is selected based on the amount of electric input to be provided. Preferably, the electric source waveform is a galvanostatic waveform or a potentiostatic waveform. More preferably, the electric source waveform is selected from a predetermined map that maps electric input amounts to respective solution pH values.

According to an example embodiment of the present invention, a method for controlling the pH of a solution using three or more electrodes includes obtaining the pH of the solution and/or the open circuit potential (OCP) of two or more electrodes in the solution while no electric input is being applied between the two or more electrodes, selecting an amount of electric input based on the pH and/or OCP, and providing the amount of electric input to the solution between the two or more electrodes to change the pH of the solution. In certain example embodiments of the present invention, the OCP is obtained by measuring the OCP of the two or more electrodes in the solution or calculated from a known or measured initial pH. In certain example embodiments of the present invention, the method also includes determining the pH of the solution based on the OCP of two or more electrodes in solution. In certain example embodiments of the present invention, the method also includes selecting an electric source waveform based on the amount of electric input and the amount of electric input is provided according to the selected electric source waveform.

In certain example embodiments of the present invention, the method further includes determining the pH of the solution based on a measured OCP of the two or more electrodes in the solution. In certain example embodiments of the present invention, the amount of electric input is selected based on the determined pH.

According to an example embodiment of the present invention, a method for monitoring the pH of a solution using a sensing element, a reference electrode, a counter electrode, and a working electrode includes selecting a target pH value and/or open circuit potential (OCP), characterizing a pH and/or OCP of the solution between the reference electrode and a sense electrode while no electric input is being applied to the working electrode, and iteratively performing the following steps: selecting an amount of electric input to be applied to the working electrode in order to minimize a difference between the pH and/or OCP of the solution and the target pH value and/or OCP; and applying the amount of electric input to the working electrode to adjust the pH and/or OCP of the solution.

In certain example embodiments of the present invention, the target pH value and/or OCP is a fixed value and in other example embodiments, the target pH value and/or OCP is a variable value. In certain example embodiments of the present invention, the target pH value and/or OCP is a range with an upper bound and a lower bound or is a single value. Preferably, the target OCP is selected based on a target pH value. Preferably, the target pH value is user defined. In some instances, the pH changes over time and/or is different for different working electrodes. In certain example embodiments of the present invention, a sense electrode can also function as a working electrode. In certain example embodiments of the present invention, a sense electrode and a working electrode are distinct electrodes. Preferably, the distance between the sense electrode and the working electrode is 0 cm to 1 cm. The electric input can be provided as an electric current or as an electric potential. Preferably, the amount of electric input is provided by applying an electric potential to the working electrode. More preferably, the electric potential is provided according to an electric source waveform. The electric source waveform is a galvanostatic waveform or a potentiostatic waveform. Even more preferably, the electric source waveform is selected from a predetermined map that maps electric input amounts to respective solution pH values. Preferably, a sensing element is a sense electrode that is coated with a pH sensitive coating and the OCP of the sense electrode and the pH sensitive coating is dominated by the $H^+$ ion concentration. In certain example embodiments of the present invention, the pH sensitive coating is an organic material. In other example embodiments of the present invention, the pH sensitive coating is an inorganic material. Preferably, the pH sensitive coating is made from a material that is selected from the group consisting of polyaniline, polypyrrole, and iridium oxide.

The example embodiments involve monitoring and/or characterizing electrochemical parameters and using a detected signal as a feedback control to generate a desired pH waveform for a specific length of time. All the described methods involve the use of a redox couple to release H+ ions, lowering pH, upon oxidation, and to consume H+ ions, increasing pH, upon reduction based on the formula:

$$RH_2 \rightleftharpoons R + 2H^+ + 2e^-$$

An example of a redox reaction is the reaction of quinone derivatives. There are many different derivatives of quinone, each with specific oxidative and reductive peaks and the redox reaction rate has been shown to be dependent on the pH of the solution. The electrochemical properties of an electrode, including the electron transfer coefficient and the open circuit potential (OCP) in relation to a reference electrode, are also properties that can be considered. OCP has been previously demonstrated to be dependent on the pH of the solution.

According to an example embodiment of the present invention, a device for controlling the pH of a solution includes a controller, three or more electrodes, and a solution containing one or more redox active species. In some embodiments, the device can be configured to measure the pH of the solution and/or the OCP between two or more electrodes in the solution to generate a measured OCP data and send the measured pH and/or OCP data to the controller. In some embodiments, the device can be configured to measure the pH of a solution by measuring fluorescence of a pH sensitive fluorescent molecule or molecules. In some embodiments, the device can be configured to measure the pH of a solution by use of a pH sensing electrode. In some embodiments, the device can be configured to measure the pH of a solution by measuring pH in any way known to the field. The controller can be configured to iteratively perform the following steps: select an amount of current or an electric source waveform based on a difference between the target pH value and/or OCP data and the measured pH and/or OCP data or the target output of the pH sensing element and the measured output of the pH sensing element, apply the selected amount of current to the solution by providing an electric current or an electric potential, according to the electric potential waveform, to one or more of the two or more electrodes, and send a request to the device for another measurement of the OCP and/or output of the pH sensing element.

Preferably, the one or more redox active species in the solution generates and/or consumes hydrogen ions through an electrochemical reaction induced by the electric current or the electric potential applied to the solution. Preferably, the one or more redox active species is selected from the following: quinone, catechol, aminophenol, hydrazine, and derivatives thereof. More preferably, the one or more redox active species is a quinone. (See, Thomas Finley, "Quinones," Kirk-Othmer Encyclopedia of Chemical Technology, 1-35 (2005)). Even more preferably, the quinone is selected from the following: hydroquinone, benzoquinone, naphthoquinone, and derivatives thereof. Most preferably the one or more redox active species is a quinone derivative. In certain example embodiments of the present invention, the solution is buffered, unbuffered aqueous, organic, or a mixture thereof. In certain example embodiments of the present invention, the electric source waveform is a galvanostatic waveform or a potentiostatic waveform. Preferably, the electric source waveform is selected from a predetermined map that maps electric inputs to respective solution pH values. In certain example embodiments of the present invention, the three or more electrodes are made of metal oxide, glassy carbon, graphene, gold, silver, or platinum. Preferably, the three or more electrodes include a reference electrode, a working electrode, and a counter electrode, and the sensing element is a sense electrode. Each of the three of more electrodes is respectively made of metal oxide, gold, glassy carbon, graphene, silver, platinum, silver chloride, normal hydrogen, mercury drop, or saturated calomel. In certain example embodiments of the present invention, the sense electrode can also function as a working electrode. Preferably, the sense electrode is coated with a pH sensitive coating and the OCP of the sense electrode and the pH sensitive coating is dominated by the H+ ion concentration. In certain example embodiments of the present invention, the pH sensitive coating is an organic or an inorganic material. Preferably, the pH sensitive coating is made from a material that is selected the group consisting of polyaniline, polypyrrole, and iridium oxide.

Also provided are quinone derivatives that can be added to solutions and are suitable for electrochemical pH modulation in biological buffers, electrochemically active compositions comprising the quinone derivatives, methods of making the derivatives and/or compositions, and uses thereof.

According to example embodiments, the electrochemically active composition comprises a quinone derivative, where the reactivity between a nucleophile and the quinone derivative is reduced compared to a reactivity between the nucleophile and an unsubstituted quinone from which the quinone derivative is derived, and the composition is configured such that the pH of the composition is electrochemically modulated via the quinone derivative. More preferably, the reactivity between the nucleophile and the quinone derivative is reduced by at least 50% compared to the reactivity between the nucleophile and the unsubstituted quinone from which the quinone derivative is derived. Preferably, the quinone derivative is defined by a chemical formula selected from the group consisting of:

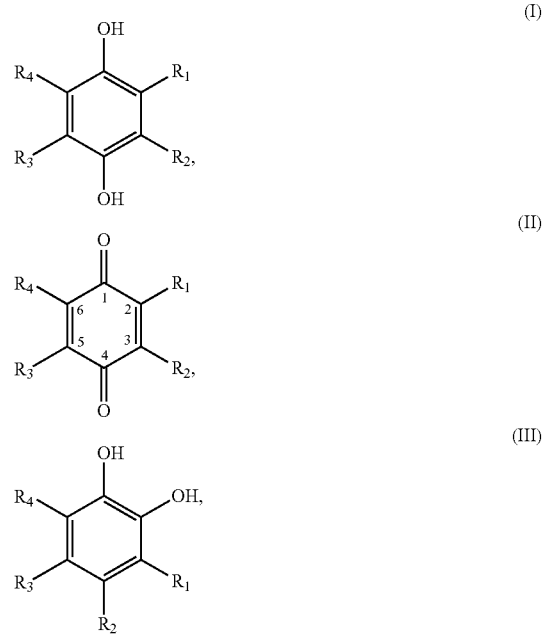

(IV) 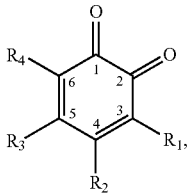

(V) 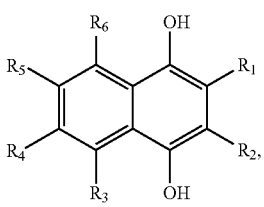

(VI) 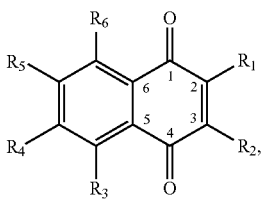

(VII) 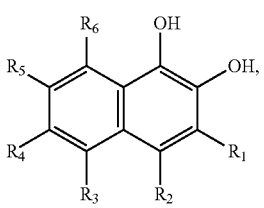

(VIII) 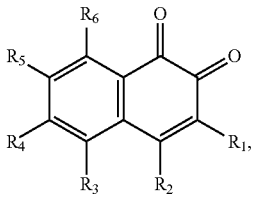

(IX) 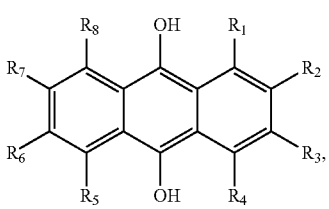

(X) 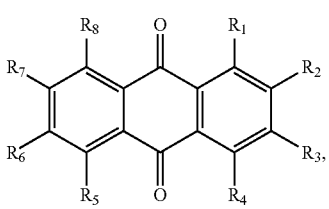

(XI) 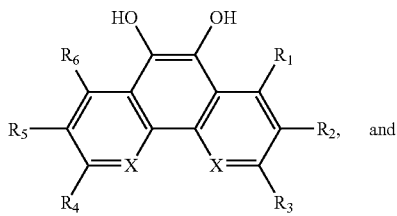

X = C or N (XII) 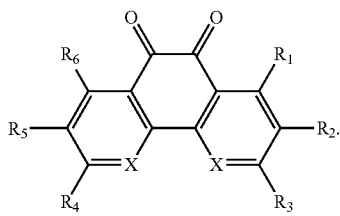

X = C or N

In the above chemical formulas I to XII, each R group is independently selected from the group consisting of: H; $C_nH_{2n+1}$; Cl; F; I; Br; OM; $NO_2$; OH; $OC_nH_{2n+1}$; $OC_nH_{2n}OH$; $O(C_nH_{2n}O)_yH$; $O(C_nH_{2n}O)_yC_nH_{2n+1}$; $O(C_nH_{2n}O)_yCOOH$; $O(C_nH_{2n}O)_yCOOM$; COOH; COOM; $COOC_nH_{2n+1}$; $CONHC_nH_{2n+1}$; $CON(C_nH_{2n+1})_2$; $SO_3H$; $SO_3M$; $NH_2$; $NHC_nH_{2n+1}$; $N(C_nH_{2n+1})_2$; $NHC_nH_{2n}OH$; $NHC_nH_{2n}NH_2$; $N(C_nH_{2n}OH)_2$; $N(C_nH_{2n}NH_2)_2$; $NHCOC_nH_{2n+1}$; $NC_nH_{2n}COC_nH_{2n+1}$; $NC_nH_{2n}COC_nH_{2n}OH$; $NC_nH_{2n}COC_nH_{2n}NH_2$; $NHC_nH_{2n}COC_nH_{2n}SH$; SH; $SC_nH_{2n+1}$; $SC_nH_{2n}OH$; $S(C_nH_{2n}O)_yH$; $S(C_nH_{2n}O)_yC_nH_{2n+1}$; $S(C_nH_{2n}O)_yCOOH$; $S(C_nH_{2n}O)_yCOOM$; $OC_nH_{2n}SH$; $O(C_nH_{2n}O)_yC_nH_{2n}SH$; $O(C_nH_{2n}O)_yC_nH_{2n}SC_nH_{2n+1}$; $C_nH_{2n}$; $C_nH_{2n}OC_nH_{2n+1}$; $C_nH_{2n}SC_nH_{2n+1}$; $C_nH_{2n}NHC_nH_{2n+1}$; $C_nH_{2n}N(C_nH_{2n+1})C_nH_{2n}$; $C_nH_{2n}OH$; $C_nH_{2n}OC_nH_{2n+1}$; $C_nH_{2n}OC_nH_{2n}OH$; $C_nH_{2n}O(C_nH_{2n}O)_yCOOH$; $C_nH_{2n}O(C_nH_{2n}O)_yCOM$; $C_nH_{2n}COOH$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NHC_nH_{2n}COC_nH_{2n}OH$; $C_nH_{2n}NHC_nH_{2n}CGC_nH_{2n}NH_2$; $C_nH_{2n}NHC_nH_{2n}CGC_nH_{2n}SH$; $C_nH_{2n}SH$; $C_nH_{2n}SC_nH_{2n+1}$; $C_nH_{2n}SC_nH_{2n}OH$; $C_nH_{2n}S(C_nH_{2n}O)_yH$; $C_nH_{2n}S(C_nH_{2n}O)_yC_nH_{2n+1}$; $C_nH_{2n}S(C_nH_{2n}O)_yC_nH_{2n}COOH$; $C_nH_{2n}S(C_nH_{2n}O)_yC_nH_{2n}COOM$; sugars; peptides; and amino acids; at least one of the R groups is not hydrogen; M is any metal cation or $NH_4^+$; n is an integer from 1 to $10^9$; and y is an integer from 1 to $10^9$.

According to example embodiments, all of the R groups of the quinone derivative are different from each other. According to example embodiments, two or more of the R groups of the quinone derivative are the same. Preferably, the composition is an aqueous solution. According to example embodiments, the composition further comprises an additive selected from the group consisting of: an aqueous buffer, an organic solvent, an electrolyte, a buffer salt, a bioreagent, a biomolecule, a surfactant, a preservative, a cryoprotectant, one or more reactants, a catalyst, an enzyme, a co-factor, etc. and combinations thereof. Preferably the one or more nucleophiles are selected from the group consisting of: amines, thiols, amino acids, peptides, proteins, and combinations thereof. According to example embodiments, the reactivity between the nucleophile and the quinone derivative is reduced compared to the reactivity between the nucleophile and the unsubstituted quinone from which the quinone derivative is derived due to: (i) increased steric hindrance of a nucleophile binding site by one or more of the R groups; (ii) elimination of the nucleophile binding site by covalent bonding between the nucleophile binding site and one of the R groups. Preferably the reactivity between the nucleophile and the quinone derivative is reduced compared to the reactivity between the nucleophile and the unsubstituted quinone from which the quinone derivative is derived due both (i) and (ii).

Also provided are methods comprising modifying a quinone having one or more R groups by substituting one or more of the R groups with a substituent to provide a quinone derivative, where the quinone derivative has a reduced reactivity with a nucleophile compared to a reactivity between the quinone and the nucleophile; and the substituent is independently selected from the group consisting of: H; $C_nH_{2n+1}$; Cl; F; I; Br; OM; $NO_2$; OH; $OC_nH_{2n+1}$; $OC_nH_{2n}OH$; $O(C_nH_{2n}O)_yH$; $O(C_nH_{2n}O)_yC_nH_{2n+1}$; $O(C_nH_{2n}O)_yCOOH$; $O(C_nH_{2n}O)_yCOOM$; COOH; COOM; $COOC_nH_{2n+1}$; $CONHC_nH_{2n+1}$; $CON(C_nH_{2n+1})_2$; $SO_3H$; $SO_3M$; $N_2$; $NHC_nH_{2n+1}$; $N(C_nH_{2n+1})_2$; $NHC_nH_{2n}OH$; $NHC_nH_{2n}NH_2$; $N(C_nH_{2n}OH)_2$; $N(C_nH_{2n}NH_2)_2$; $NHCOC_nH_{2n+1}$; $NC_nH_{2n}COC_nH_{2n+1}$; $NC_nH_{2n}COC_nH_{2n}OH$; $NC_nH_{2n}COC_nH_{2n}NH_2$; $NHC_nH_{2n}COC_nH_{2n}SH$; SH; $SC_nH_{2n+1}$; $SC_nH_{2n}OH$; $S(C_nH_{2n}O)_yH$; $S(C_nH_{2n}O)_yC_nH_{2n+1}$; $S(C_nH_{2n}O)_yCOOH$; $S(C_nH_{2n}O)_yCOOM$; $OC_nH_{2n}SH$; $O(C_nH_{2n}O)_yC_nH_{2n}SH$; $O(C_nH_{2n}O)_yC_nH_{2n}SC_nH_{2n+1}$; $C_nH_{2n}$; $C_nH_{2n}OC_nH_{2n+1}$; $C_nH_{2n}SC_nH_{2n+1}$; $C_nH_{2n}NHC_nH_{2n+1}$; $C_nH_{2n}N(C_nH_{2n+1})C_nH_{2n}$; $C_nH_{2n}OH$; $C_nH_{2n}OC_nH_{2n+1}$; $C_nH_{2n}OC_nH_{2n}OH$; $C_nH_{2n}O(C_nH_{2n}O)_yCOOH$; $C_nH_{2n}O(C_nH_{2n}O)_yCOOM$; $C_nH_{2n}COOH$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NHC_nH_{2n}COC_nH_{2n}OH$; $C_nH_{2n}NHC_nH_{2n}COC_nH_{2n}NH_2$; $C_nH_{2n}NHC_nH_{2n}COC_nH_{2n}SH$; $C_nH_{2n}SH$; $C_nH_{2n}SC_nH_{2n+1}$; $C_nH_{2n}SC_nH_{2n}OH$; $C_nH_{2n}S(C_nH_{2n}O)_yH$; $C_nH_{2n}S(C_nH_{2n}O)_yC_nH_{2n+1}$; $C_nH_{2n}S(C_nH_{2n}O)_yC_nH_{2n}COOH$; $C_nH_{2n}S(C_nH_{2n}O)_yC_nH_{2n}COOM$; sugars; peptides; and amino acids; M is any metal cation or $NH_4^+$; n is an integer from 1 to $10^9$; and y is an integer from 1 to $10^9$. According to example embodiments, the one or more R groups are substituted with a polar group. Preferably the polar group has atoms containing lone pair electrons. Preferably, the polar group is capable of forming hydrogen bonds with water. Preferably, the polar group contains at least one of oxygen, nitrogen, and sulfur atoms. More preferably, the polar group is selected from the group consisting of: OH, $CH_2OH$, $OCH_3$, COOH, $SO_3H$, $NH_2$, $NH_3Cl$, ONa, a sugar, an amino acid, and a peptide.

Also provided are methods of synthesizing substituted methyl quinone comprising: (i) a halide substitution step of reacting a starting material with a hydrogen halide in the presence of acetic acid and an aldehyde; (ii) reacting a material produced by step (i) with a nucleophile of structure R—X; (iii) reacting a material produced by step (ii) with an oxidizing agent; and (iv) reacting a material produced by step (iii) with a reducing agent, where R is selected from the group consisting of: H; $C_nH_{2n+1}$; Cl; F; I; Br; OM; $NO_2$; OH; $OC_nH_{2n+1}$; $OC_nH_{2n}OH$; $O(C_nH_{2n}O)_yH$; $O(C_nH_{2n}O)_yC_nH_{2n+1}$; $O(C_nH_{2n}O)_yCOOH$; $O(C_nH_{2n}O)_yCOOM$; COOH; COOM; $COOC_nH_{2n+1}$; $CONHC_nH_{2n+1}$; $CON(C_nH_{2n+1})_2$; $SO_3H$; $SO_3M$; $NH_2$; $NHC_nH_{2n+1}$; $N(C_nH_{2n+1})_2$; $NHC_nH_{2n}OH$; $NHC_nH_{2n}NH_2$; $N(C_nH_{2n}OH)_2$; $N(C_nH_{2n}NH_2)_2$; $NHCOC_nH_{2n+1}$; $NC_nH_{2n}COC_nH_{2n+1}$; $NC_nH_{2n}COC_nH_{2n}OH$; $NC_nH_{2n}COC_nH_{2n}NH_2$; $NHC_nH_{2n}COC_nH_{2n}SH$; SH; $SC_nH_{2n+1}$; $SC_nH_{2n}OH$; $S(C_nH_{2n}O)_yH$; $S(C_nH_{2n}O)_yC_nH_{2n+1}$; $S(C_nH_{2n}O)_yCOOH$; $S(C_nH_{2n}O)_yCOOM$; $OC_nH_{2n}SH$; $O(C_nH_{2n}O)_yC_nH_{2n}SH$; $O(C_nH_{2n}O)_yC_nH_{2n}SC_nH_{2n+1}$; $C_nH_{2n}$; $C_nH_{2n}OC_nH_{2n+1}$; $C_nH_{2n}SC_nH_{2n+1}$; $C_nH_{2n}NHC_nH_{2n+1}$; $C_nH_{2n}N(C_nH_{2n+1})C_nH_{2n}$; $C_nH_{2n}OH$; $C_nH_{2n}OC_nH_{2n+1}$; $C_nH_{2n}OC_nH_{2n}OH$; $C_nH_{2n}O(C_nH_{2n}O)_yCOOH$; $C_nH_{2n}O(C_nH_{2n}O)_yCOOM$; $C_nH_{2n}COOH$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NHC_nH_{2n}COC_nH_{2n}OH$; $C_nH_{2n}NHC_nH_{2n}COC_nH_{2n}NH_2$; $C_nH_{2n}NHC_nH_{2n}COC_nH_{2n}SH$; $C_nH_{2n}SH$; $C_nH_{2n}SC_nH_{2n+1}$; $C_nH_{2n}SC_nH_{2n}OH$; $C_nH_{2n}S(C_nH_{2n}O)_yH$; $C_nH_{2n}S(C_nH_{2n}O)_yC_nH_{2n+1}$; $C_nH_{2n}S(C_nH_{2n}O)_yC_nH_{2n}COOH$; $C_nH_{2n}S(C_nH_{2n}O)_yC_nH_{2n}COOM$; sugars; peptides; and amino acids; M is any metal cation or $NH_4^+$; n is an integer from 1 to $10^9$; y is an integer from 1 to $10^9$; and X is either OH, $NH_2$, NHR, SH, $O^-$, or $S^-$.

According to example embodiments, the starting material is dialkoxybenzene and the result of the halide substitution step is an ortho-quinon, para-quinone, or a combination thereof. Preferably, the number of halide groups per molecule of the ortho-quinone or para-quinone is 1, 2, 3, or 4. According to example embodiments, the starting material is dialkoxynaphthalene and the result of the halide substitution step is an ortho-naphthoquinone, para-naphthoquinone, or a combination thereof. Preferably, the number of halide groups per molecule of the ortho-naphthoquinone or para-naphthoquinone is 1 or 2. Preferably, the hydrogen halide is selected from the group consisting of: HCl, HBr, HI, and combinations thereof. Preferably, the oxidizing agent is selected from the group consisting of: cerium ammonium nitrate, iodine, hydrogen peroxide, hypervalent iodine, iodobenzene diacetate, bromine compounds, and combinations thereof. Preferably, the reducing agent is selected from the group consisting of: sodium borohydrate, potassium borohydrate, sodium hydrosulfite, trichlorosilane, and combinations thereof.

Also provided are methods comprising: providing a biosensor comprising a support in an solution, the support comprising one or more electrodes and a biomolecule interface layer having one or more immobilized probes thereon, and the solution comprising a quinone derivative; adding a biomolecule analyte to the solution; electrochemically reacting the quinone derivative using the one or more electrodes to produce an amount of $H^+$ ions and/or an amount of $OH^-$ ions, wherein the pH of the solution close to the one or more electrodes is controlled by the amount of $H^+$ ions and/or the amount of $OH^-$ ions produced; collecting signals from the biosensor, where a reactivity between a nucleophile and the quinone derivative is reduced compared to a reactivity between the nucleophile and an unsubstituted quinone from which the quinone derivative is derived Preferably, the pH of the solution before electrochemically reacting the quinone derivative using the one or more electrodes is 1 to 14. Preferably, the pH of the solution after electrochemically reacting the quinone derivative using the one or more electrodes is 1 to 14. Preferably, the solution contains one or more nucleophiles. Preferably, the one or more nucleophiles are selected from the group consisting of: amines, thiols, amino acids, peptides, proteins, and combinations thereof. According to example embodiments, the solution contains a reduced quinone derivative and electrochemically reacting the quinone derivative results in an electrochemical oxidation reaction of the reduced quinone derivative to make the pH of the solution more acidic. Preferably, the concentration of the reduced quinone derivative is 0 to 1M. According to example embodiments, the solution contains an oxidized quinone derivative and electrochemically reacting the quinone derivative results in an electrochemical reduction reaction of the oxidized quinone derivative to make the pH of the solution more basic. Preferably, the concentration of the oxidized quinone derivative is 0 to 1M. Preferably, the solution contains one or more buffer components provided in a concentration that is 0 to 1M. Preferably, the one or more buffer components are selected from the group consisting of: organic solvents, electrolytes, bioreagents, biomolecules, surfactants, and combinations thereof. According to example embodiments, the method further comprises measuring the pH of the solution. Preferably, the pH is measured continuously. Preferably, the quinone derivative is electrochemically reacted by providing an amount of electric current. Preferably, the pH is measured before providing the amount of electric current. Preferably, the amount of electric current is selected based on the measured pH.

Quinones are herein defined as unsubstituted quinones. For example, the chemical structures I-XII would represent quinones if all of the R groups were hydrogen. Quinone derivatives are herein defined as compounds that are structurally similar to quinones except that at least one hydrogen is replaced by a substituent. In cases where more than one hydrogen is replaced by a substituent, the identity of the substituents may be independently selected but are not required to be unique. Compared to their unsubstituted counterparts the quinone derivatives of the present invention have reduced reactivity with nucleophiles and the pH of the biological buffer containing the quinone derivatives is able to be electrochemically modulated.

Also provided are methods for controlling a pH of a solution using three or more electrodes and a pH sensing element that can be a sensing electrode, the method comprising measuring a pH of the solution and/or open circuit potential (OCP) of two or more electrodes in the solution while no current is being applied between the two or more electrodes, selecting an amount of current based on the measured pH and/or OCP, and providing the selected amount of current to the solution, thereby changing the pH of the solution by at least one electrochemically generating or consuming hydrogen ions. Preferably, generation and/or consumption of the hydrogen ions are achieved by an electrochemical reaction of one or more redox active species in the solution. Preferably, the one or more redox active species is selected from the group consisting of: quinones, catechols, aminophenols, hydrazines, derivatives thereof, and combinations thereof. Preferably, the one or more redox active species is a quinone selected from the following: hydroquinone, benzoquinone, naphthaquinone, derivatives thereof, and combinations thereof. Preferably, the three or more electrodes comprise a counter electrode, a working electrode, and a reference electrode, and preferably a pH sensing electrode. According to example embodiments, the sense electrode is configured to also function as a working electrode. Preferably, the three or more electrodes are each independently made of a material selected from the group consisting of: metal oxide, gold, glassy carbon, graphene, silver, platinum, silver chloride, normal hydrogen, mercury drop, saturated calomel, and combinations thereof. Preferably, the solution is buffered, unbuffered, aqueous, organic, or a mixture thereof. Preferably, the method further comprises determining the pH of the solution based on the measured OCP of the two or more electrodes in the solution. Preferably, selection of an electrical waveform is based on the determined pH. Preferably, the method further comprises selecting an electrical waveform and providing the electrical waveform to the solution. The electrical waveform is either a galvanostatic waveform or a potentiostatic waveform. Preferably, the electrical waveform is selected from a predetermined map that maps respective current amounts to respective electrical waveforms.

Also provided is a biosensor system comprising a support that includes an a pH sensing element, a counter electrode, a reference electrode, and a working electrode; an electrochemically active agent, wherein the biosensor is configured to control a change of a redox state of the electrochemically active agent, and the biosensor is configured to iteratively perform the following: selecting an amount of current to be applied to the working electrode in order to minimize a difference between the pH and/or OCP of the solution and the target pH value and/or OCP; applying the selected amount of current to the working electrode to adjust the pH and/or OCP of the solution; and measuring the pH and/or OCP of the solution. Preferably, the solution is an aqueous solution. Preferably, the pH sensing element is a sense electrode. According to example embodiments, a sense electrode can also function as a working electrode. According to example embodiments, a sense electrode and the working electrode are distinct electrodes and a distance between the sense electrode and the working electrode is 0 cm to 1 cm. Preferably, the amount of current applied to the working electrode is provided by applying an electrical waveform. The electrical waveform is a galvanostatic waveform or a potentiostatic waveform. Preferably, the electrical waveform is selected from a predetermined map that maps respective current amounts to respective electrical waveforms. Preferably, a sense electrode is coated with a pH sensitive coating. The pH sensitive coating is an organic material or an inorganic material. Preferably, the pH sensitive coating is made from a material selected from the group consisting of: polyaniline, polypyrrole, iridium oxide, and a combination thereof.

Also provided are methods for monitoring pH of a solution using a sensing element, a counter electrode, a reference electrode, and a working electrode, the method comprising selecting a target pH value and/or an open circuit potential (OCP) based on a target pH value for the solution; determining the pH using a sensing element and/or characterizing an OCP of the solution between the reference electrode and a sense electrode while no current is being applied to the working electrode; and iteratively performing the following: selecting an amount of current to be applied to the working electrode in order to minimize a difference between the OCP and/or pH of the solution and the target OCP and/or pH; applying the selected amount of current to the working electrode to adjust the OCP and/or pH of the solution; and measuring the OCP and/or pH of the solution. Preferably, the solution is an aqueous solution. Preferably, the target pH value is set by incorporating an electro-chemical delta-sigma-modulator. The target pH value can be changed over time and/or be different between different working electrodes. More preferably, the output-signal of the electrochemical delta-sigma-modulator is digitally filtered to get a digital representation of the charge needed to create the target pH value. Preferably, the target pH value and/or OCP is a range with an upper bound and a lower bound. More preferably, the target pH value is a single target value. According to example embodiments, a sense electrode can also functions as a working electrode. According to example embodiments, the sense electrode and the working electrode are distinct electrodes and a distance between the sense electrode and the working electrode is 0 cm to 1 cm. Preferably, the amount of current applied to the working electrode is provided by applying an electrical waveform. The electrical waveform is a galvanostatic waveform or a potentiostatic waveform. Preferably, the electrical waveform is selected from a predetermined map that maps respective current amounts to respective electrical waveforms. Preferably, the sense electrode is coated with a pH sensitive coating. The pH sensitive coating is an organic material or an inorganic material. Preferably, the pH sensitive coating is made from a material selected from the group consisting of: polyaniline, polypyrrole, iridium oxide, and combinations thereof.

Also provided is a device for controlling a pH of a solution comprising: a controller; three or more electrodes; a pH sensing element; and a solution containing one or more redox active species, wherein the device is configured to iteratively perform the following: measure a pH and/or an open circuit potential (OCP) between two or more electrodes in the solution to generate a measured pH and/or OCP data; select, using the controller, an amount of current or an electric potential waveform based on a difference between target pH value and/or OCP data and the measured pH and/or OCP data; and apply, using the controller, the selected amount of current or the selected electric potential waveform to the solution via one or more of the three or more electrodes. Preferably, the solution is an aqueous solution. Preferably, the one or more redox active species generates or consumes hydrogen ions through an electrochemical reaction induced by the electric current or the electric potential applied to the solution. Preferably, the one or more redox active species is selected from the following: quinones, catechols, aminophenols hydrazines, derivatives thereof, and combinations thereof. Preferably, the one or more redox active species is a quinone selected from the following: hydroquinone, benzoquinone, naphthaquinone, derivatives thereof, and combinations thereof. Preferably, the solution is buffered, unbuffered aqueous, organic, or a mixture thereof. Preferably, the electric potential waveform is a galvanostatic waveform or a potentiostatic waveform. More preferably, the electric potential waveform is selected from a predetermined map that maps respective current amounts to respective electric potential waveforms. Preferably, the three or more electrodes comprise a reference electrode, working electrode, and a counter electrode, and the pH sensing element is a sense electrode. The three or more electrodes are made of a material independently selected from the group consisting of: metal oxide, gold, glassy carbon, graphene, silver, platinum, silver chloride, normal hydrogen, mercury drop, saturated calomel, and combinations thereof. According to example embodiments, a sense electrode can also function as a working electrode. Preferably, the sense electrode is coated with a pH sensitive coating. The pH sensitive coating is an organic material or an inorganic material. Preferably, the pH sensitive coating is made from a material selected from the group consisting of: polyaniline, polypyrrole, iridium oxide, and combinations thereof.

Figure 21:
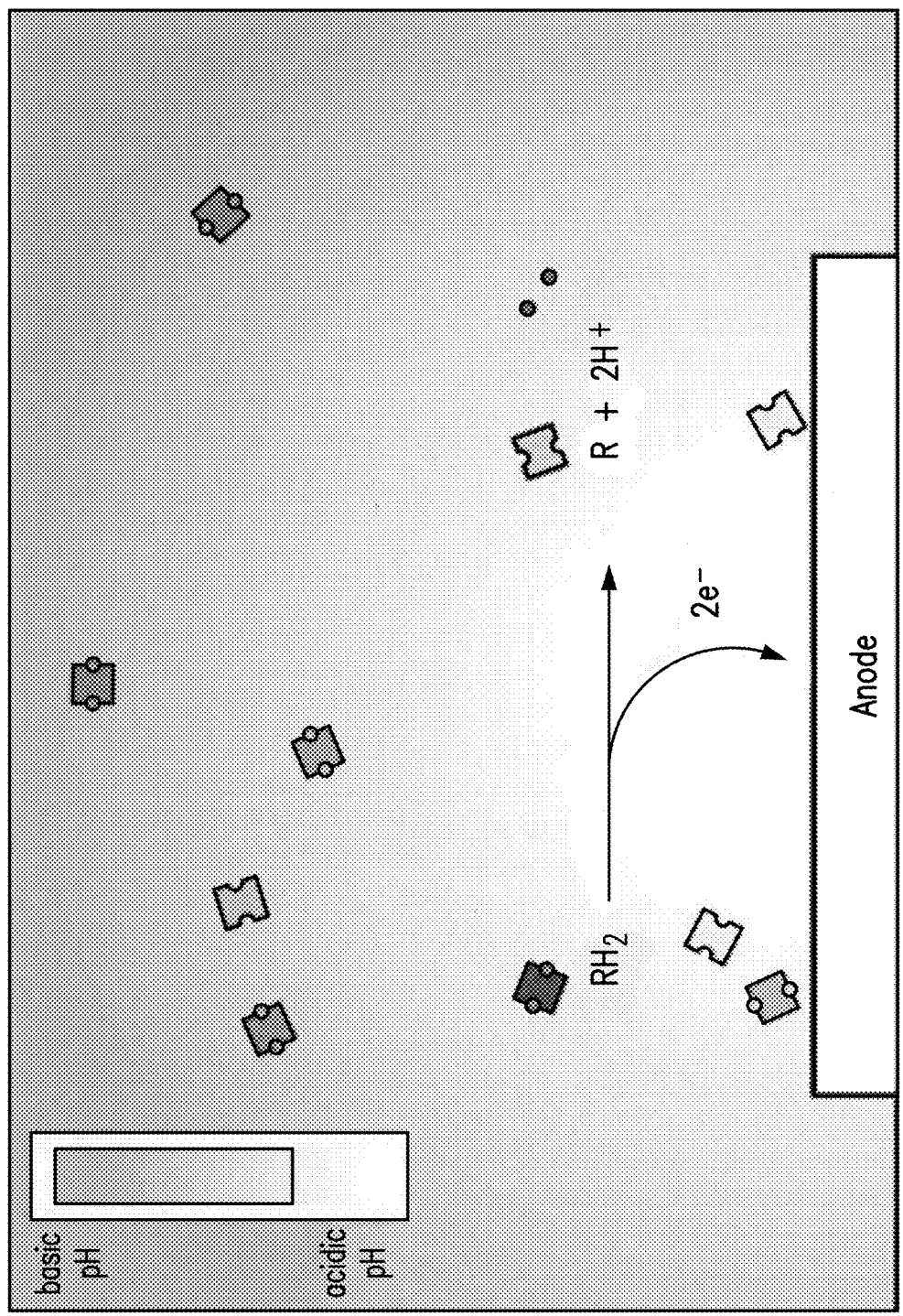
FIG. 21: shows a graphic representation of a system for electrochemical pH generation comprising a biological buffer with an electrochemically active agent dissolved in bulk solution over an electrode, where the change in pH is confined to the vicinity of the electrode surface through the buffering action of bulk solution, according to an example embodiment of the present invention.

A drawing of a system having electrochemically active agent in solution, according to an example embodiment of the present invention, is presented in FIG. 21. In previously described systems, the electrochemically active agent was attached to the electrode surface and not in solution. As shown in FIG. 21, the system can provide an anode electrode and an electrochemically active agent in solution. Applying a current to the electrode induces the electrochemically active agent to undergo an electrochemical redox reaction which makes the pH of the solution near the electrode more acidic. Having the electrochemically active agent in solution rather than attached to the electrode surface has many advantages. For example, a more significant change can be inflicted on the surrounding environment if the amount of electrochemically active agent is not limited by the density of the surface layer, thereby increasing capacity of the device; fresh electrochemically active agent can be supplied to the electrode surface via diffusion from bulk solution, thereby allowing for cycling capability; and universal electrochemistry can be applied to all types of electrodes, which will not interfere with other surface chemistries such as attachment of anti-fouling reagents or biomolecules. Furthermore, in order to make use of quinones as electrochemically active agents for pH generation in biological solutions, the structure of the quinones can be modified to satisfy the requirements for use in biological solutions. In order to be useful for pH modulation in biological buffers, a molecule should satisfy the following requirements: release or consume protons through electrochemical reaction upon electronic stimulation, sufficient water solubility, reduction and oxidation potential should be lower than the potential of water hydrolysis or other redox active species within the solution, stability in solution in the absence of electronic stimulation (i.e., no autooxidation/reduction), low reactivity towards nucleophiles, compatibility with biological samples (for example: proteins, peptides, cells, DNA, and enzymes).

FIG. 22 shows quinone derivatives that can be used for pH modulation in aqueous solutions, according to example embodiments of the present invention.

The above description is intended to be illustrative, and not restrictive. Those skilled in the art can appreciate from the foregoing description that the present invention may be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and appendices. Further, steps illustrated in the flowcharts may be omitted and/or certain step sequences may be altered, and, in certain instances multiple illustrated steps may be simultaneously performed.

The following are examples which illustrate specific methods without the intention to be limiting in any manner. The examples may be modified within the scope of the description as would be understood from the prevailing knowledge.

EXAMPLES

Example 1—Electrochemical Generation of H+ or OH− Ions at Electrode Surfaces

Electrode material used: The electrode material was indium tin oxide. This is a semiconducting electrode surface with very large potential window in an aqueous solution.

Electro-Oxidation of Species to Produce H+ Ions.

Figure 7A:
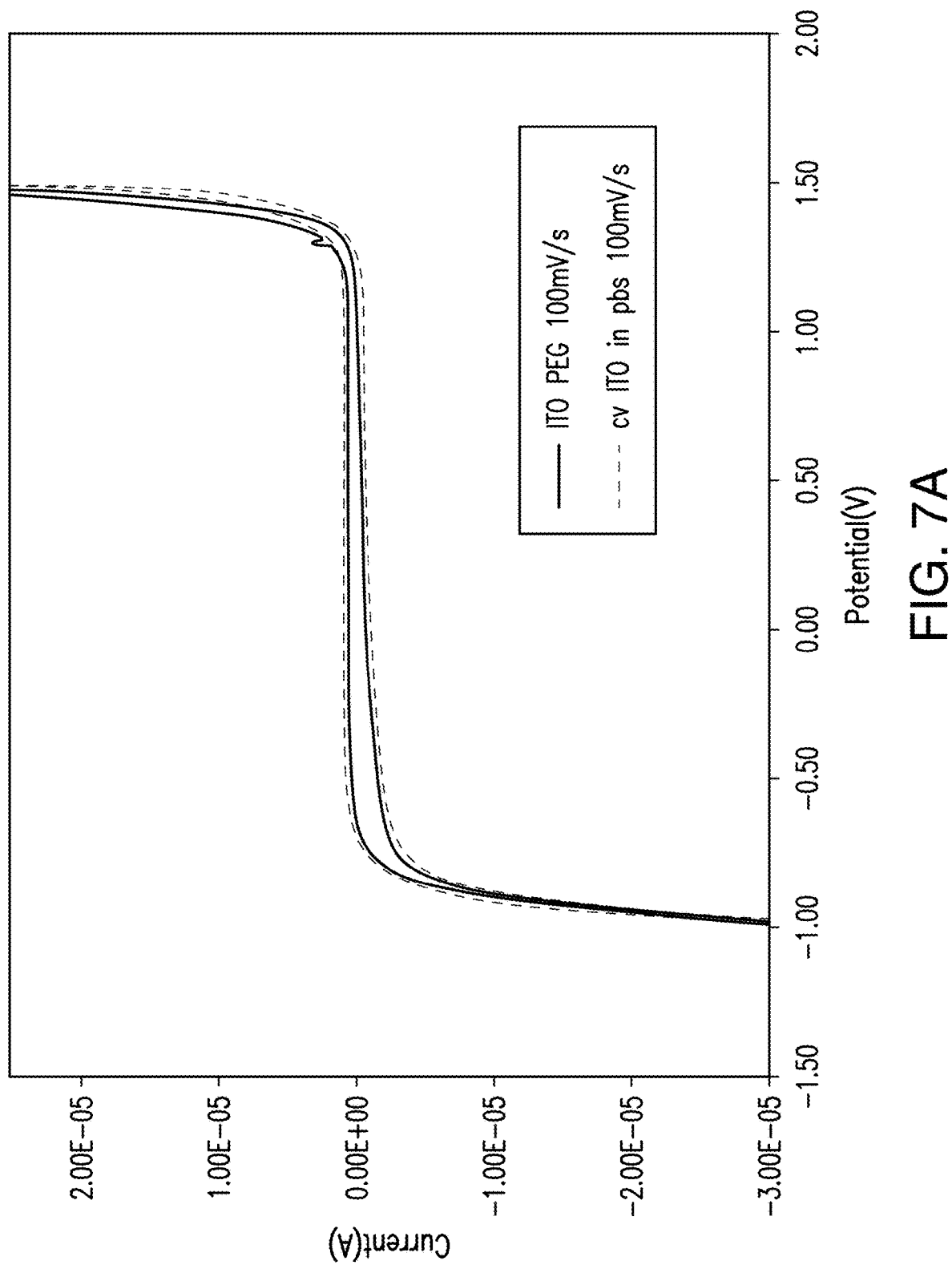
FIG. 7A: Cyclic voltammograms of Indium Tin Oxide (ITO) electrodes in PBS only. The region where pH change can occur is where there is oxygen evolution more than 1V in respect to Ag/AgCl reference electrode.
Figure 7B:
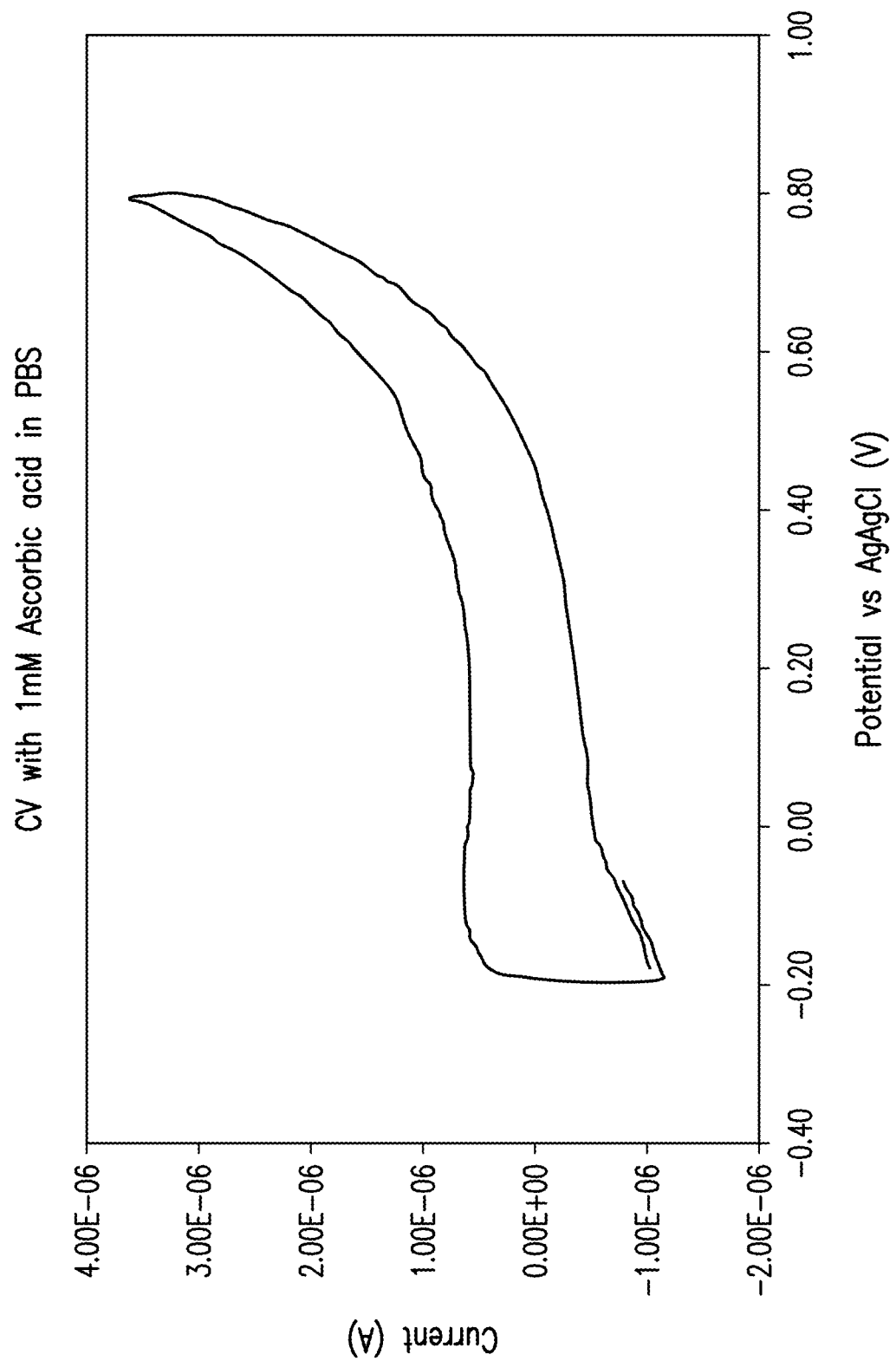
FIG. 7B: Cyclic voltammetric study of the oxidation of Ascorbic acid test in ITO electrodes. Current increase around 0.25V indicates the start of oxidation at ITO electrodes.
Figure 8A:
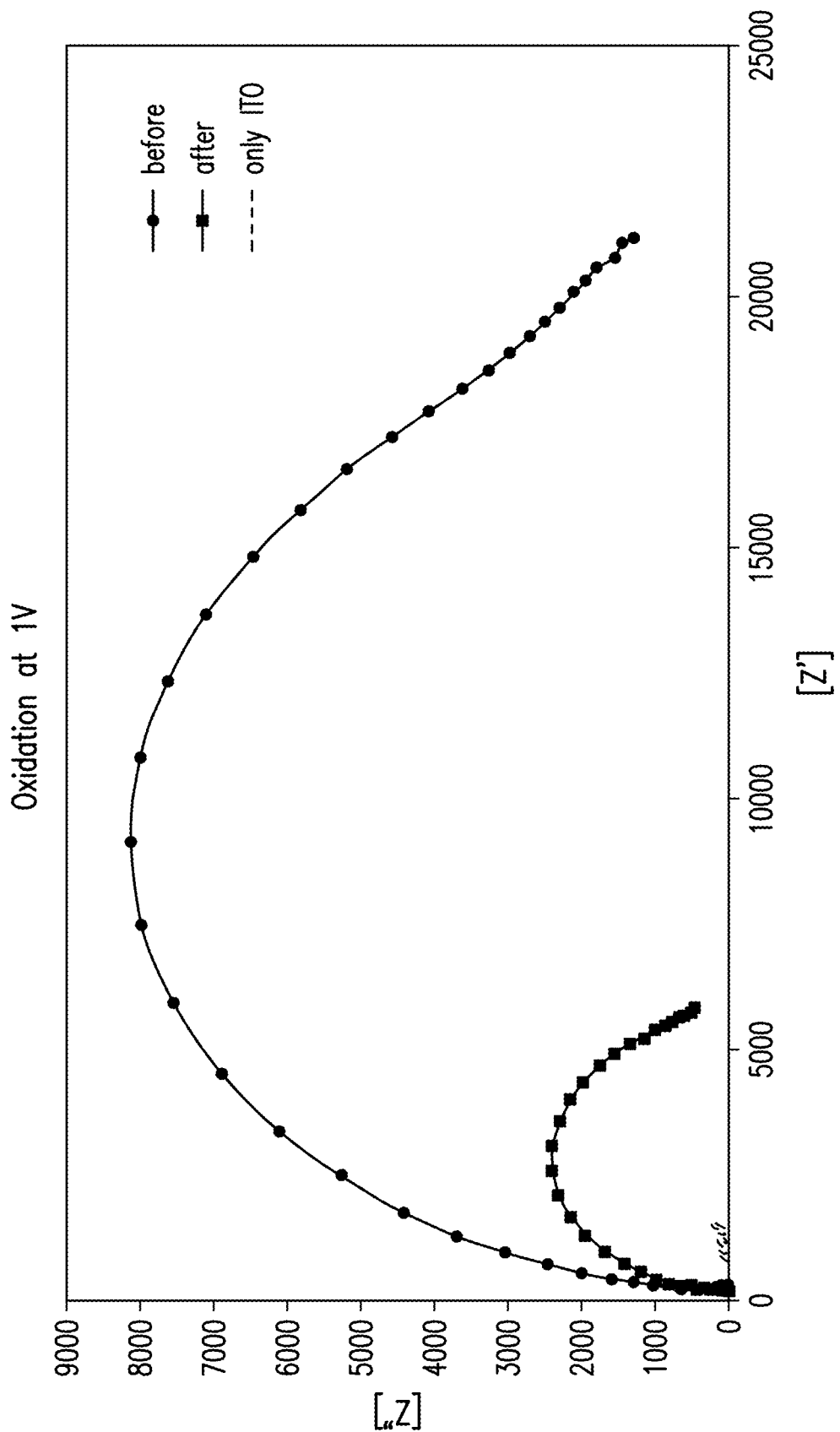
FIG. 8A: Application of 1V on the ITO-PEG surface in Phosphate buffer. Impedance changes before and after application of 1V indicates the changes or removal of PEG from electrode.
Figure 8B:
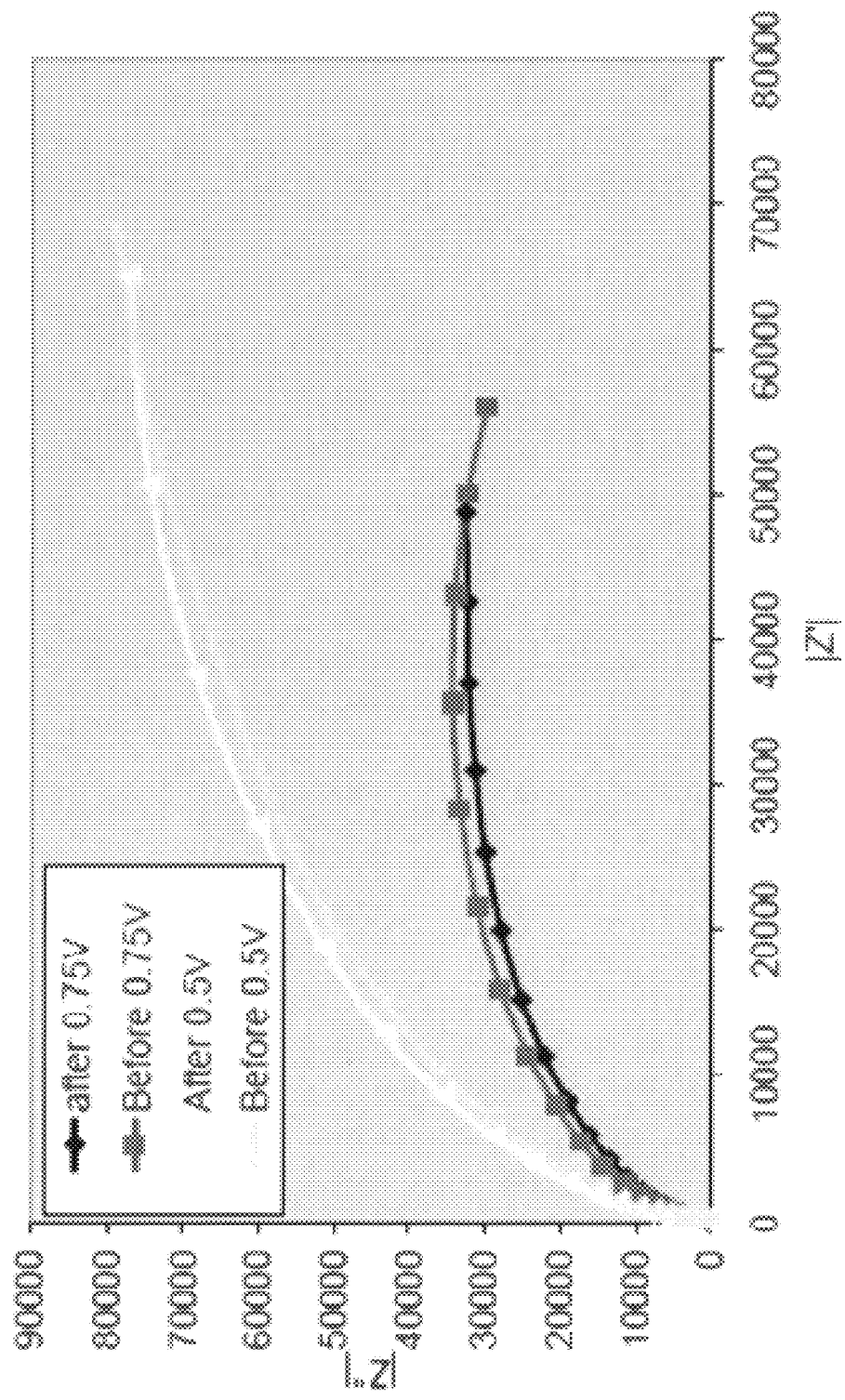
FIG. 8B: Oxidation of ascorbic acid at 0.5V and 0.75V at ITO-PEG surface. No change in impedance during ascorbic acid oxidation indicates PEG layers do not undergo any change.

Oxidation of ascorbic acid at the electrode surfaces produced H+ ions and changed the electrode surface pH to a more acidic state:

$$AH_2 \rightarrow A + 2H^+ + 2e^-,$$

where $AH_2$ is ascorbic acid ($C_6H_6O_6$) (as shown in FIG. 5). The electrode potential at which it oxidizes was less than 0.5V for Indium tin oxide material vs Ag/AgCl reference electrode (as shown in FIG. 7). This potential was less than the voltages needed for the oxygen evolution reaction in aqueous solution. Higher electrode potential (e.g. >1V for ITO electrodes in just phosphate buffer) can damage the PEG layer (as shown in FIG. 8). The ascorbic acid also acted as a sacrificial species to prevent electrochemical degradation of the surface chemistry.

Electro-Reduction of Species to Produce OH− Ions.

Reduction of benzoquinone ($C_6H_4O_2$) into Hydroquinone ($C_6H_6O_2$) can produce OH− ions at −0.1V:

$$BQ + 2e^- + 2H_2O \rightarrow HQ + 2OH^-$$

This reduction reaction increased the pH at the electrode interface.

In the above examples the amount of H+ or OH− ions generated will depend on the concentration of species present in solution (nM-mM range), potential applied (−2V to +2V), type of waveform (pulse, constant, sawtooth, sinusoidal, square wave at different frequencies and duty cycles), and diffusion of the species (can be varied due to additives in the solution). These parameters can be optimized to get different pHs at each of the working electrodes present in a multisite array.

Example 2—pH Change Using Enzymatic Reactions

Enzymes such as oxidases, ureases or dehydrogenases have been known to consume or generate hydrogen during the reaction. For example:

$$\beta\text{-}d\text{-glucose} + O_2 \rightarrow d\text{-glucose-}\delta\text{-lactone} + H_2O_2$$

$$d\text{-glucose-}\delta\text{-lactone} + H_2O \rightarrow d\text{-gluconate} + H^+$$

Oxidation of glucose in the presence of glucose oxidase can produce H+ ions that are used to change the pH near the proteins of interest.

Example 3—Co-Immobilization of Enzymes Along with Biomolecular Probes in a Biomolecular Interface Layer The enzymes when co-immobilized on the surface along with proteins, reactants, catalysts, etc. brings them in close proximity so the H+ produced by the enzymatic reaction will lead to a localized pH change that can affect protein binding (for example antigen-antibody binding and non-specific binding), reaction rate, etc.

Example 4—Attaching the Enzymes to Magnetic Micro/Nanoparticles

Proteins, reactants, catalysts, etc. are attached to micro/nanocavities of a solid surface on an electromagnet. The enzymes are separately attached to magnetic micro/nanoparticles in the solution. Controlling a electromagnet that is fabricated/placed underneath controls the local pH values. The enzymatic reaction is triggered by introducing the corresponding enzyme substrate (as shown in FIG. 6). Alternatively electrochemically active enzymes are used. The pH change is localized on the cavities and the protein interactions, reaction rate, etc. are modulated.

Example 5—Electrochemical Modulation of pH as Monitored by Fluorescence Intensity with Green Fluorescence Protein (GFP)

Electrode material used: The electrode material was indium tin oxide. The fluorescent protein used is GFP immobilized on a glass substrate which includes an array of electrodes. The GFP is applied as spots, each spot covers an area that overlaps with one electrode and an area that is not overlapping with an electrode.

Figure 11:
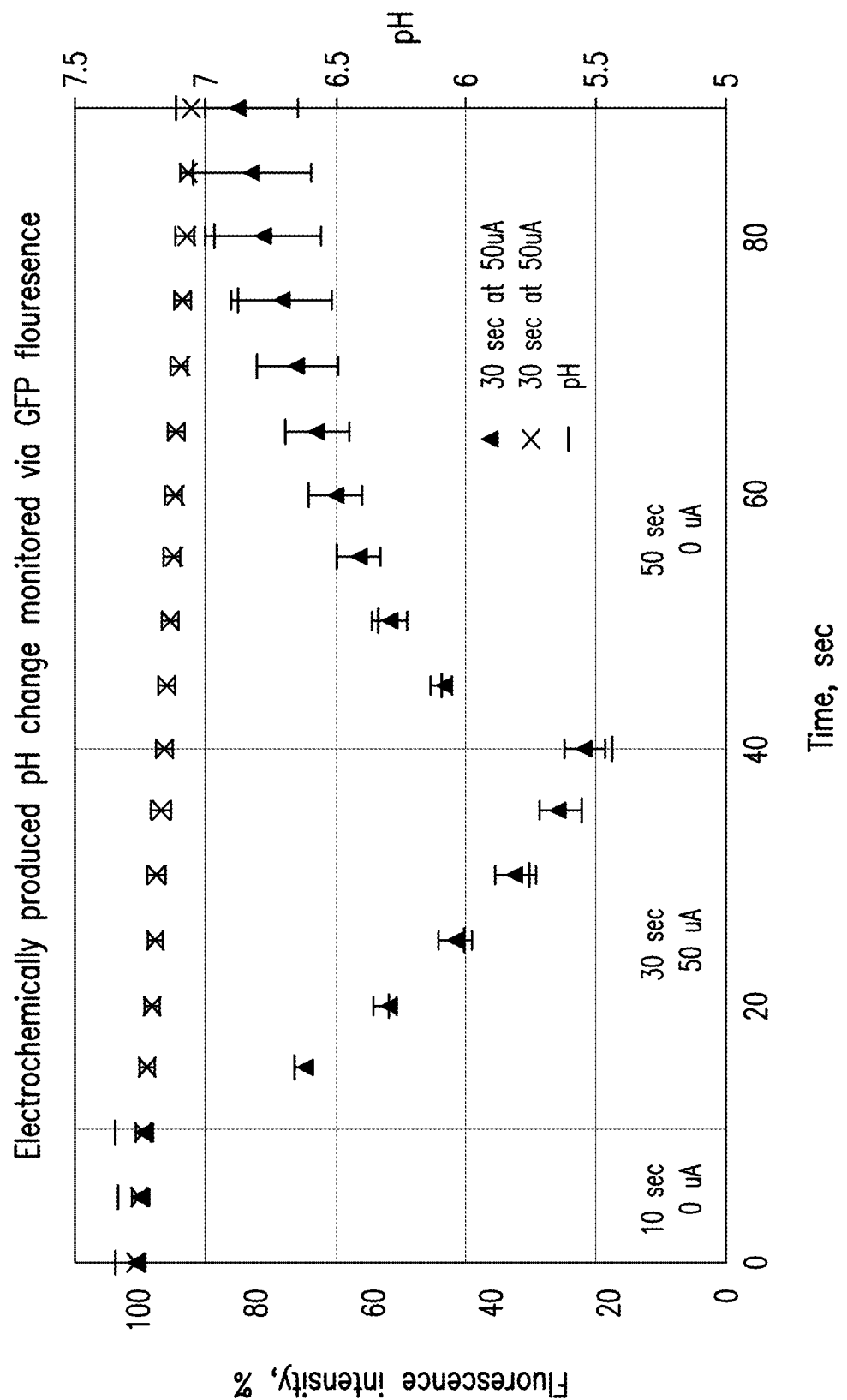
FIG. 11: shows the pH change at the surface of ITO working electrode generated via current-driven oxidation of a redox active molecule, 2-methyl-1,4-dihydroquinone, in diluted phosphate buffer (pH=7.4) containing $0.1M\ Na_2SO_4$. After 10 seconds of induction, current (50 microamps) was applied for 30 second, which resulted in a drop of solution pH to 5.5, as was observed by a change in GFP fluorescence intensity (FIG. 10 is used as calibration curve to assess the pH values). After current was turned off, the pH recovered to neutral value within 50 seconds.
Figure 12B:
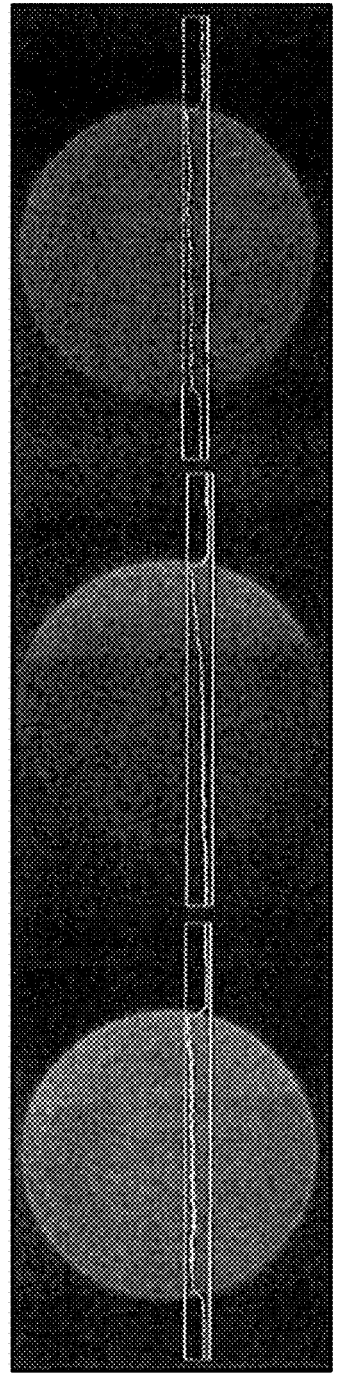

The pH change at the surface of ITO working electrode is generated via current-driven oxidation of a redox active molecule, 2-methyl-1,4-dihydroquinone, in diluted phosphate buffer (pH=7.4) containing 0.1M $Na_2SO_4$. After 10 seconds of induction, current (50 microamps) was applied for 30 second, which resulted in a drop of solution pH to 5.5, as was observed by a change in GFP fluorescence intensity. FIG. 10 is used as calibration curve to assess the pH values. After current was turned off, the pH recovered to neutral value within 50 seconds (as shown in FIGS. 11 and 12B).

Example 6—Preventing Reaction with Nucleophiles

Figure 23:
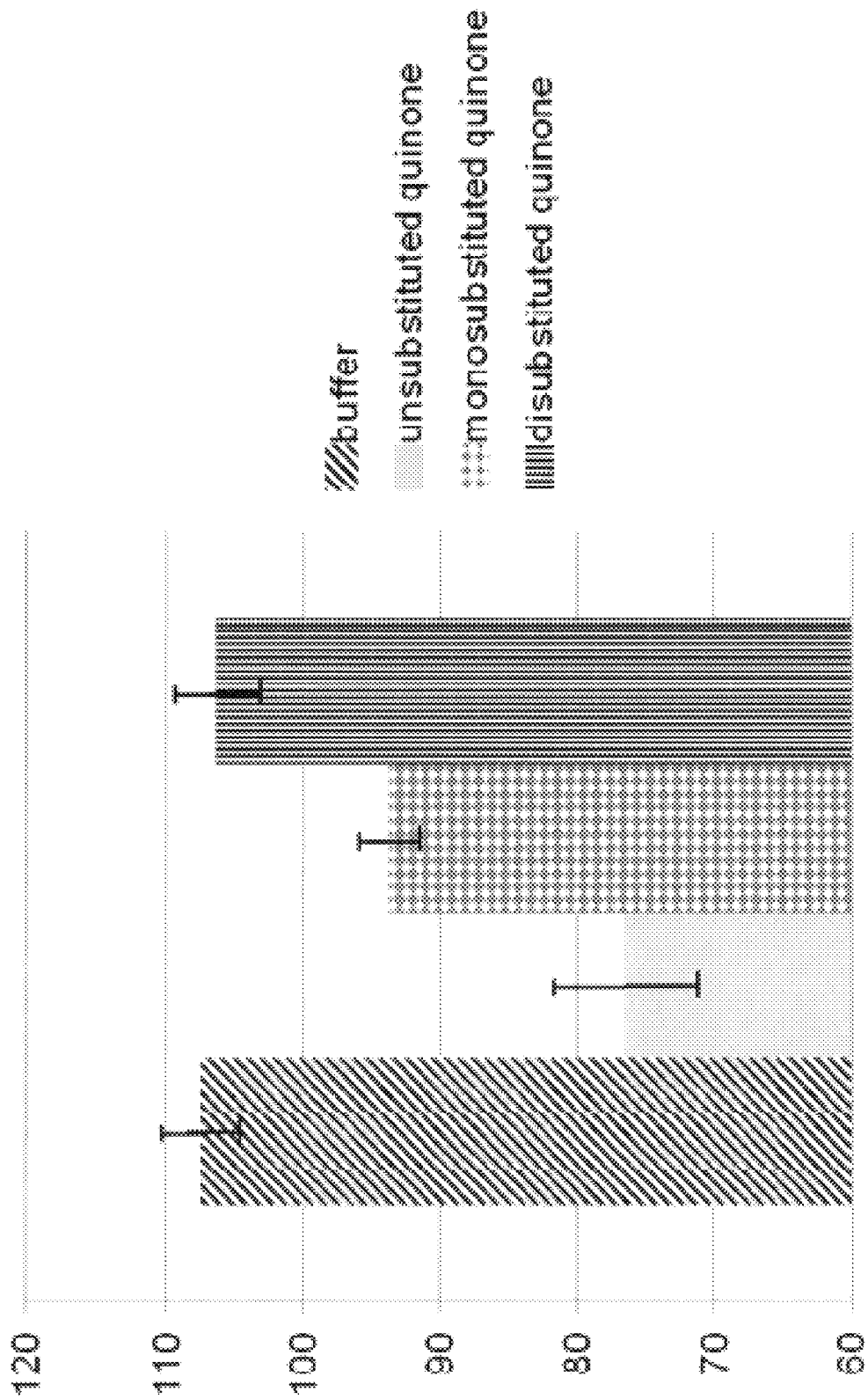
FIG. 23: demonstrates an effect of substitution in benzoquinones on the stability of proteins according to example embodiments of the preset invention.

Para-benzoquinones and ortho-benzoquinones (compounds 2, 4, 6, and 9 in FIG. 22) are susceptible to nucleophilic attack at the double bond of the ring (positions 2, 3, 5 and 6 in structure 2 of FIG. 22, positions 3, 4, 5 and 6 in structure 4 of FIG. 22, and positions 2 and 3 in structure 6 of FIG. 22). Introducing substituents at some or all of those positions can mitigate the problem of nucleophilic attack. For example, 1,4-benzoquinone (structure 2 in FIG. 22, where R1, R2, R3 and R4 are H) undergoes Michael addition reaction with amino groups of proteins (Loomis et al., Phytochemistry, 5, 423, (1966) and U.S. Pat. No. 6,753,312 B2). On the other hand, 2,5-disubstituted 1,4-benzoquinones (structure 2 in FIG. 21, where R1 and R3 are H, and R2 and R4 are groups other than H) do not show susceptibility to Michael addition reaction in the presence of proteins and are more suitable for use in biological buffers. FIG. 23 demonstrates the effect of substitution on protein stability in the presence of benzoquinones. Fluorescence intensity of Green Fluorescent Protein (GFP) was measured after incubation with three different benzoquinones in phosphate buffered saline for 30 min (concentration of benzoquinones was 0.5 mM). The difference in fluorescence intensity indicates the varied effect that the different substitutions in benzoquinones have on the stability of GFP. Fluorescence intensity of GFP is indicative of its structural integrity. Losses in fluorescence intensity usually indicate loss of its tertiary structure (protein denaturation) (Yin D. X., Zhu L., Schimke R. T. Anal. Biochem. 1996, 235:195-201). As shown in FIG. 23, GFP retains 100% of its fluorescence intensity after incubation with di-substituted benzoquinone for 30 min, while incubation with unsubstituted benzoquinone and mono-substituted benzoquinone causes 25% and 7% loss in fluorescence intensity, respectively.

Example 7—Tuning Water Solubility

Water solubility of aromatic compounds can be improved by introducing charged groups or atoms with lone pair electrons that can participate in hydrogen bonding. Such groups are, for example, —OH, —CH$_2$OH, —OCH$_3$, —COOH, —SO$_3$H, —NH$_2$, —NH$_3$Cl, —ONa. Sugars, amino acids, and peptides can also improve water solubility of quinones. Synthetic macromolecules such as polyethyleneglycoles can be used as substituents as well.

Example 8—Adjusting Redox Window

Reduction/oxidation potential of quinones can be tuned to fit the needs of specific application. By introducing electron-donating groups (such as alkyl, hydroxyl, alkoxy, methoxymethyl, morpholinomethyl, amino and chloro substituents) redox potential can be pushed towards higher voltage. Conversely, electron-withdrawing groups (such as nitro, cyano, carboxylic acid, or carboxylic ester groups) will push redox potential towards lower voltage.

In an example embodiment, the mechanism of oxidation of hydroquinones in aqueous solutions involves two steps: transfer of electrons and transfer of protons. Introducing electron-withdrawing or electron-donating substituents addresses the first step of the process. Oxidation potential of hydroquinones can also be lowered by introducing substituents that are capable of forming intramolecular hydrogen bonds with hydroxyl groups of hydroquinone. Such hydrogen bonding weakens the bond between hydrogen and oxygen of hydroxyl group, therefore lowering an overall energy barrier for oxidation reaction. Examples of such R groups are CH$_2$OH, CH$_2$OCH$_3$, morpholinomethyl, and COOCH$_3$.

Having the ability to select molecules which undergo electrochemical transformation through the same mechanism, but at different potentials enables one to accommodate different pH conditions and avoid undesirable electrochemical reactions involving other redox active components in the system. For example, for applications involving DNA synthesis, it is preferred to keep the voltage below the reduction potentials of pyrimidine bases, nucleosides, and nucleotides (1V vs. NHE in aqueous solution pH ~8) (Steenken, S. J Am Chem Soc, 1992, 114: 4701-09).

Autooxidation of hydroquinones is another issue to be considered. In an example embodiment, in order to avoid oxidation, a quinone derivative with high enough electrochemical oxidation potential that is resistant to spontaneous chemical oxidation by molecular oxygen is used.

Conversely, benzoquinones with low enough reduction potentials should be chosen for systems where reducing agents, like mercaptoethanol, glutathione, and dithiothreitol are present in solution. Examples of such applications are DNA synthesis, electrophoresis, and immunoassays.

Figure 24:
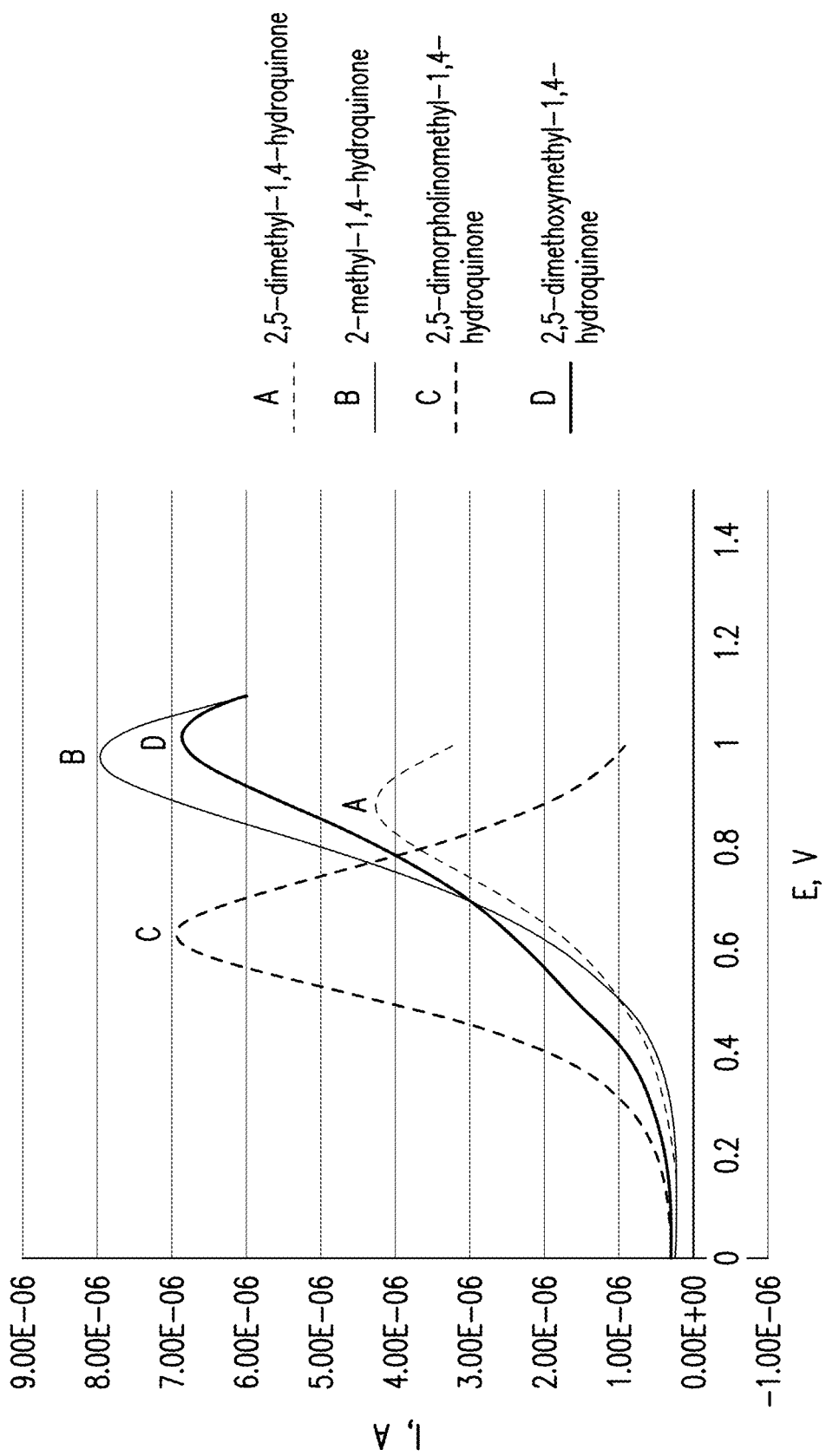
FIG. 24: shows square wave voltammograms of substituted quinones in buffered solution (vs. Ag/AgCl) according to example embodiments of the present invention.

The redox potential of quinones is affected by the pH of the solution. It is easier to oxidize hydroquinones in more basic pH, whereas more acidic pH will require higher oxidation potentials. This, in turn, affects stability of hydroquinones towards autooxidation by oxygen in air. Therefore, if one needs to work in basic pH, using a quinone with higher oxidation potential will improve the stability of electrochemical system. FIG. 24 shows that there are different oxidation potentials for different substituents in quinones (FIG. 24, A-D), and therefore, the oxidations potential can be tuned by varying the substituents in quinones.

Example 9—Synthesis of Substituted Quinones

Figure 25:
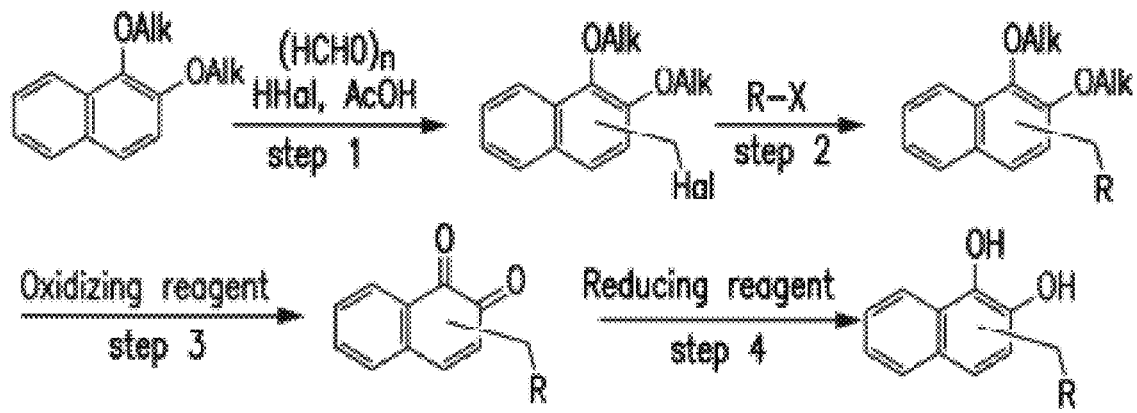
FIG. 25: shows steps for the synthesis of substituted hydroquinones and benzoquinones.

Scheme 1 shown in FIG. 25 is a representation of a synthesis of substituted quinone according to an example embodiment of the present invention.

Example 10—2,5-dimethyl-1,4-hydroquinone

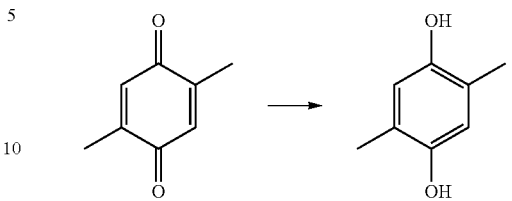

Sodium dithionate (18.7 g, 107.3 mmol, 7.3 equiv) was dissolved in 20 mL H$_2$O and loaded into a separatory funnel. Next, a solution of benzoquinone (2 g, 14.7 mmol, 1 equiv) in 75 mL diethyl ether was added. The diphasic mix was stirred vigorously for 30 minutes and the organic layer changed color from orange to pale yellow. Organic phase was washed with brine, dried over MgSO$_4$, and concentrated to yield a white solid (1.69 g, 83%).

Example 11—1,4-Bis(bromomethyl)-2,5-dimethoxybenzene

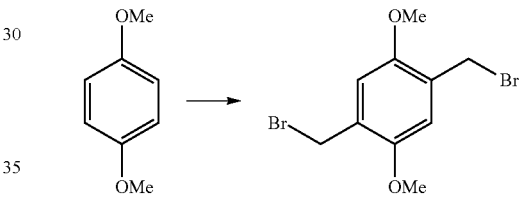

Paraformaldehyde (Aldrich, 4.27 g, 144.75 mmol) and HBr/AcOH (Fluka, 33%, 30 mL) were added slowly to a stirred solution of 1,4-dimethoxybenzene (Aldrich, 10.00 g, 72.37 mmol) in glacial acetic acid (Fisher, 50 mL). The mixture was stirred at 50° C. for one hour, allowed to cool to room temperature, and then hydrolyzed in water (200 mL). The white solid was collected by filtration, suspended in CHCl$_3$ (50 mL), and refluxed for 10 min. After cooling to room temperature, the white solid was again collected by filtration and washed with water (15.75 g, 67%). NMR spectra were obtained experimentally to confirm the chemical structure of the resulting compound and its purity. NMR results were as follows: $^1$H NMR (300 MHz, CDCl$_3$) δ 6.88 (s, 2H), 4.54 (s, 4H), 3.87 (s, 6H) ppm.

Example 12—1,4-dimethoxy-2,5-dimethoxymethylbenzene

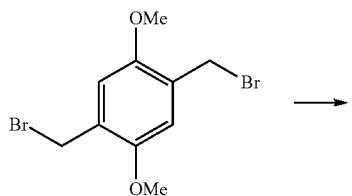

-continued

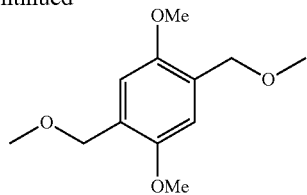

A dry round bottom flask was charged with 2,5-dibromomethyl-1,4-dimethoxybenzene (3 g, 9.26 mmol, 1.0 equiv), anhydrous K$_2$CO$_3$ (25.6 g, 185 mmol, 20 equiv), and dry methanol (200 mL). The reaction mixture was heated to reflux for 30 min, then cooled to ambient temperature, filtered, and concentrated to a crude white solid. The solid was resuspended in water and extracted with ethyl acetate, dried over MgSO$_4$, and concentrated. The residue was recrystallized in hexanes as a pale yellow powder (1.2 g, 57%). Retention factor (Rf) (50% EtOAc/hexanes)=0.65.

Example 13—2,5-dimethoxymethyl-1,4-benzoquinone

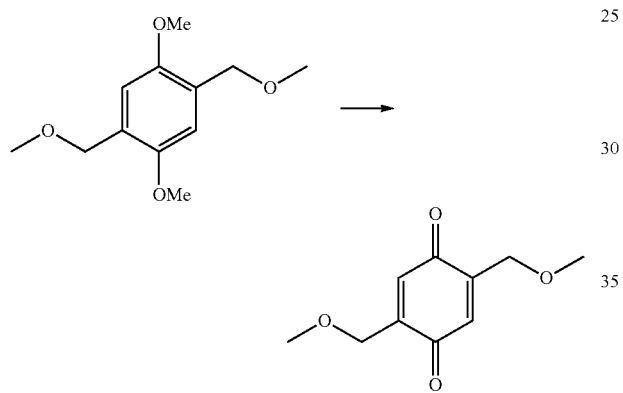

A solution of 1,4-dimethoxy-2,5-dimethoxymethylbenzene (1.2 g, 5.24 mmol, 1.0 equiv) in acetonitrile (0.1 M, 52 mL) was treated with a solution of cerium ammonium nitrate (5.8 g, 10.6 mmol, 2.02 equiv) in water (8 mL). The reaction mixture was stirred under argon at ambient temperature for 30 minutes, then diluted with water, and extracted with dichloromethane. The combined organic layers were washed with water, dried over Na$_2$SO$_4$, and concentrated to an orange solid. The crude mix was purified by column chromatography on deactivated silica gel (0-5% ethyl acetate/hexanes) to yield yellow crystals (300 mg, 67%). Rf (50% EtOAc/hexanes)=0.7; $^1$H NMR (300 MHz, CDCl$_3$) δ: ppm; UV-Vis=268 nm.

Example 14—2,5-dimethoxymethyl-1,4-hydroquinone

The benzoquinone obtained according to the reaction of Example 13 (200 mg, 1.02 mmol, 1.0 equiv) in 2.5 mL EtOAc was treated with a solution of sodium dithionate (1.3 g, 7.44 mmol, 7.3 equiv) in 2 mL H$_2$O. The diphasic mix was stirred vigorously for 30 minutes and the solution changed colors from bright to pale yellow. The mixture was diluted with water, extracted with ethyl acetate, dried over MgSO$_4$, and concentrated to a white powder (96 mg, 48%).

Example 15—1,4-dimethoxy-2,5-dihydroxymethylbenzene

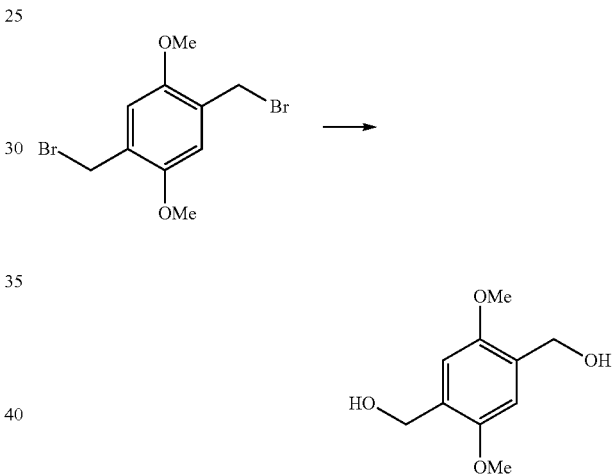

A dry round bottom flask was charged with 2,5-dibromomethyl-1,4-dimethoxybenzene (5 g, 15.4 mmol, 1.0 equiv) and NaOH (77 mL of 1.0 M solution, 77 mmol, 5.0 equiv), 12 mL H$_2$O, and 38 mL THF. The reaction mixture was sealed and heated to 80° C. for 6 h. After cooling, the reaction mixture was concentrated by rotary evaporation to a crude solid that was recrystallized in hexanes to a white powder (3 g, 60%). Rf (80% EtOAc/hexanes)=0.2.

Example 16—2,5-dimethoxymethyl-1,4-benzoquinone

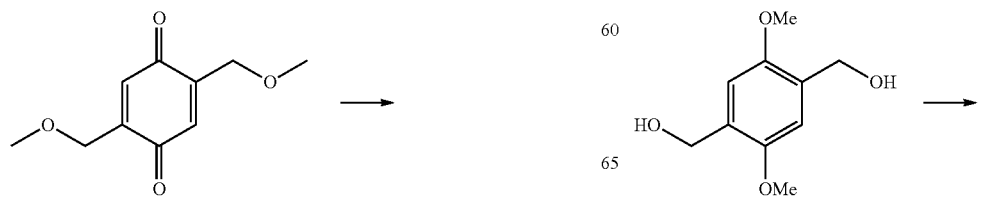

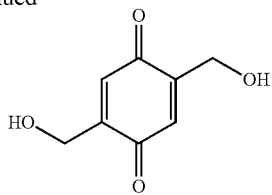

A solution of 1,4-dimethoxy-2,5-dihydroxymethylbenzene (1.0 g, 5.04 mmol, 1.0 equiv) in acetonitrile (0.2 M, 25 mL) was treated with a solution of cerium ammonium nitrate (5.5 g, 10.1 mmol, 2.0 equiv) in water (33 mL) at 0° C. The reaction mixture was stirred under argon at ambient temperature for 30 min, and then extracted with EtOAc. The combined organic layers were dried over $Na_2SO_4$ and concentrated to an orange-red solid. The crude mix was purified by column chromatography on deactivated neutral alumina (0-100% ethyl acetate/hexanes) to yield yellow crystals (300 mg, 67%). Rf (80% EtOAc/hexanes)=0.4; $^1$H NMR (DMSO, 500 MHz): 6.6 (s, 2H), 5.3 (s, 2H), 4.3 (s, 4H), ppm; $^{13}$C NMR (DMSO, 125 MHz): 187.4, 149.1, 129.8, 57.0 ppm; UV-Vis=260 nm.

Example 17—2,5-dihydroxymethyl-1,4-hydroquinone

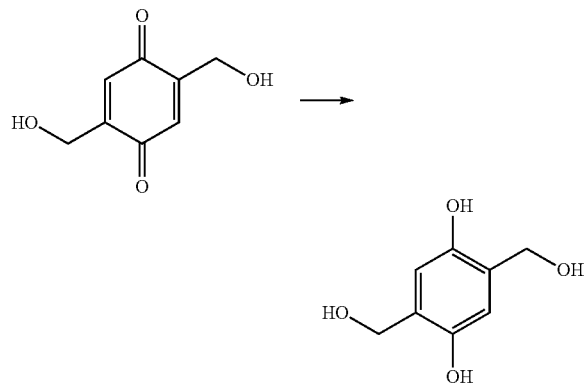

The benzoquinone obtained according to the reaction of Example 16 (60 mg, 0.36 mmol, 1.0 equiv) in 0.6 mL EtOAc was treated with a solution of sodium dithionate (453 mg, 2.6 mmol, 7.3 equiv) in 0.7 mL $H_2O$. The diphasic mix was stirred vigorously for 30 minutes and the solution changed colors from bright to pale yellow. The mixture was diluted with water, extracted with ethyl acetate, dried over $MgSO_4$, and concentrated to a crude solid that was purified by column chromatography on deactivated neutral alumina under Ar to yield a white powder (26 mg, 30%). UV-Vis=297 nm.

Example 18—Open Loop Method

According to an example embodiment, a method, termed open loop pH control, involves using electric current or electric potential shaping to maintain a desired pH of a solution close to the electrode. The method uses an understanding of the electrochemical components of the system, the major constituents being the reduction/oxidation properties of the quinone, the starting pH of the solution, the electron transfer coefficient of the electrode material, the redox molecule concentration, the salt concentration, and the buffer composition and concentration. All these components can impact how the electrochemical reaction changes the pH close to the electrode. With this understanding and by incorporating experimental data, a series of models can be used to define the waveforms to change the pH as required.

Figure 26:
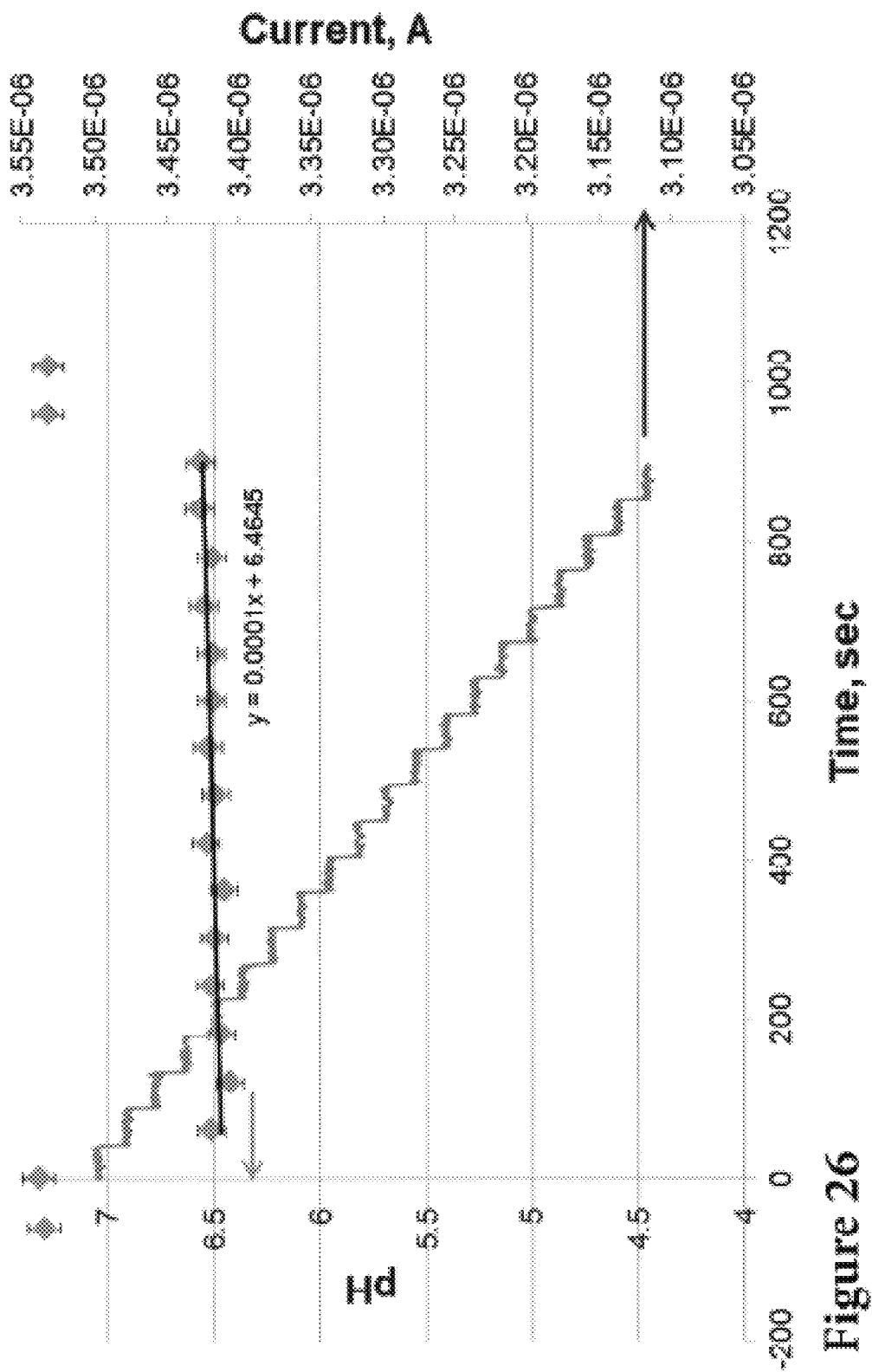
FIG. 26: illustrates an open loop waveform used to maintain the pH of a solution close to an electrode, according to an example embodiment of the present invention.

FIG. 26 shows an outcome from an open loop waveform experiment designed to hold the pH of the solution close to the electrode at pH 6.5 over 15 minutes. The stepped trace approximately extending between current values 3.12e−6 and 3.50e−6 correlates with the current applied to the system (right axis). The approximately straight trace correlates with the observed pH close to the electrode surface, which is measured by analyzing the pH dependent fluorescence of green fluorescent protein bound to the surface (left axis).

Figure 27:
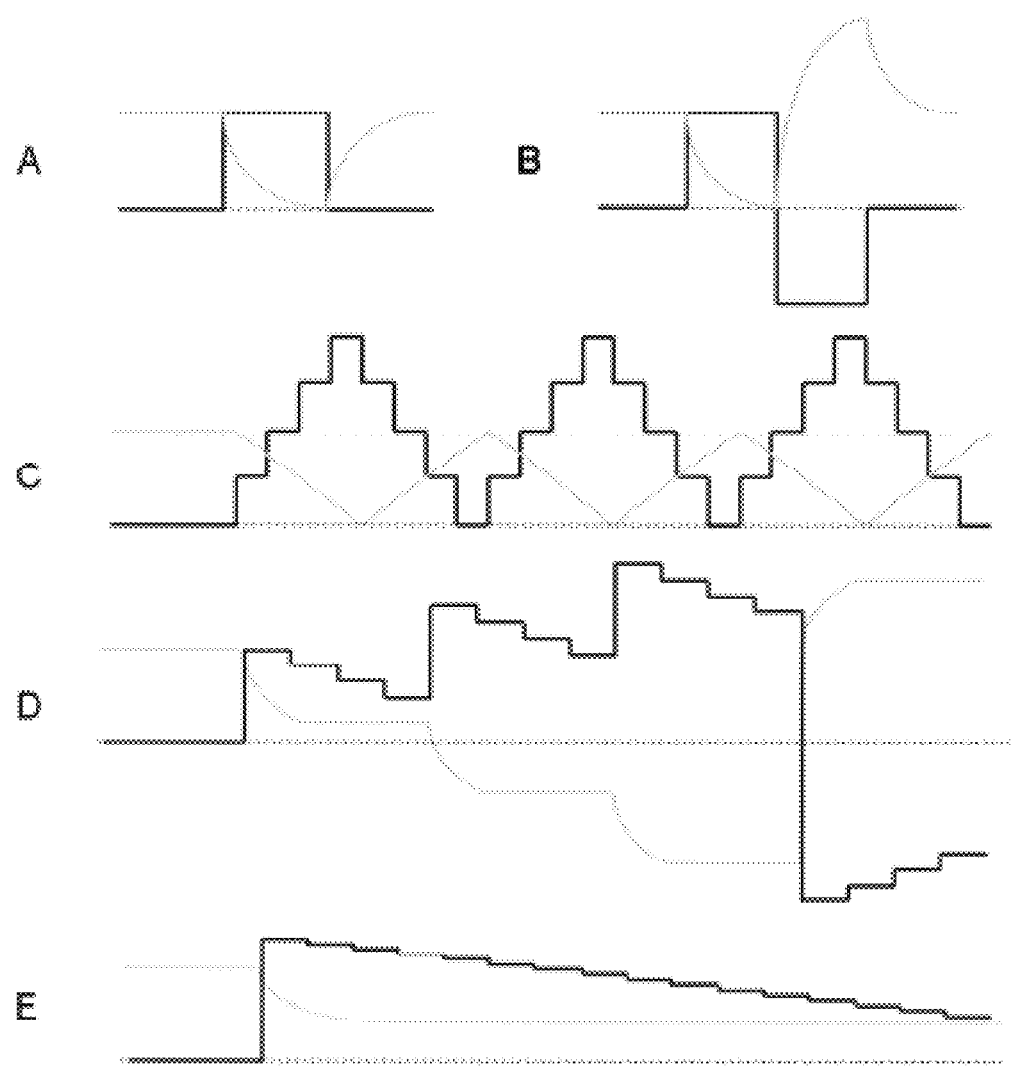
FIG. 27: illustrates examples of waveform shaping for pH control, according to example embodiments of the present invention.

FIG. 27 shows four different examples of waveforms (A-E) usable to shape and control the pH of the solution. The black line is the current/potential driven input and the grey line is the resultant pH change in the solution close to the electrode surface plotted over time.

Figure 31:
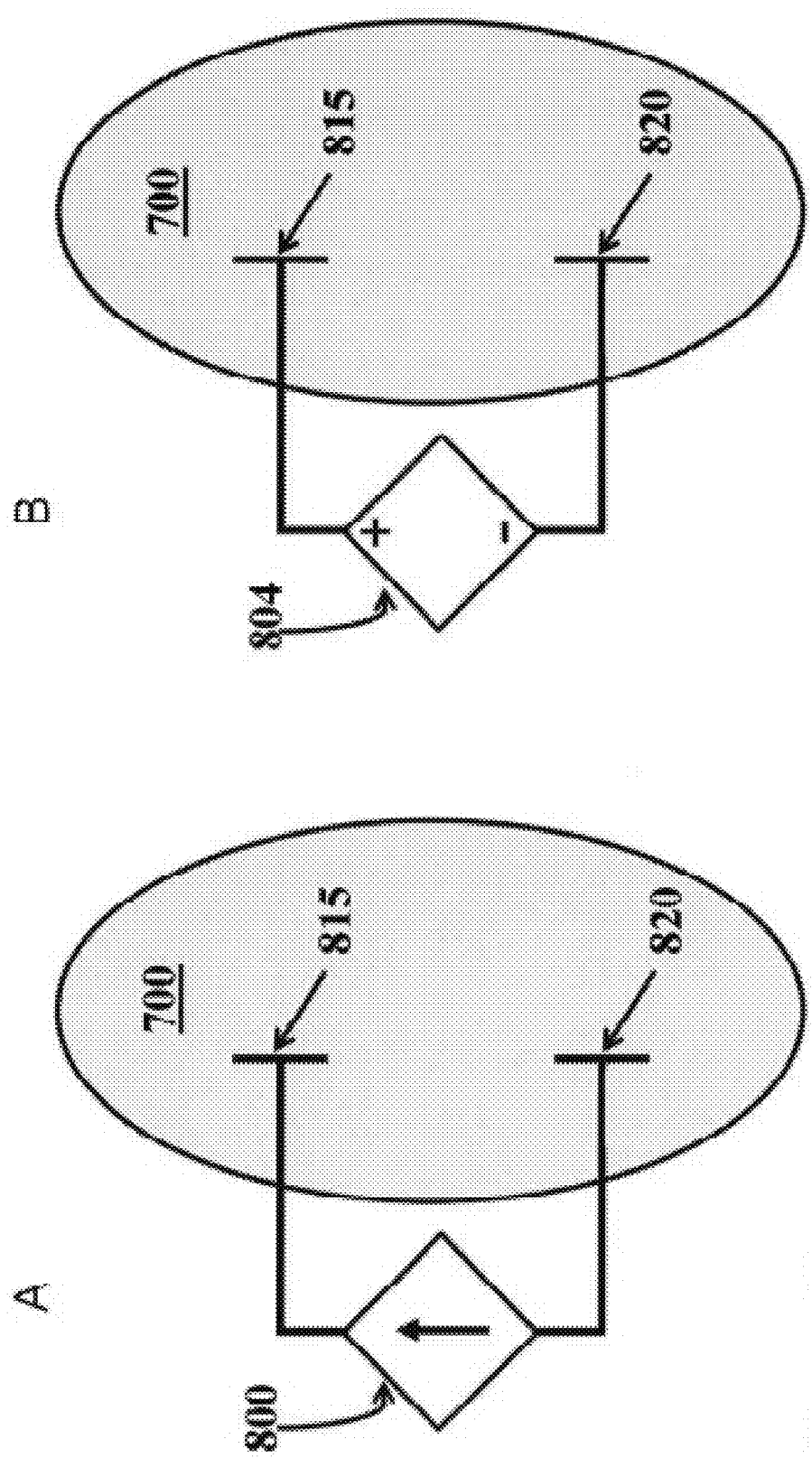
FIG. 31: illustrates open loop schematics, where in part A, a controlled current source is used, while in part B, a controlled voltage source is used, according to an example embodiment of the present invention.

If the relevant electrochemical components of a system remain fixed, these waveforms can be used to reproducibly generate the same pH change profile of the solution on demand without additional complexity. The method can be implemented using various electrode systems, schematics of example setups are shown in FIG. 31, A-B. The method requires a minimum of 2 electrodes 815, 820. Initially, the open circuit potential of the solution close to the electrode 700 can be measured by applying zero current between the 2 electrodes 815, 820. In this state, one electrode acts as the sense electrode (SE) 815 and the second acts as a reference electrode (RE) 820. Once the starting OCP is known, a current 800 (FIG. 31, A) or an electric potential 804 (FIG. 31, B) is applied to the electrodes 815, 820 based on the desired pH change. While a current or potential is being applied, one electrode 815 acts as a working electrode (WE) and the second electrode 820 acts as a counter electrode (CE). This is the simplest case in that the conditions of the system must remain fixed, but to improve accuracy, a method for continuous feedback of the system state is preferred.

Example 19—Closed Loop Method

According to another example embodiment, a method, termed closed loop pH control, uses the open circuit potential as a feedback measurement to control the current or potential.

Figure 29A:
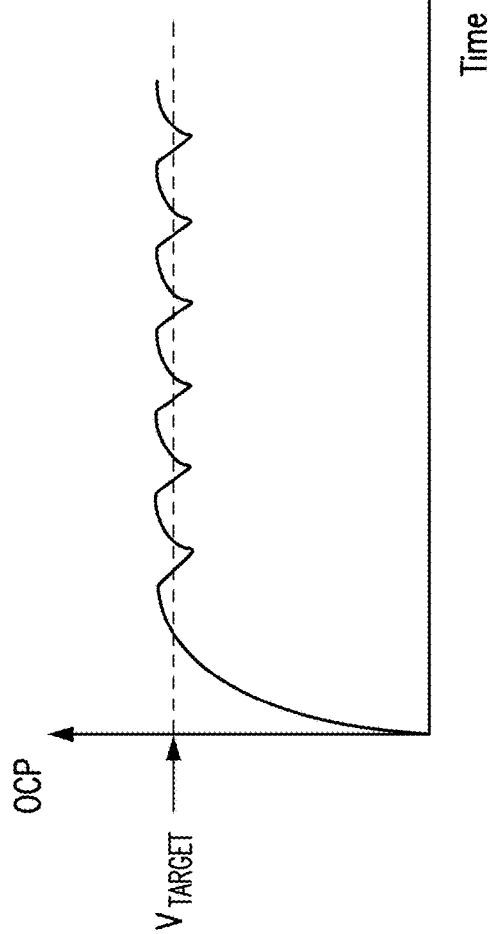
FIGS. 29A-29B: illustrate, in FIG. 29A, a controlled OCP on a sense electrode (SE) by using a closed loop feedback method with a single OCP $V_{TARGET}$, and illustrates, in FIG. 29B, experimental results of a controlled OCP on the SE by using a closed loop feedback with defined upper and lower OCP $V_{TARGET}$ values, according to an example embodiment of the present invention.
Figure 32:
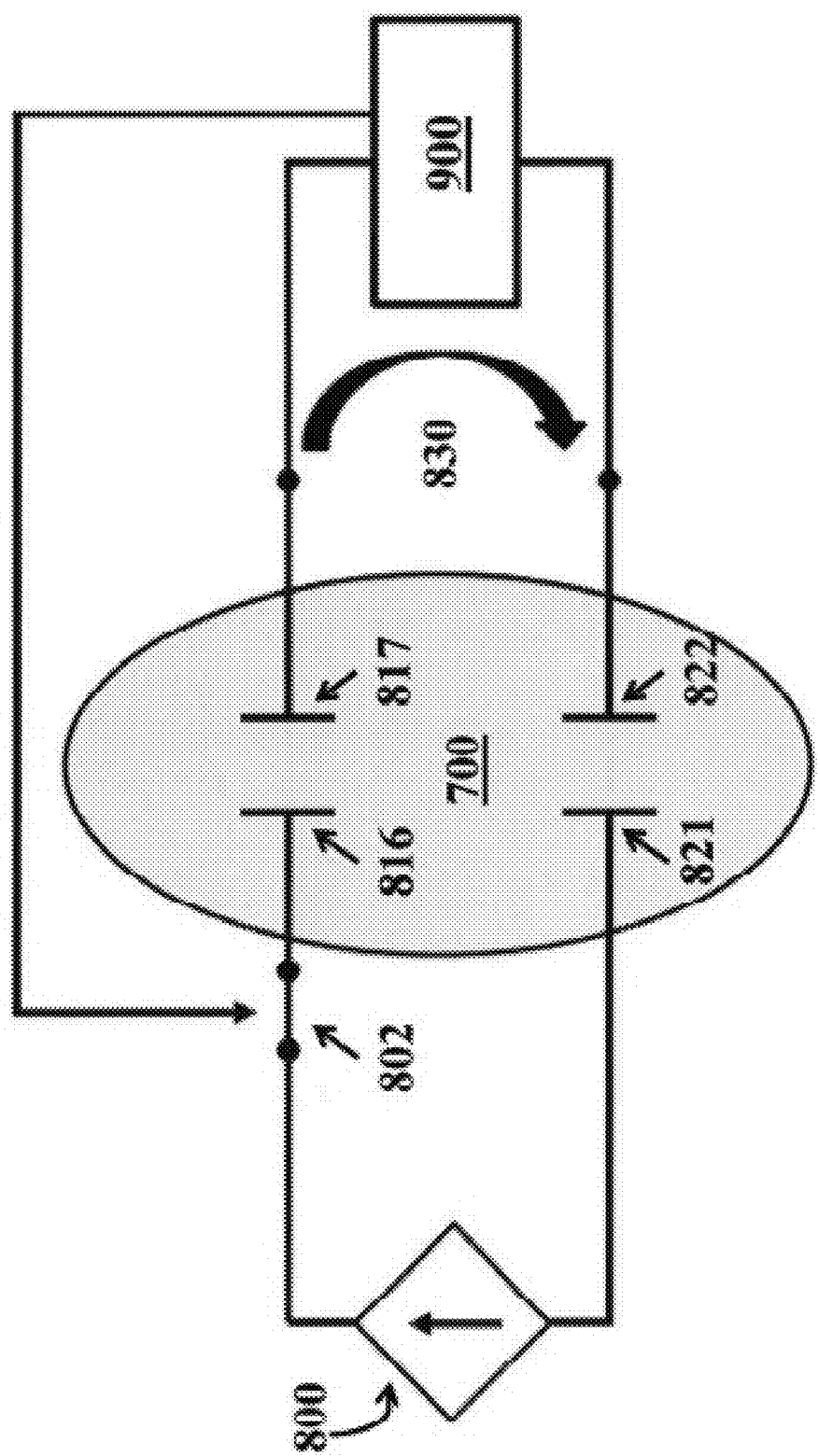
FIG. 32: illustrates a closed loop single controlled current source, according to an example embodiment of the present invention.
Figure 33:
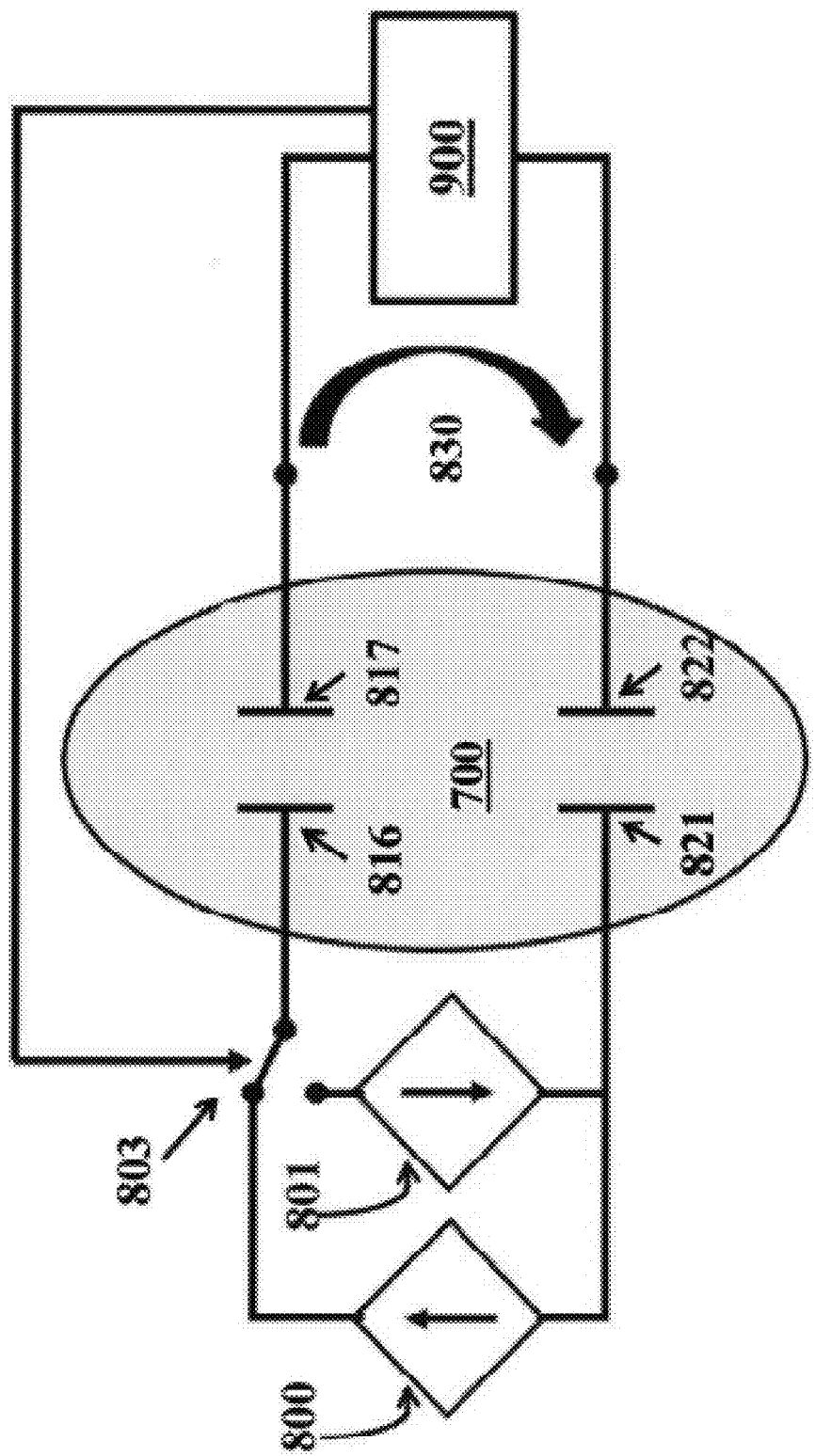
FIG. 33: illustrates a closed loop dual controlled current source, according to an example embodiment of the present invention.
Figure 34:
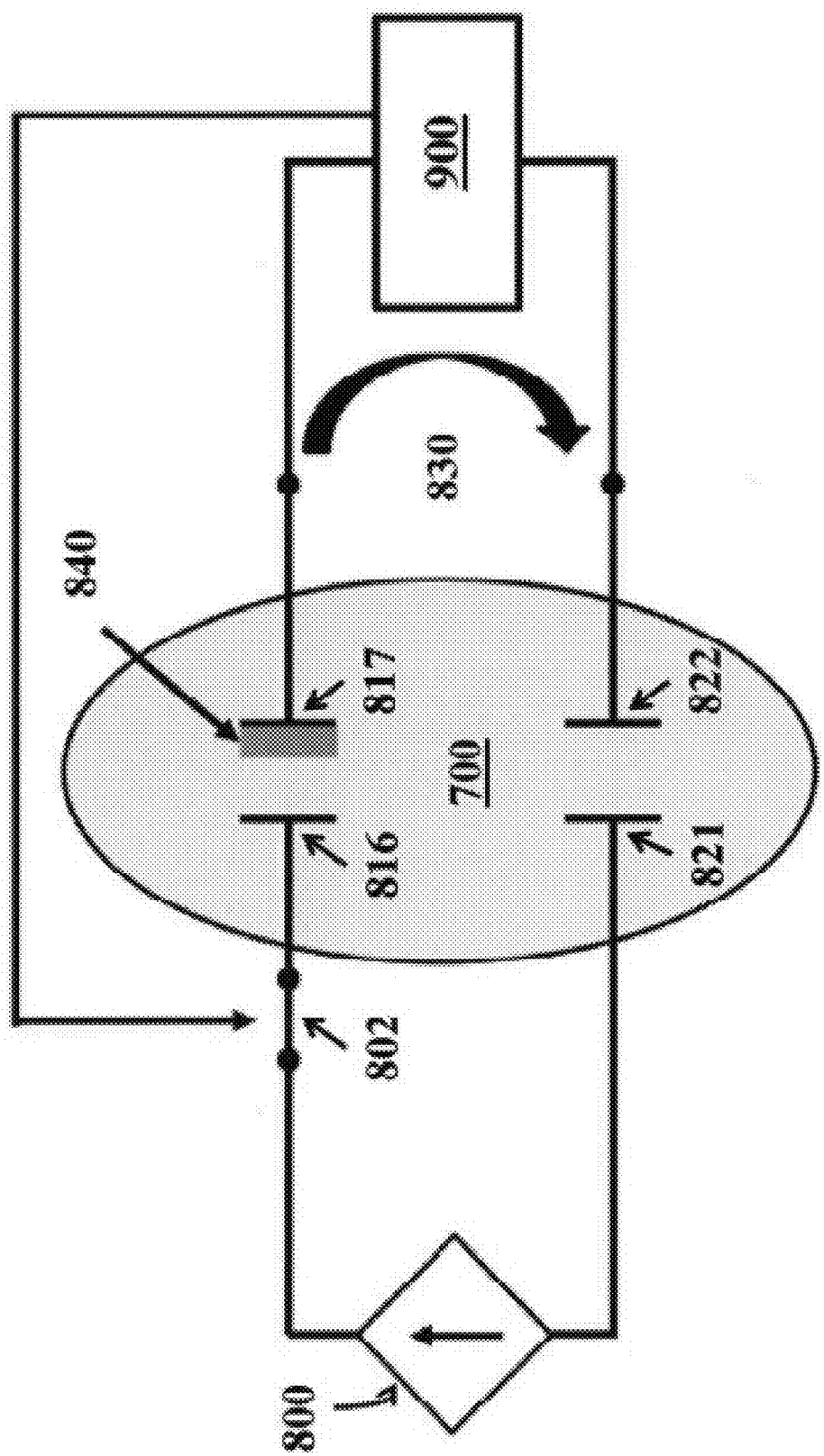
FIG. 34: illustrates a closed loop single controlled current source with a PANI coated sense electrode, according to an example embodiment of the present invention.
Figure 35:
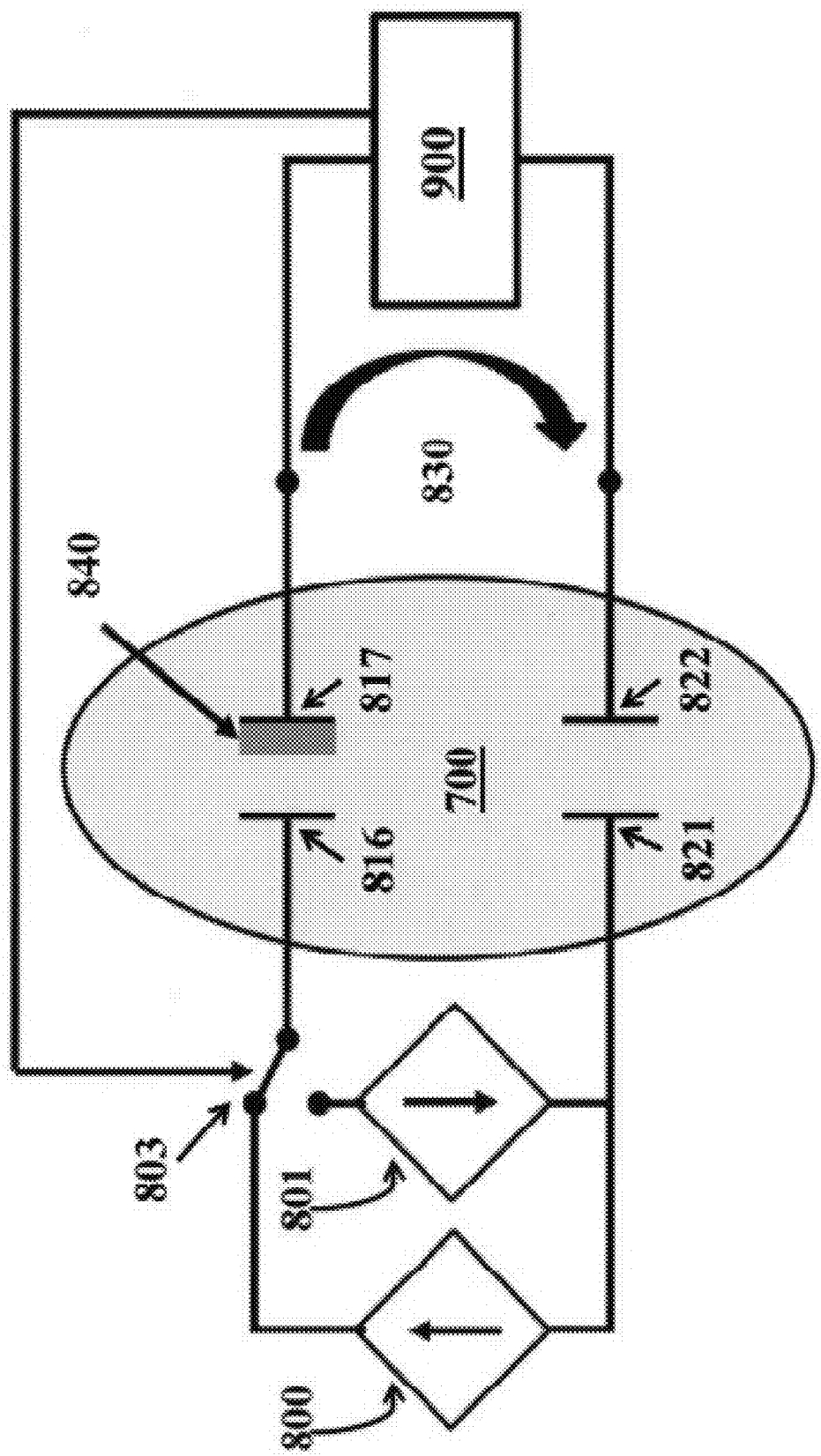
FIG. 35: illustrates a closed loop dual controlled current source with a PANI coated sense electrode, according to an example embodiment of the present invention.
Figure 36:
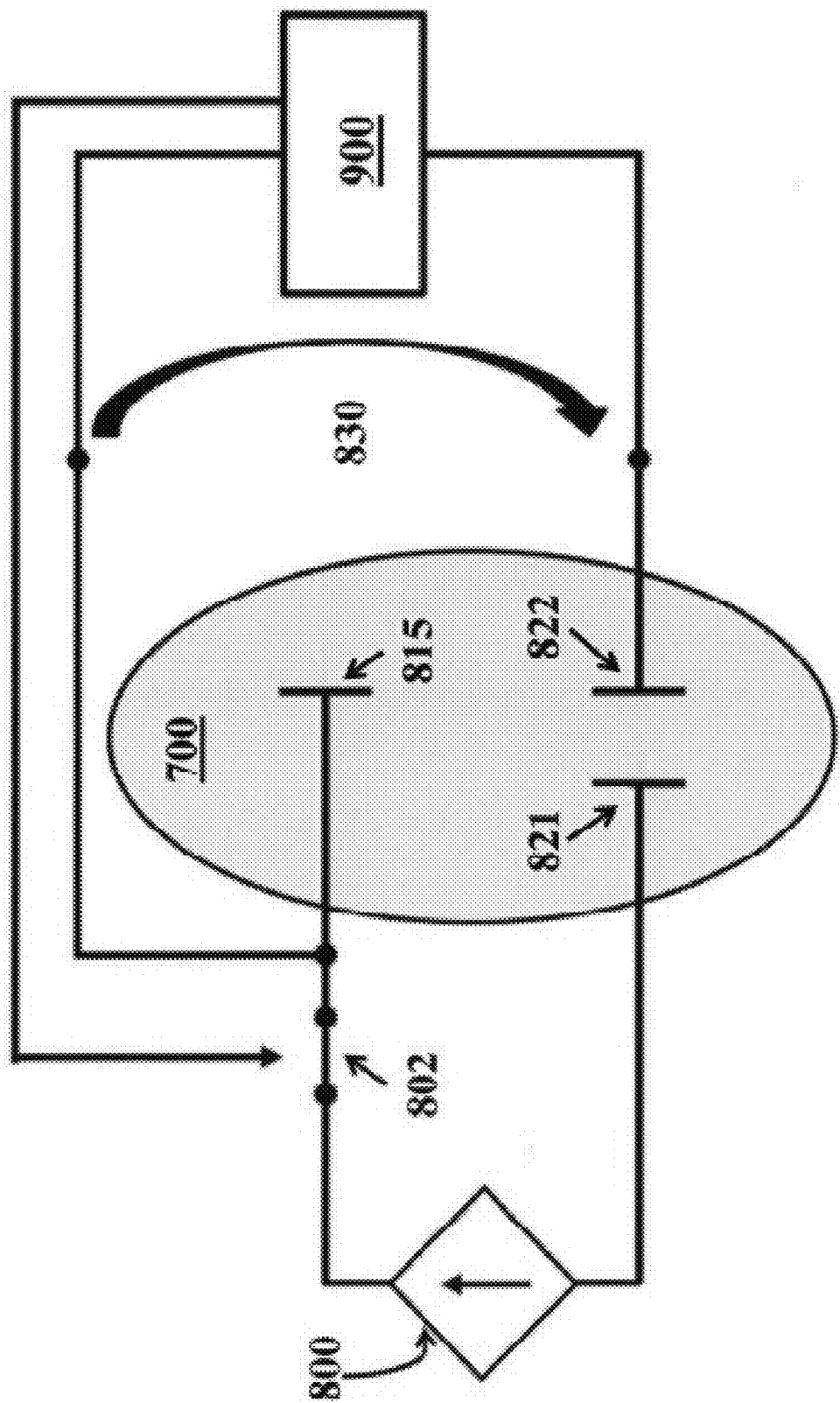
FIG. 36: illustrates a closed loop single controlled current source with a combined working and sense electrode, according to an example embodiment of the present invention.
Figure 37:
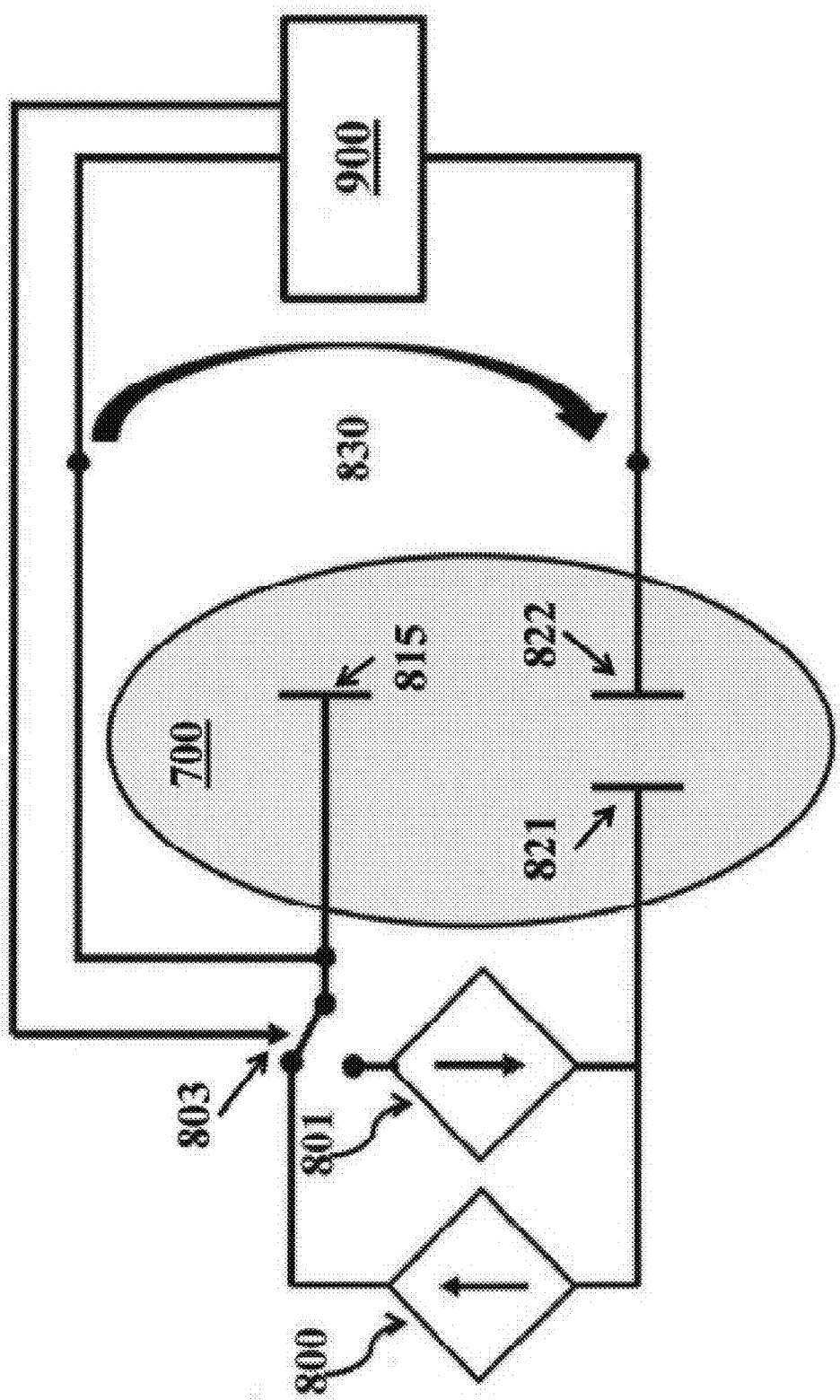
FIG. 37: illustrates a closed loop dual controlled current source with a combined working and sense electrode, according to an example embodiment of the present invention.
Figure 38:
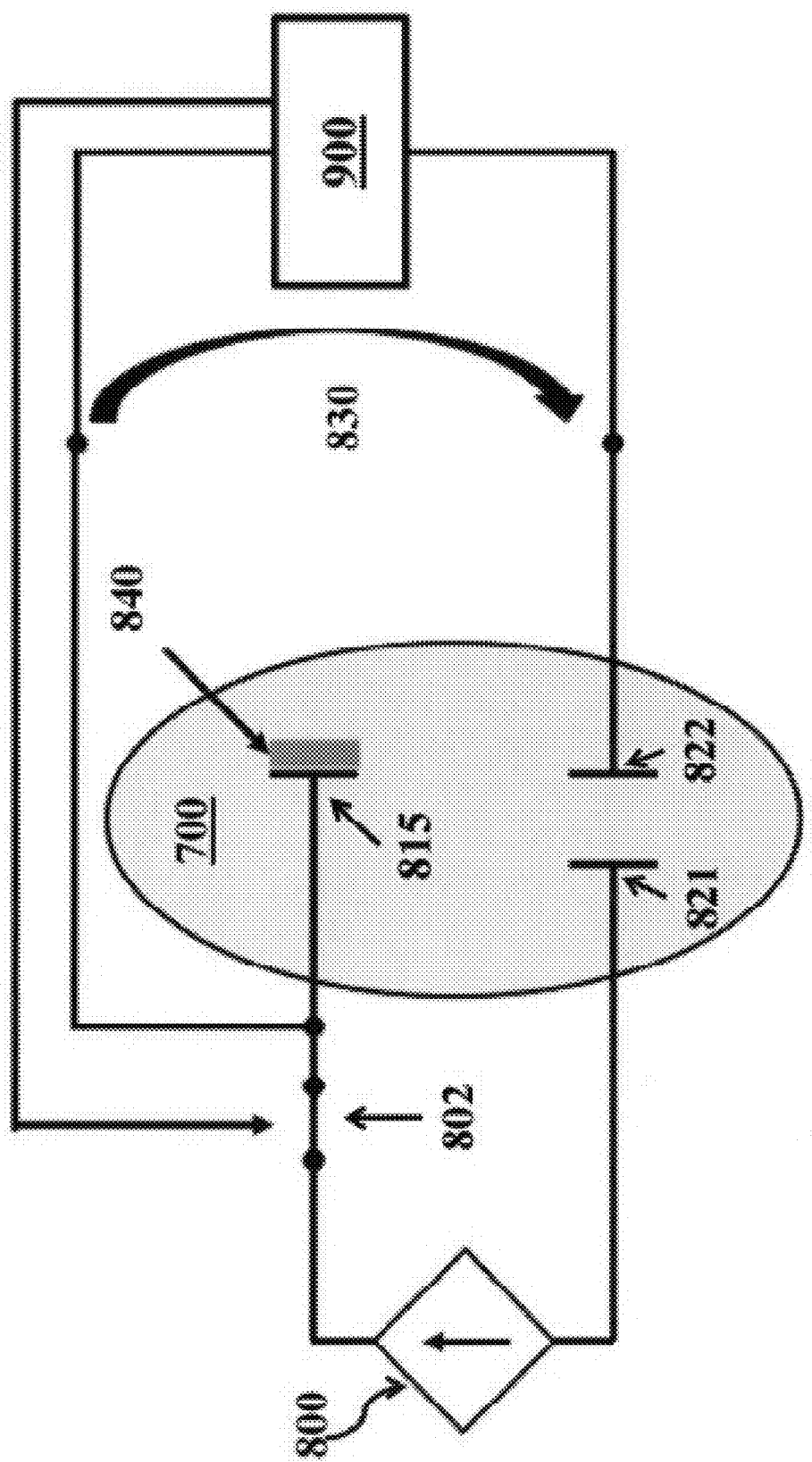
FIG. 38: illustrates a closed loop single controlled current source with a combined working and sense electrode with PANI coating, according to an example embodiment of the present invention.
Figure 39:
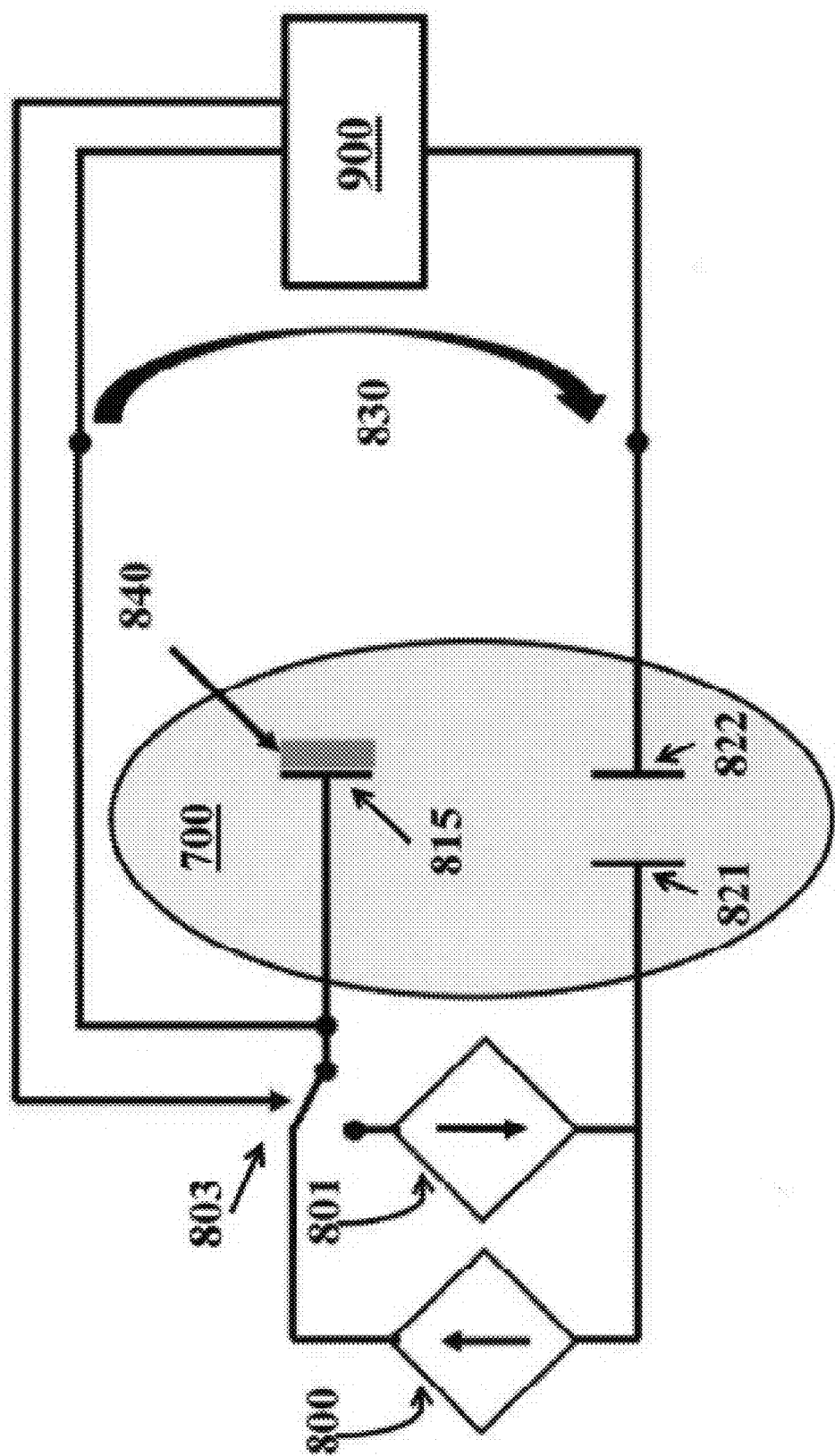
FIG. 39: illustrates a closed loop dual controlled current source with a combined working and sense electrode with PANI coating, according to an example embodiment of the present invention.

FIG. 29A illustrates a controlled OCP on the sense electrode (SE) by using a closed loop feedback method with a single OCP $V_{TARGET}$. In one setup (shown in FIG. 32), the system is driven to apply a current from a current source 800 to increase the $H^+$ concentration in solution 700 until the $V_{in}$ 830 detected by the SE 817 reaches a single OCP $V_{TARGET}$ value. Then current source 800 is shut off using switch 802 and diffusion of the $H^+$ ions away from the SE 817 results in reduction of the $H^+$ concentration in solution 700. Similarly, the system can be set to drive a decrease in the $H^+$ concentration until a OCP $V_{TARGET}$ value is reached and then diffusion of the $H^+$ ions towards the SE results in increase of the $H^+$ concentration (not shown). In another setup (shown in FIG. 33), positive 800 and negative 801 current sources are used so that the system does not need to rely on diffusion to facilitate the change of pH. This system can actively change the pH in both a positive and negative direction. In this setup the system is driven to apply a positive current from a current source 800 to increase the H$^+$ concentration until the V$_{in}$ 830 reaches a single OCP V$_{TARGET}$ value and a changeover switch 803 is used to connect a negative current source 801 to the working electrode (WE) 816 to apply a negative current and drive the setup in reverse to reduce the H$^+$ concentration. This way, the system does not rely on passive diffusion but actively monitors and adjusts the pH by electronic control.

Figure 29B:
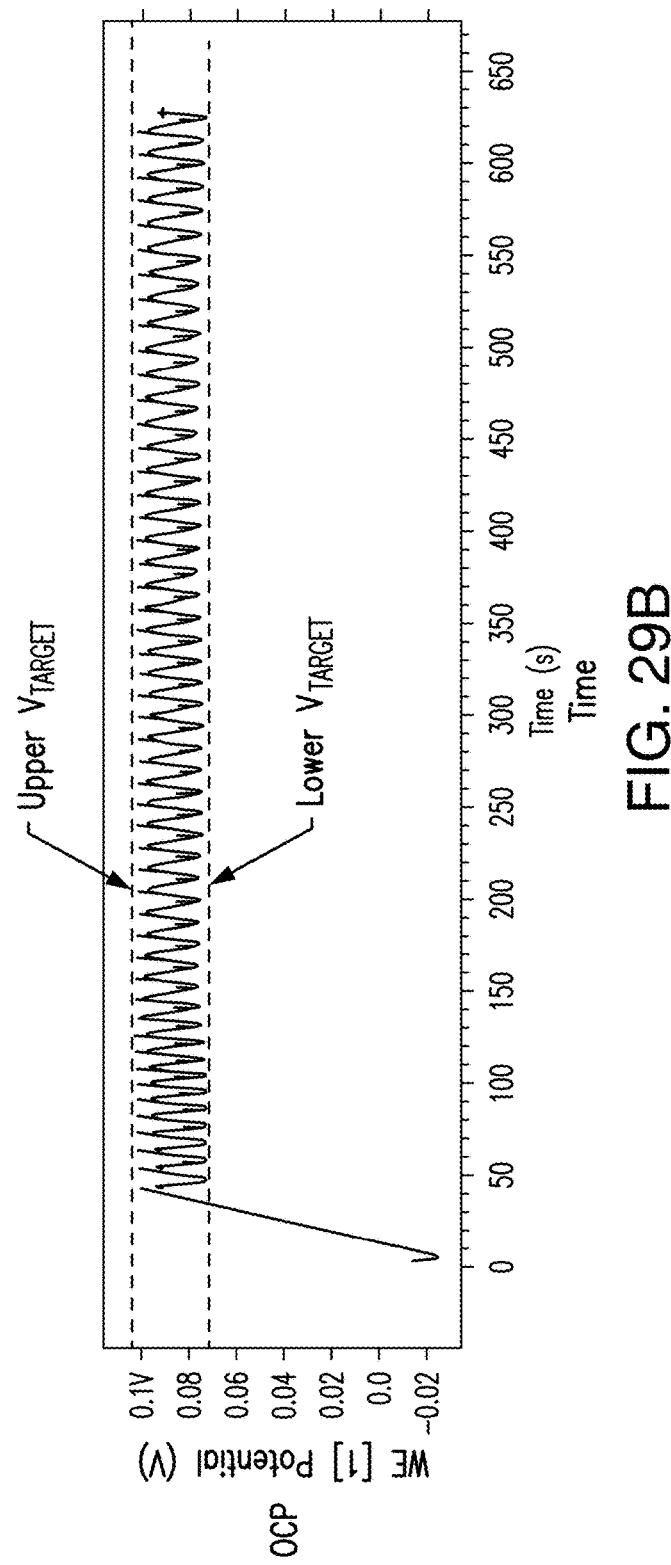

FIG. 29B shows experimental data of the OCP between the SE 817 and RE 822, which changes as current is applied to the WE 816. In this setup (shown in FIG. 32), an upper and a lower target are pre-set via controller 900 for the value of the OCP on the SE 817. The feedback activates current driven pH change when the potential is below the lower bound and switch 802 cuts the current when above the upper bound. The data shows the OCP rising until the upper target is reached. The feedback then switches off the WE 816, which leads to a drop in the OCP as the buffer from the bulk starts to restore the local pH of solution 700. When the OCP reaches the lower target, the current is re-initiated using switch 802 to increase the OCP again. This feedback mechanism allows a defined pH for solution 700 to be maintained close to the WE 816. In another setup (shown in FIG. 33), the feedback can be activated to continuously change the OCP so that a positive current is applied to actively increase the OCP until the upper bound is reached and then a negative current in applied in reverse to actively decrease the OCP until a lower bound is reached. This way, the system does not rely on passive diffusion but actively monitors and adjusts the pH by electronic control.

Figure 30:
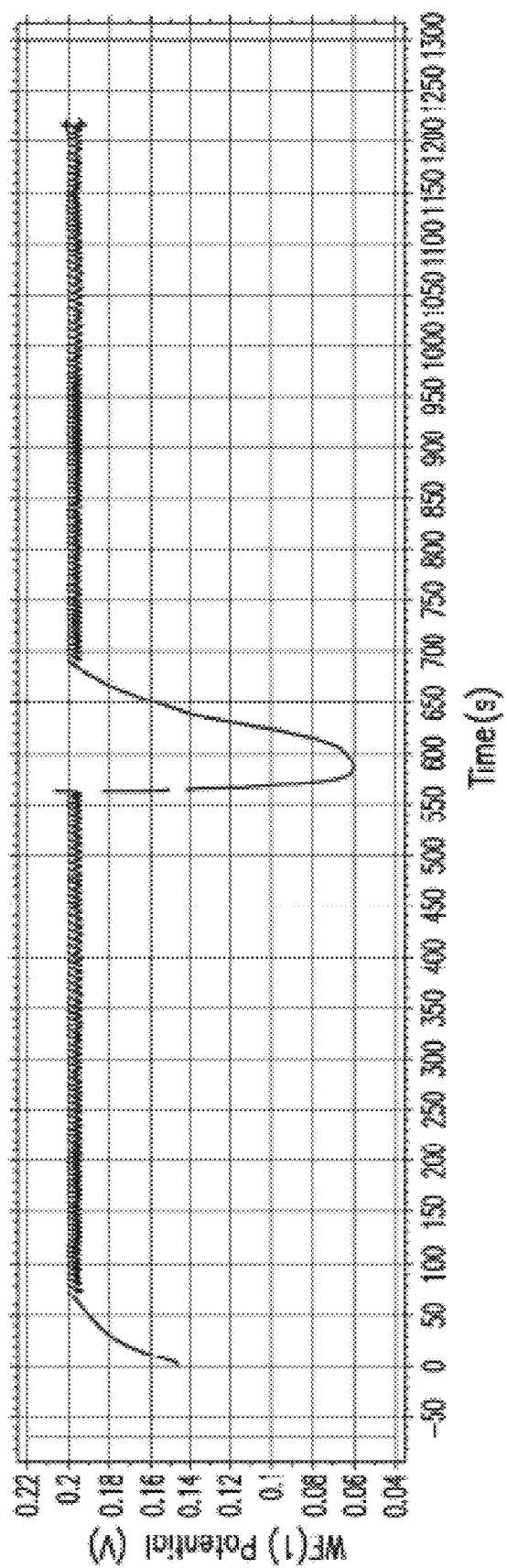
FIG. 30: shows experimental results of a closed look feedback method for controlling the pH of the solution as represented by the open circuit potential voltage measured by the sense electrode (SE) by applying a potential to the working electrode (WE), according to an example embodiment of the present invention.

Further, FIG. 30 shows experimental results of the open circuit potential voltage measured on a sense electrode adjacent to a working electrode with applied current. The working electrode is in a closed loop feedback with the sense electrode. The open circuit potential (OCP) of the working electrode as detected by the sense electrode is analogous to the pH of the solution near the working electrode. The feedback has been set to apply current to the WE only when the sense electrode open circuit potential is below 0.2V. The feedback is then bound between 0.19V and 0.2V (target OCP), switching the potential on the working electrode ON below 0.19 and OFF above 0.2V. The shift at time 560 s is a disruption caused by pipetting the bulk solution into the working electrode. This perturbs the pH gradient that was generated by the current applied to the working electrode causing the pH of the solution to immediately return to the pH of the bulk solution. After pipetting is stopped, the closed loop feedback system is able to restore and then maintain the target OCP.

FIGS. 32-47 show schematics for a closed loop feedback setup, where the OCP between the sense electrode (SE) 816 and reference electrode (RE) 822 is provided as input to a controller 900 that regulates the current source(s) 800-801 or potential source(s) 804-805 through one or more switches 802-803, 806-810. In this way, the system can be triggered on and off to increase or decrease the electrochemical generation/consumption of H$^+$ ions to balance the increase or decrease with the rate of diffusion of buffering ions from bulk solution to achieve a specific pH value as defined by a target OCP (V$_{TARGET}$) between the SE 816 and RE 822.

Example 20—Use of a pH Sensitive Coating

Figure 28:
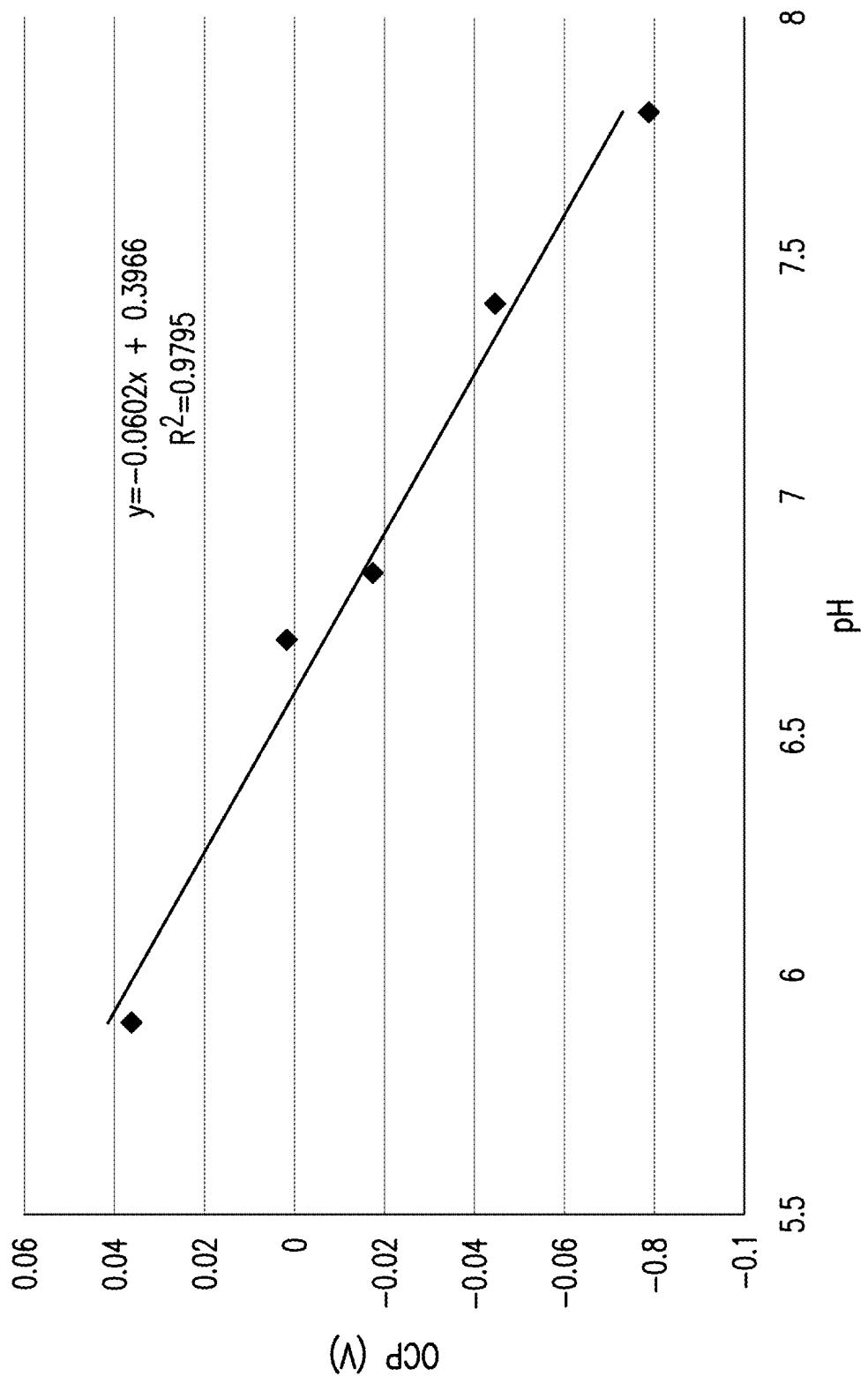
FIG. 28: illustrates a response of the open circuit potential for a PANI coated surface as a function of pH, where the 60 mV/pH is close to the Nernstian limit, according to an example embodiment of the present invention.

To further improve the closed loop pH control method, improved pH sensitivity can be incorporated by the addition of a pH sensitive coating 840 on the working and/or sense electrode 815, 816, 817. An example of such a coating is PANI, which has been shown to have exceptional pH sensitivity. PANI contains charged groups that interact with the hydrogen ions and change the conductivity of the polymer. The response of PANI as a function of pH is close to the Nernstian limit of pH detection (59 mV/pH). The change in open circuit potential of PANI is highly selective for H$^+$ ions, unlike just a bare electrode surface that is sensitive to other ions in solution other than just H+. FIG. 28 shows a response of the open circuit potential (OCP) as a function of pH where the surface of the electrode is coated with a pH sensitive PANI coating. The response of the OCP as a function of pH is shown by the slope of the line to be approximately 60 mV/pH which is close to the Nernstian limit.

Example 21—Device Designs

FIG. 31 shows example schematics of device designs utilizing the open loop method. In part A, a controlled current source is used while in part B a controlled voltage source is used.

Figure 40:
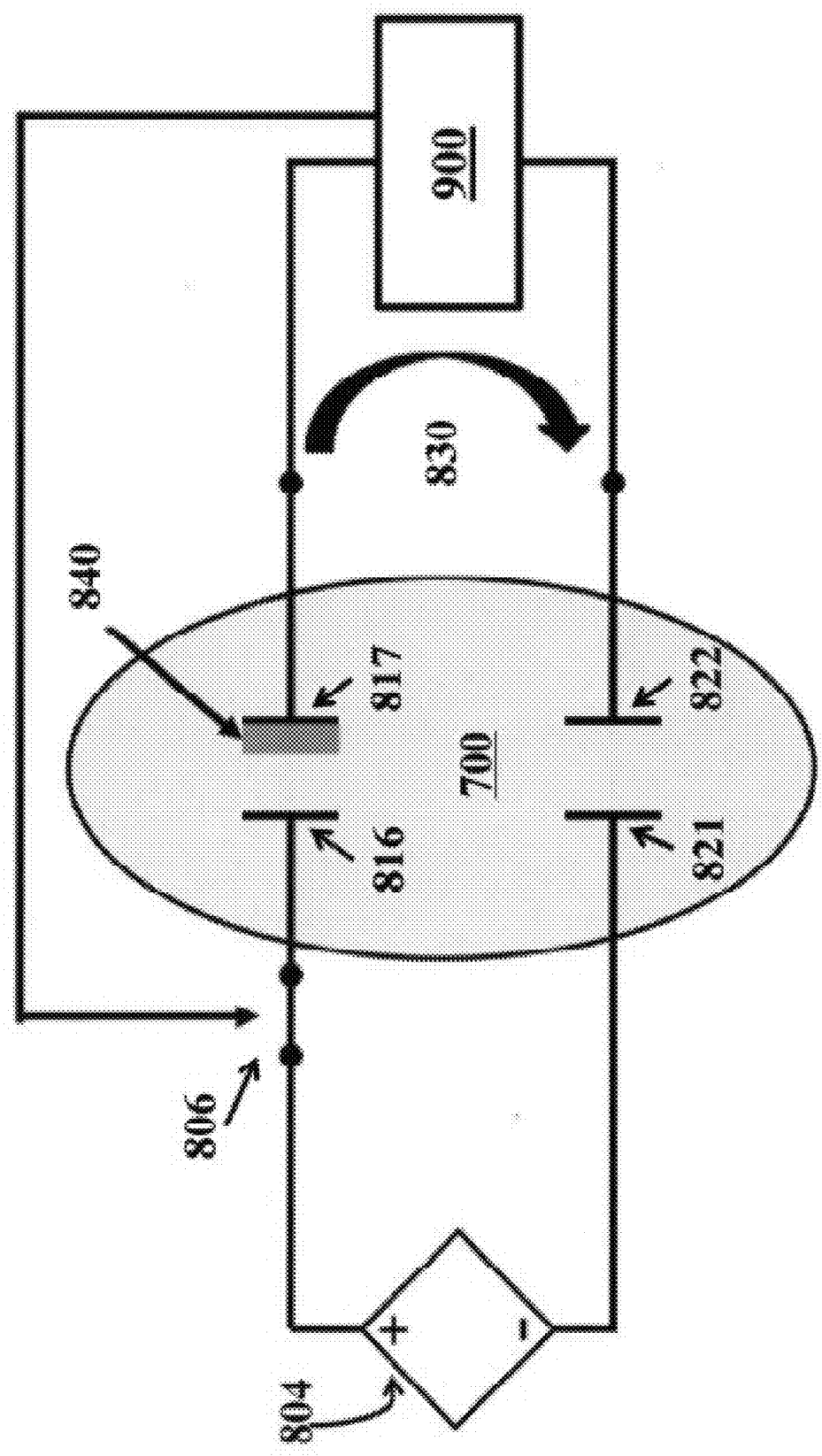
FIG. 40: illustrates a closed loop single controlled potential source with a PANI coated sense electrode, according to an example embodiment of the present invention.
Figure 41:
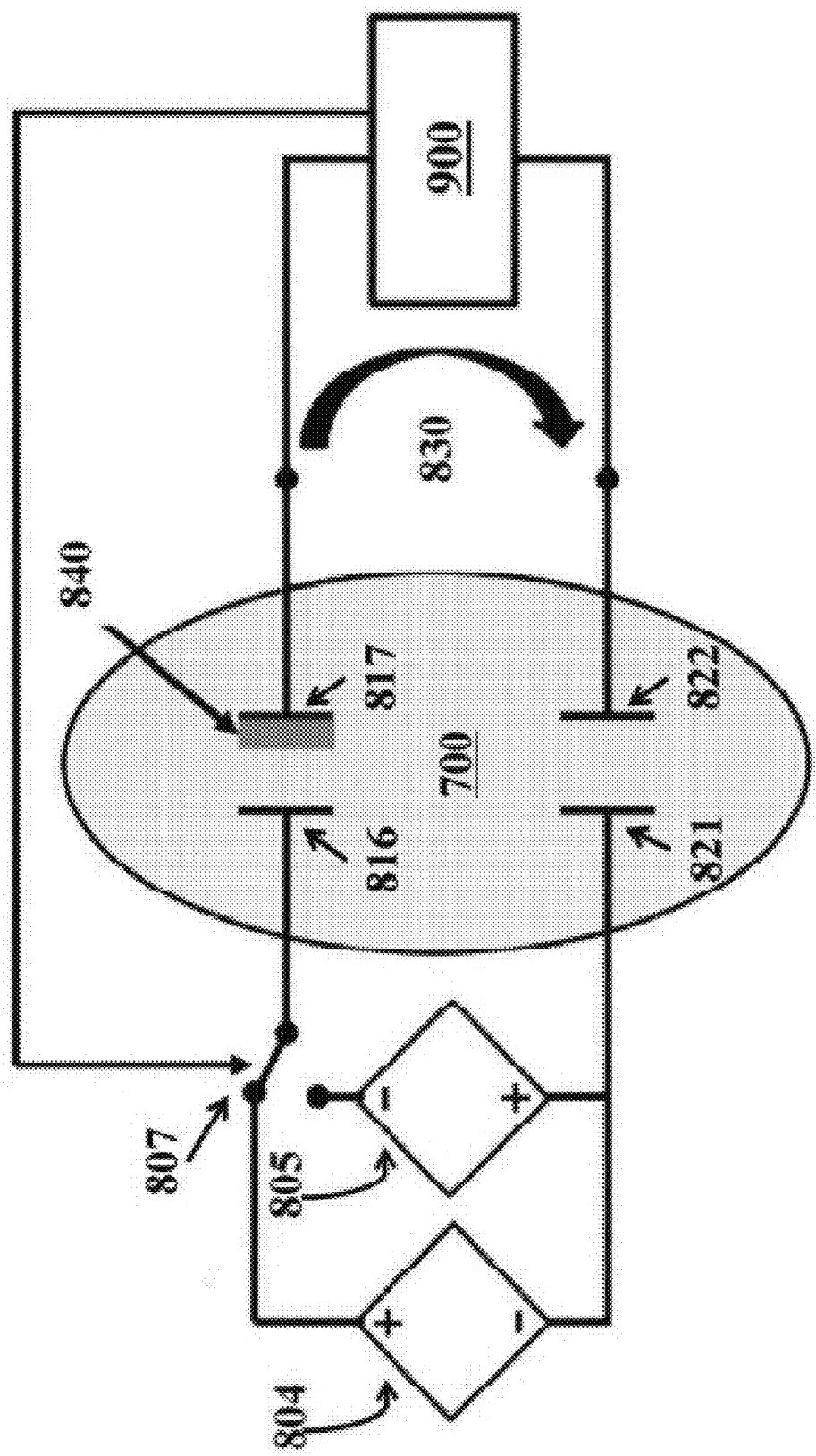
FIG. 41: illustrates a closed loop dual controlled potential source with a PANI coated sense electrode, according to an example embodiment of the present invention.
Figure 42:
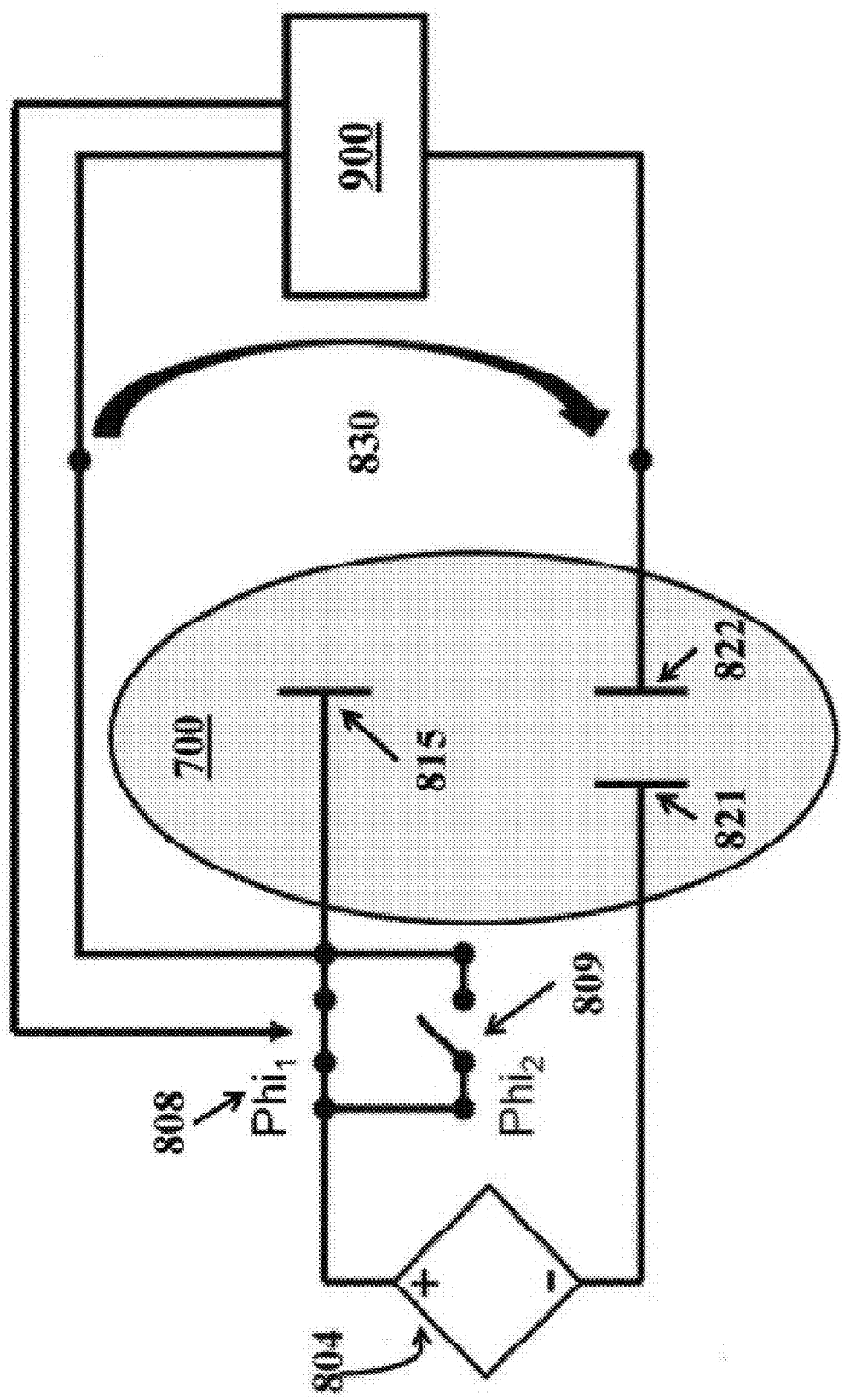
FIG. 42: illustrates a closed loop single controlled potential source with a combined working and sense electrode, where feedback controlled Phi1 and Phi2 switches are for WE potential input and SE measurement output, according to an example embodiment of the present invention.
Figure 43:
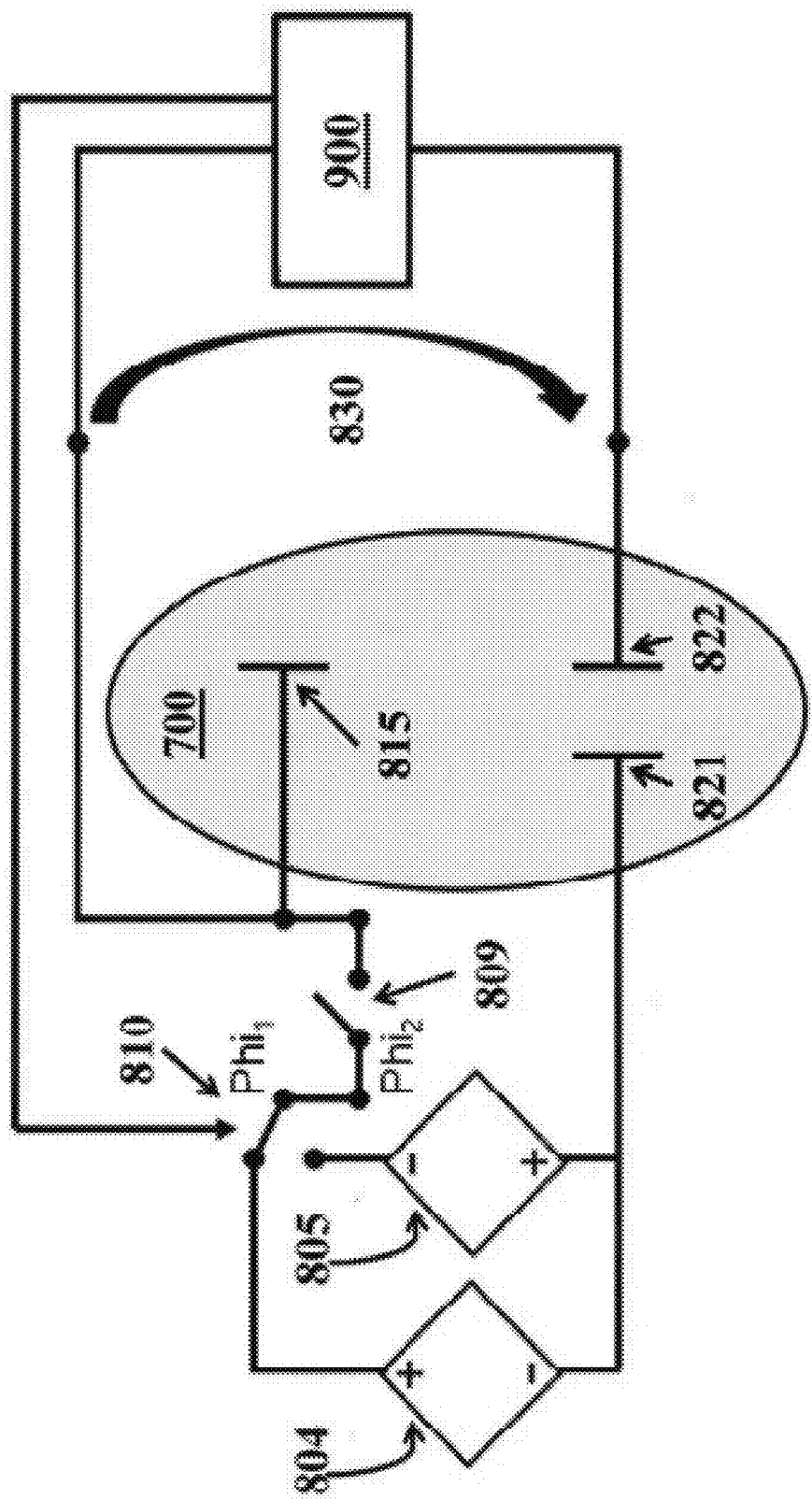
FIG. 43: illustrates a closed loop dual controlled potential source with a combined working and sense electrode, where feedback controlled Phi1 and Phi2 switches are for WE potential input and SE measurement output, according to an example embodiment of the present invention.
Figure 44:
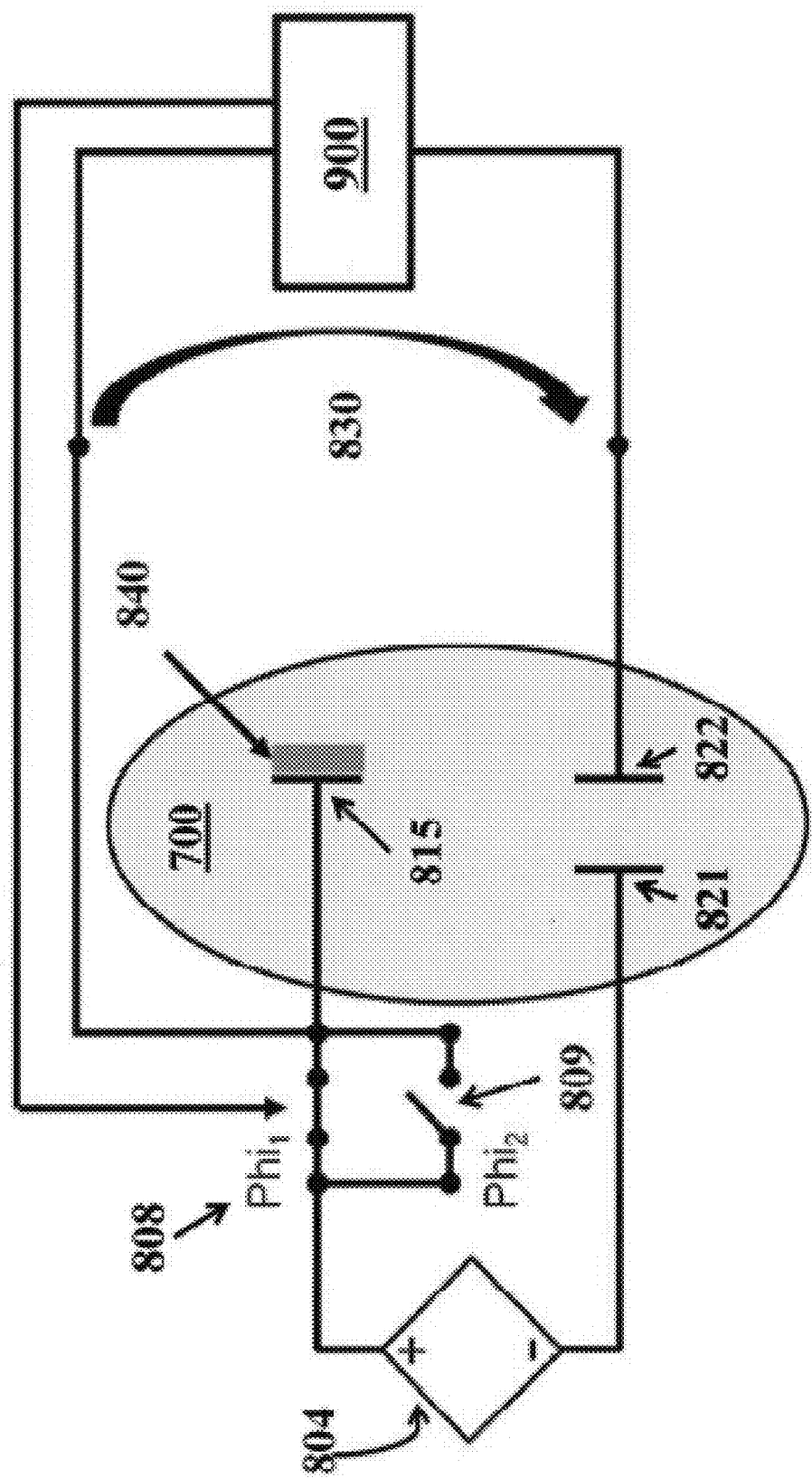
FIG. 44: illustrates a closed loop single controlled potential source with a combined working and sense electrode with PANI coating, where feedback controlled Phi1 and Phi2 switches are for WE potential input and SE measurement output, according to an example embodiment of the present invention.
Figure 45:
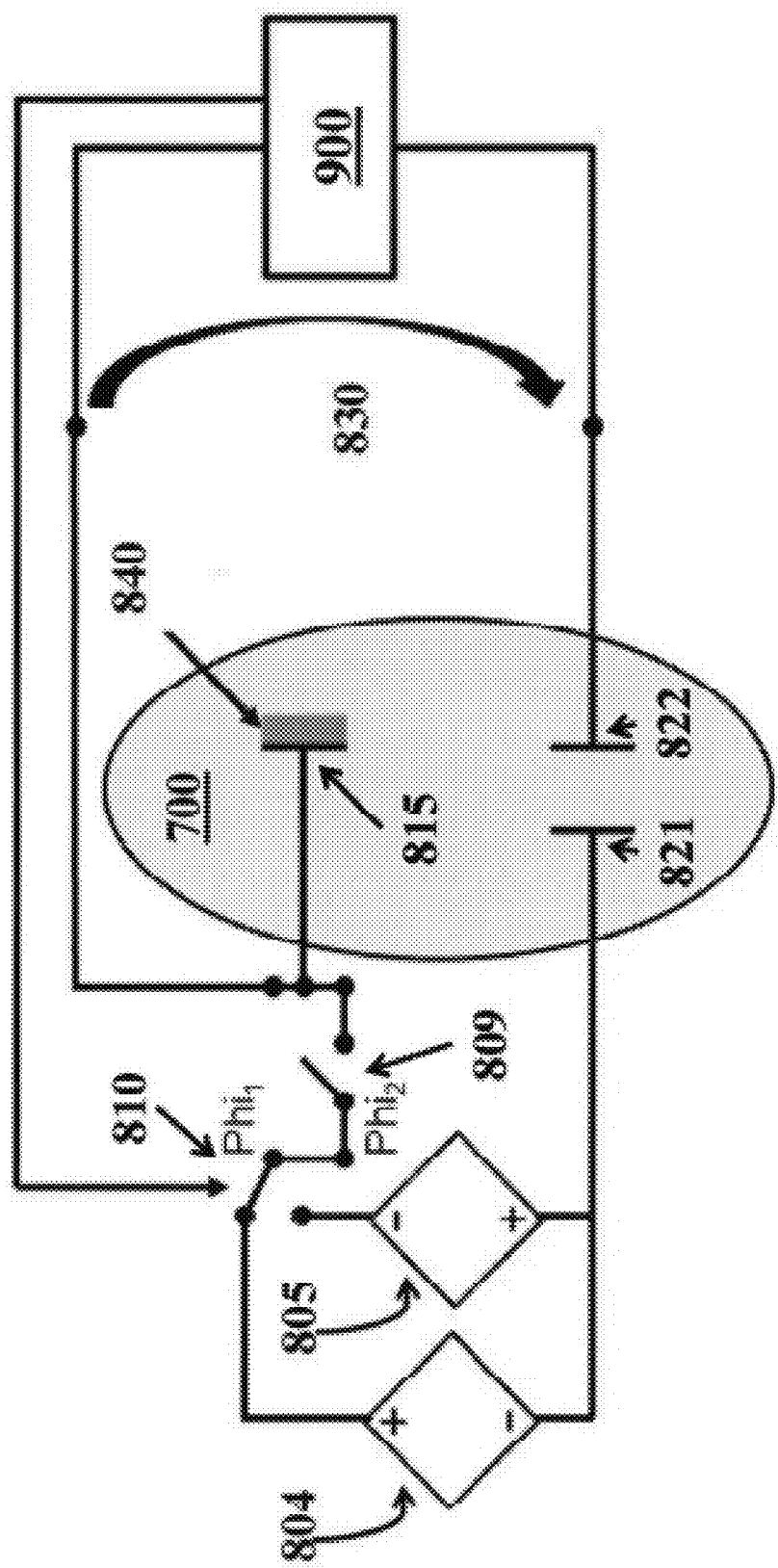
FIG. 45: illustrates a closed loop dual controlled potential source with a combined working and sense electrode with PANI coating, where feedback controlled Phi1 and Phi2 switches are for WE potential input and SE measurement output, according to an example embodiment of the present invention.

Various designs can be used in conjunction with the closed loop method. FIGS. 32, 34, 36, 38, 40, 42, and 44 show various designs for the closed loop method with a single controlled current source 800, and FIGS. 33, 35, 37, 39, 41, 43, and 45-47 show alternative designs using a dual controlled current source 800, 801. The closed loop method can also be implemented on designs with a PANI coated 840 sense electrode 817 (FIGS. 34, 35, 38-41, and 44-47). The WE and SE may also be combined into a single electrode 815 that is able to function as both the sense and working electrodes (FIGS. 36-39). Various switches 802-803, 806-810 are used to connect and disconnect the current 800-801 and voltage sources 804-805. FIGS. 32, 34, 36, and 38 shows a simple switch 802 for connecting and disconnecting the current source 800. FIG. 40 shows a similar switch 806 for connecting and disconnecting the voltage source 804. FIGS. 33, 44, 46, and 48 shows a changeover switch 803 for switching between the positive current source 800 and negative current source 801. FIG. 42 shows a similar changeover switch for switching between positive voltage source 804 and negative voltage source 805. In FIGS. 42-45, switches 808-810 operate in conjunction with clock phases Phi1 and Phi2. Switches 808 and 810 operate in conjunction with clock phase Phi1 and switch 809 in conjunction with Phi2. In each of the above examples the various switches which are controlled by the controller 900 based on feedback to allow for additional levels of control over the WE potential input and SE measurement output.

Figure 46:
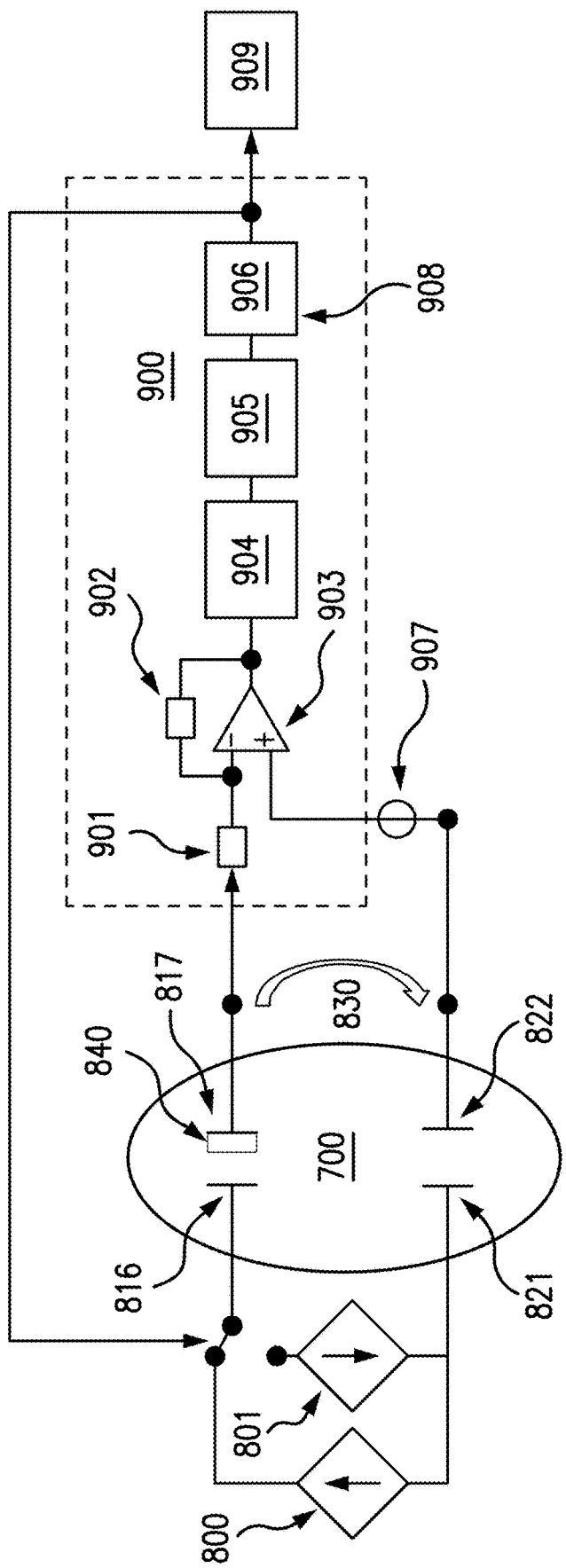
FIG. 46: illustrates a closed loop dual controlled current source with separate working and sense electrode with PANI coating and an analog controller architecture, according to an example embodiment of the present invention.

FIG. 46 schematically shows the system architecture with a closed loop controller. This system controls the pH with only one target value V$_{TARGET}$ 907. The same architecture can be applied to electrochemical cells with systems which use electric voltages instead of electric currents to modulate pH. In an example embodiment, the controller works as follows. The input voltage (V$_{in}$) 830 is sampled 901 and compared 902 to a target voltage V$_{TARGET}$ 907 and the difference is amplified 903 and processed by a loop filter 904. This could also be part of the loop filter and also be realized in different ways, e.g., as a switched capacitor amplifiers or a switched-capacitor loop filter. One example for a loop filter 904 is a PID-controller with a proportional part (P), an integrating part (I) and a differentiating part (D). The output signal of the loop filter 904 is compared with a fixed threshold by a comparator 905. The output of the comparator 905 can be positive or negative. This is equivalent to a digital representation. This digital signal is then stored in a clocked module 906 like a flip-flop or a latch. In an example embodiment, the frequency of the clock 908 is much higher than the frequency which is determined by the inverse of the diffusion time constant of $H^+$ ions. The output signal of the flip-flop then determines if a positive or negative unity current is applied to the WE 816. This scheme can also be applied to a system with only one current source 800 or to a system with voltage sources 804, 805 instead of current sources 800, 801. The system works as an "electrochemical delta-sigma-modulator," where the quantization error of the unity current sources is "shaped" by the transfer functions of the electrochemical cell and the transfer function of the electronic loop filter 904 and is distributed over a wide frequency spectrum determined by the frequency of the clock CLK 908. The one-bit-output of the comparator can be filtered by a digital filter 909, as shown in FIG. 46. This results in a digital representation of what the system has to apply to electrochemical cell in order to keep the pH at the target value.

Figure 47:
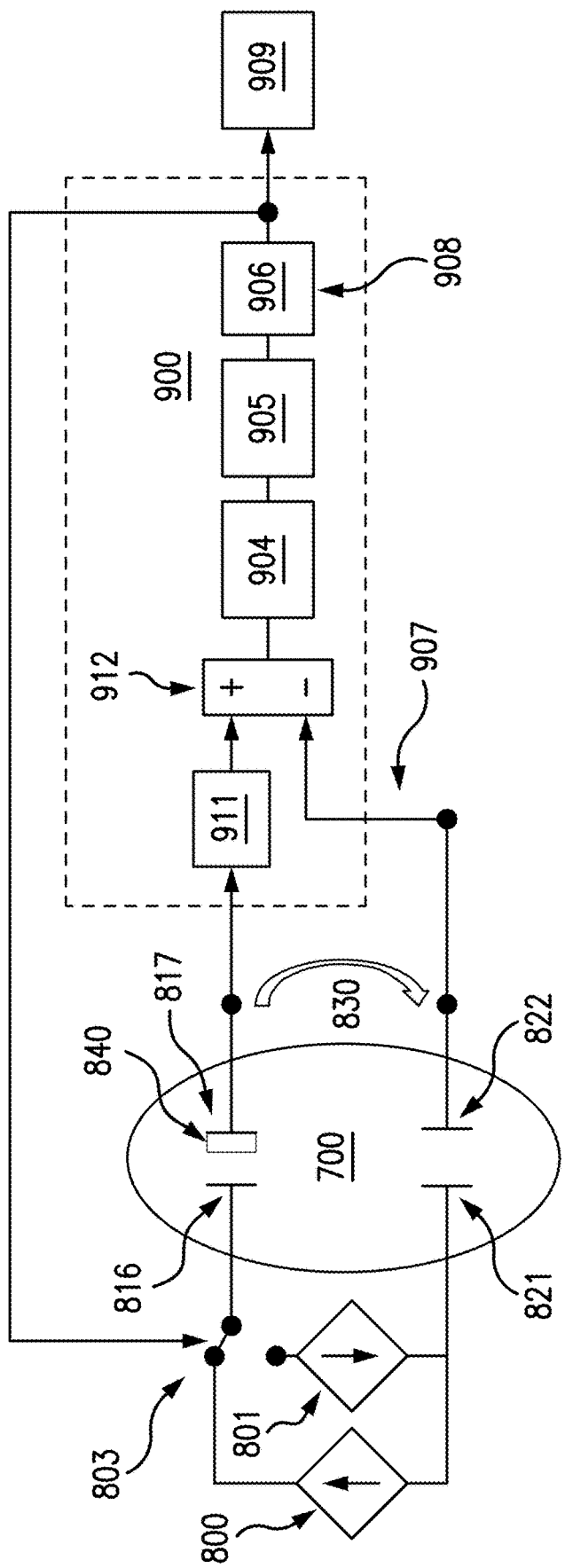
FIG. 47: illustrates a closed loop dual controlled current source with separate working and sense electrode with PANI coating and a digital controller architecture, according to an example embodiment of the present invention. Also shown is a controller architecture design with, in part A, analog signal processing for closed loop feedback control, and, in part B, digital signal processing for closed loop feedback control, the architecture being applicable to the controller schematics designated in FIGS. 32-45, according to an example embodiment of the present invention.
Figure 48:
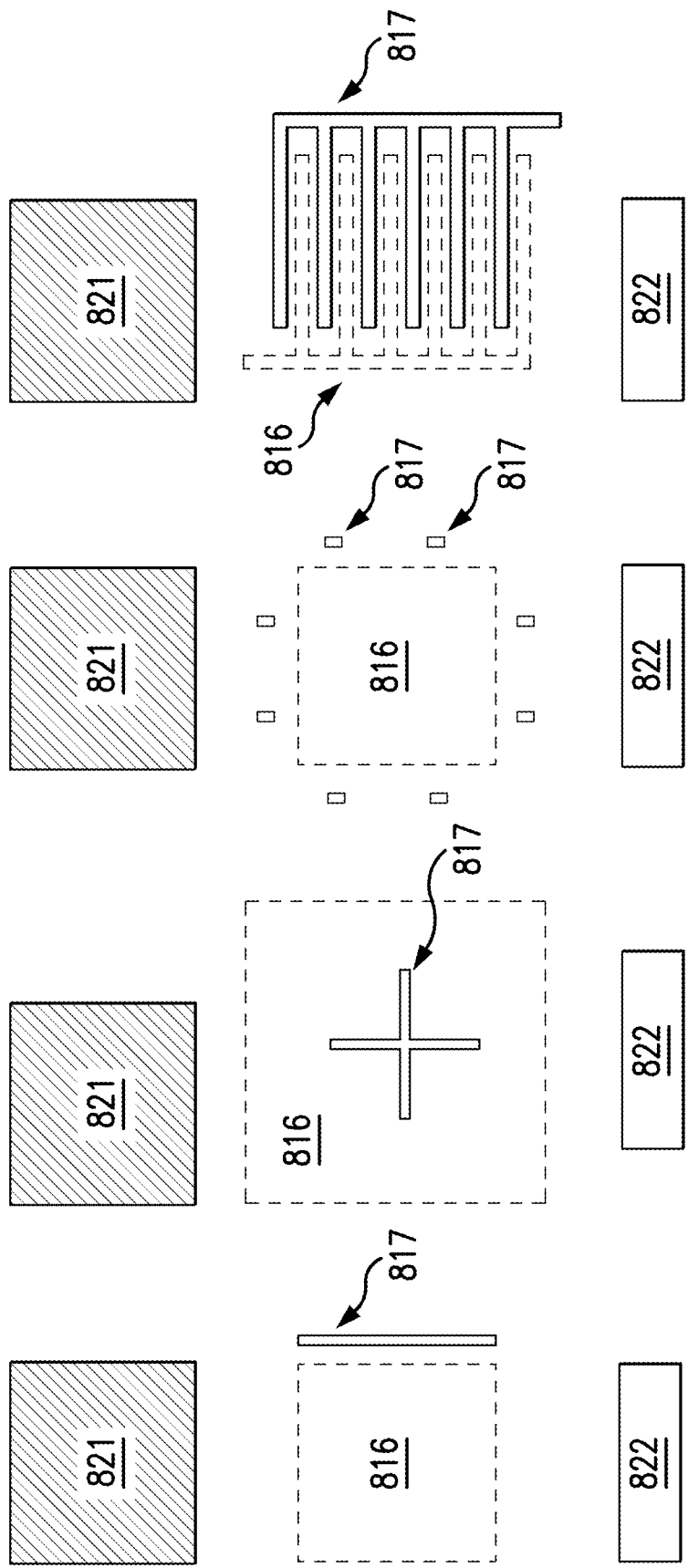
FIGS. 48A-48D: illustrate potential electrode configurations (routing not shown) for pH sensing, according to example embodiments of the present invention.

There is flexibility in the controller architecture design in that an analog controller, a digital controller, or a controller using both analog and digital signal processing can be used. FIG. 47 shows a second controller architecture where the main difference from that of FIG. 46 being the way how the target value for pH is set. In FIG. 46, the target pH value is set by an analog voltage $V_{TARGET}$ 907. This $V_{TARGET}$ 907 could be generated by a digital-to-analog converter (DAC). In FIG. 47, the input voltage $V_{in}$ 830 is digitized by an analog-to-digital converter (ADC) 911 and then compared 912 with a digital target value 910. As noted above, the electronics is clocked at a frequency 908 much higher than the inverse of the diffusion time constant of the $H^+$ ions.

The controllers in FIG. 47 can also be used to "measure" using the closed loop method the electric current or voltage that is needed to set a certain target pH value. This information can be used to characterize the system and derive stimuli for an open loop system. One example where this might be very useful is an array-structure of many sites where one site is used to "measure" the correct values using the closed loop, and those values are then applied according to the open-loop to many other "mirrored" sites.

FIGS. 48A-48D show an illustration of example electrode configurations (routing not shown) for pH sensing. An illustration of the geometry of the working electrode and sense electrode includes: FIG. 48A sense electrode located adjacent to the working electrode, FIG. 48B sense electrodes located within the working electrode, FIG. 48C multiple sense electrodes for a single working electrode, and FIG. 48D interdigitated working and sense electrodes. The incorporation of the PANI surface is advantageous for improving the accuracy of closed loop pH control. There are many different methods to incorporate a sense electrode for monitoring pH. For example, in still another alternative, the working electrode and sense electrode can also be one and the same by switching between active and passive/measuring steps.

Example 22—pH Modulation

Figure 53:
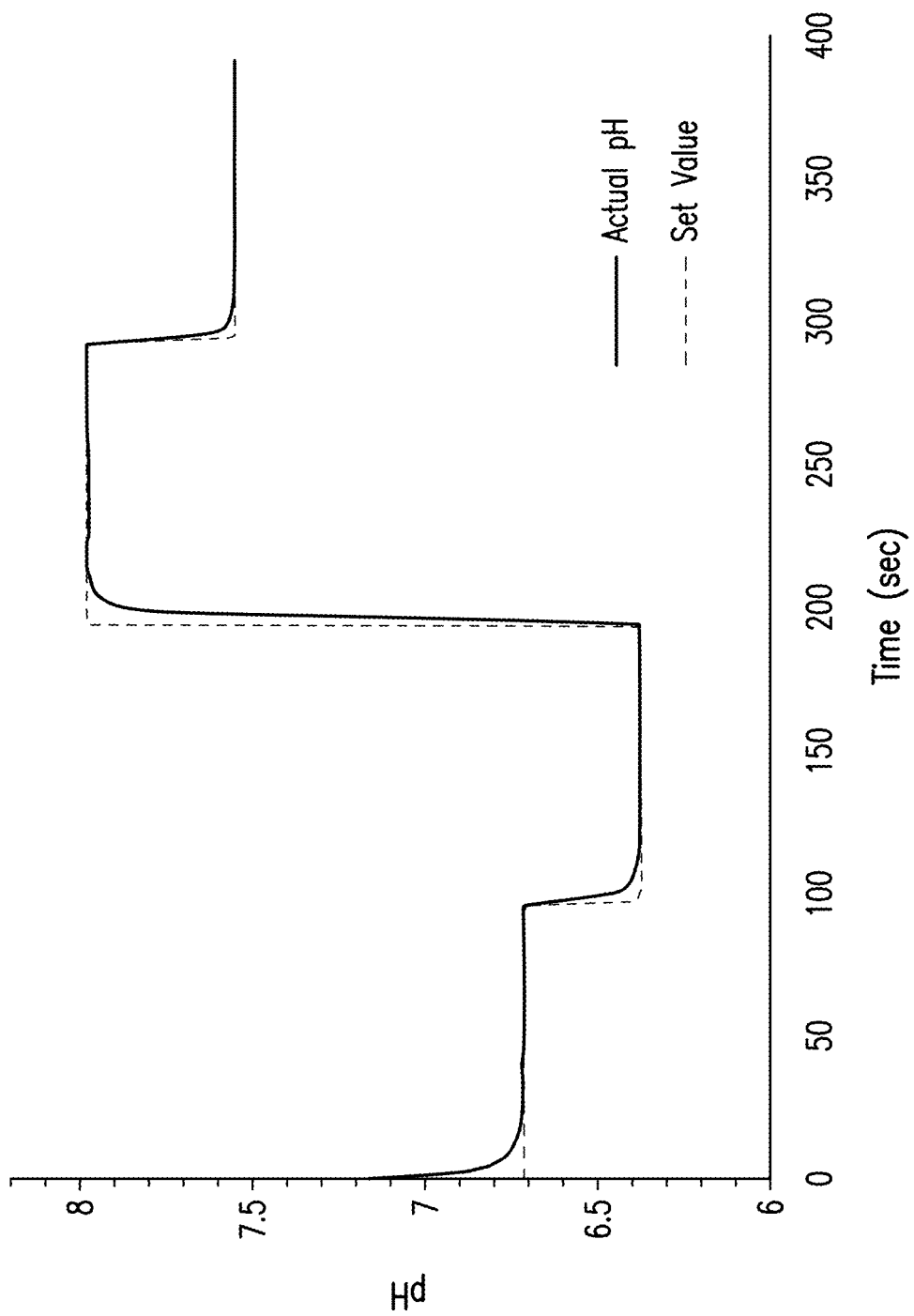
FIG. 53: illustrates an example of changing pH of a solution via oxidation/reduction of quinones in 1 mM phosphate buffer on an indium tin oxide electrode, according to an example embodiment of the present invention. The pH values were determined by a pre-calibrated iridium oxide sensing electrode patterned on a surface. The closed-loop control achieved the target pH values in an accurate and rapid manner.

Reversible electrochemical oxidation/reduction of pH modulation reagents such as quinone derivatives, hydrazine derivatives, or water have been demonstrated for a rapid pH change in a local region (Fomina et al., Lab Chip 16, pp. 2236-2244 (2016)). The pH modulation limit can depend on the pKa and oxidation/reduction potential of the specific pH modulation reagents, and their concentration. On-demand pH modulation by the oxidation of 2,5-dimethyl-1,4-hydroquinone and the reduction of the 2,5-dimethyl-1,4-benzoquinone on an indium-tin oxide electrode in 1 mM phosphate buffer was tested. FIG. 53 shows that when anodic current is applied to the electrode, the proton production overcomes the buffer capacity and pH of the solution becomes more acidic and vice versa.

Example 23—Multi-Electrode Array Designs

Figure 49:
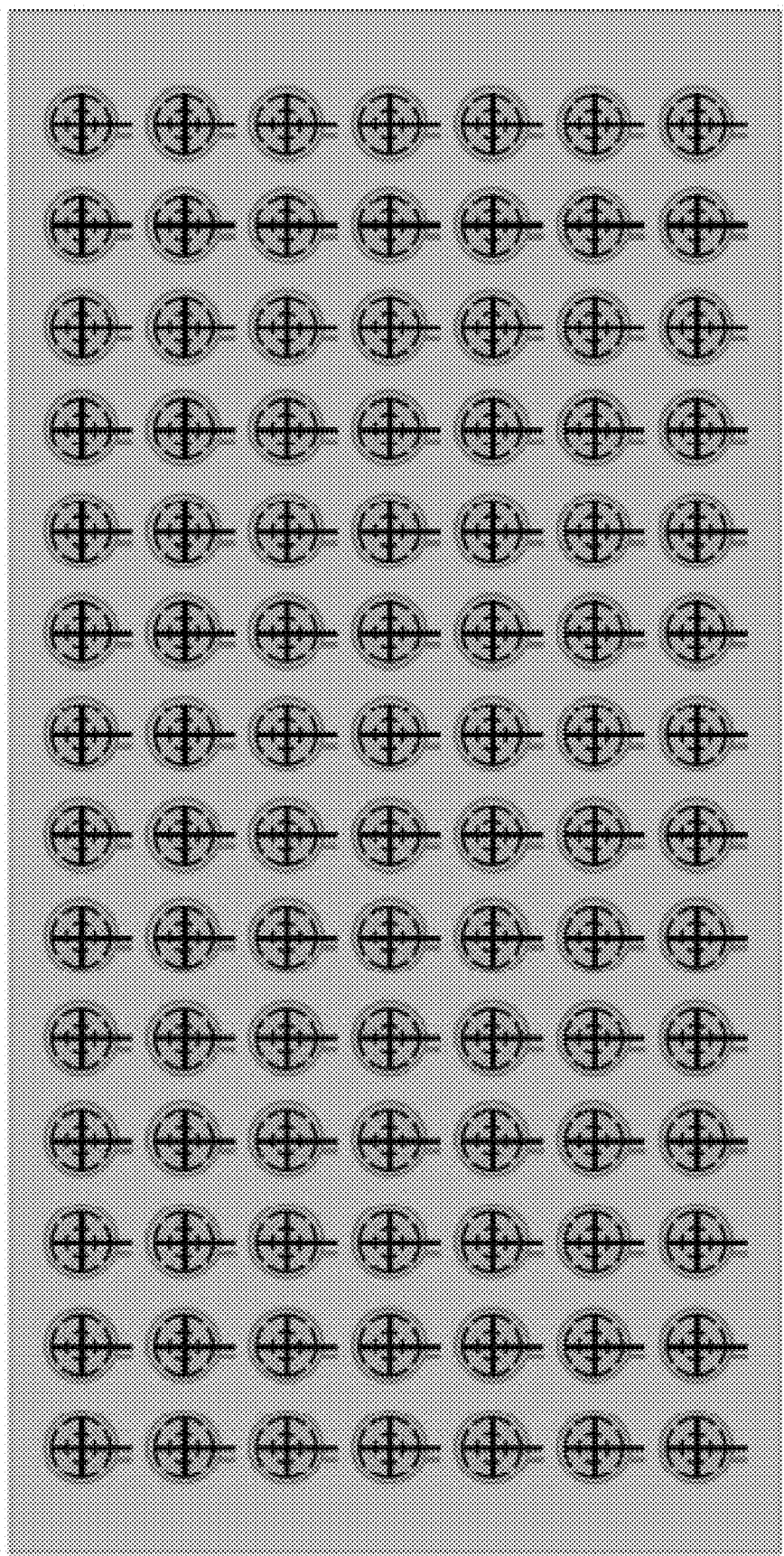
FIG. 49: illustrates a multi-electrode array with a feedback-controlling option, according to an example embodiment of the present invention, where each electrode set with a working, a sensing, a reference, and a counter electrode can be controlled independently for a distinctive target pH value and a temporal control scheme, and where a reference electrode and a counter electrode can be shared by multiple electrode sets.

FIG. 49 shows a non-limiting illustration of a multi-electrode array containing feedback-controlling electrodes. The connecting electrodes and contact pads that can be needed in some instances for the connection to a control unit are not shown for simplicity. This scheme is useful especially for carrying out multiple rounds of steps of reactions or visualization. Each feedback-controlling set in the feedback-controlling section can target independent pH values, the same pH value, or a combination thereof.

Figure 50:
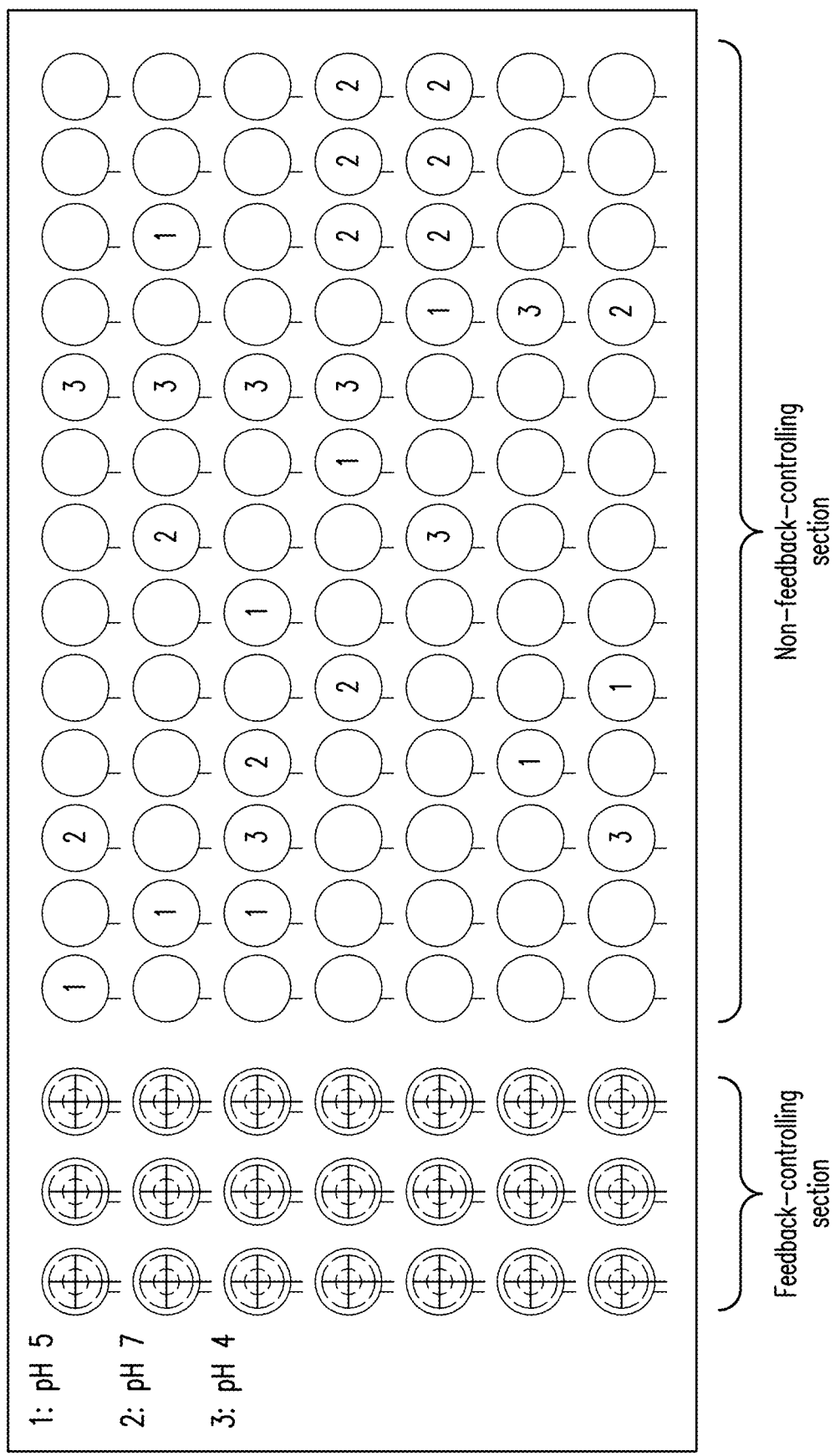
FIG. 50: illustrates a multi-electrode array with both a feedback-controlling section and a non-feedback-controlling section, according to an example embodiment of the present invention. The feedback-controlling section contains one or more feedback-controlling electrode sets that are composed of a working electrode, a reference electrode, a counter electrode, and a sensing element. A reference electrode and a counter electrode can be shared by multiple electrode sets. Each feedback-controlling set can target independent pH values, the same pH value, or a combination thereof. For each targeted pH value, there are one or more non-feedback-controlling electrode sets in the non-feedback-controlling section that are also assigned to the same target pH value. When the shape and size of the working electrode of the non-feedback-controlling electrode set(s) is similar to the shape and size of the working electrode of the feedback-controlling electrode set(s), electrical parameters obtained from the feedback-controlling section can be directly applied to the working electrodes in the non-feedback-controlling section. This configuration helps to attain the same level of control with a simpler device architecture.

FIG. 50 shows a non-limiting illustration of a controlling scheme for a single device containing a feedback-controlling section and a non-feedback-controlling section. This scheme is useful especially for carrying out multiple rounds of steps of reactions or visualization. Each feedback-controlling set in the feedback-controlling section can target independent pH values, the same pH value, or a combination thereof. For each targeted pH value, there can be one or more non-feedback-controlling electrode sets in the non-feedback-controlling section that are assigned to the same target pH value. When the shape and size of the working electrode of the non-feedback-controlling electrode set(s) is similar to the shape and size of the working electrode of the feedback-controlling electrode set(s), electrical parameters obtained from the feedback-controlling section can be directly applied to the working electrodes in the non-feedback-controlling section.

Figure 51:
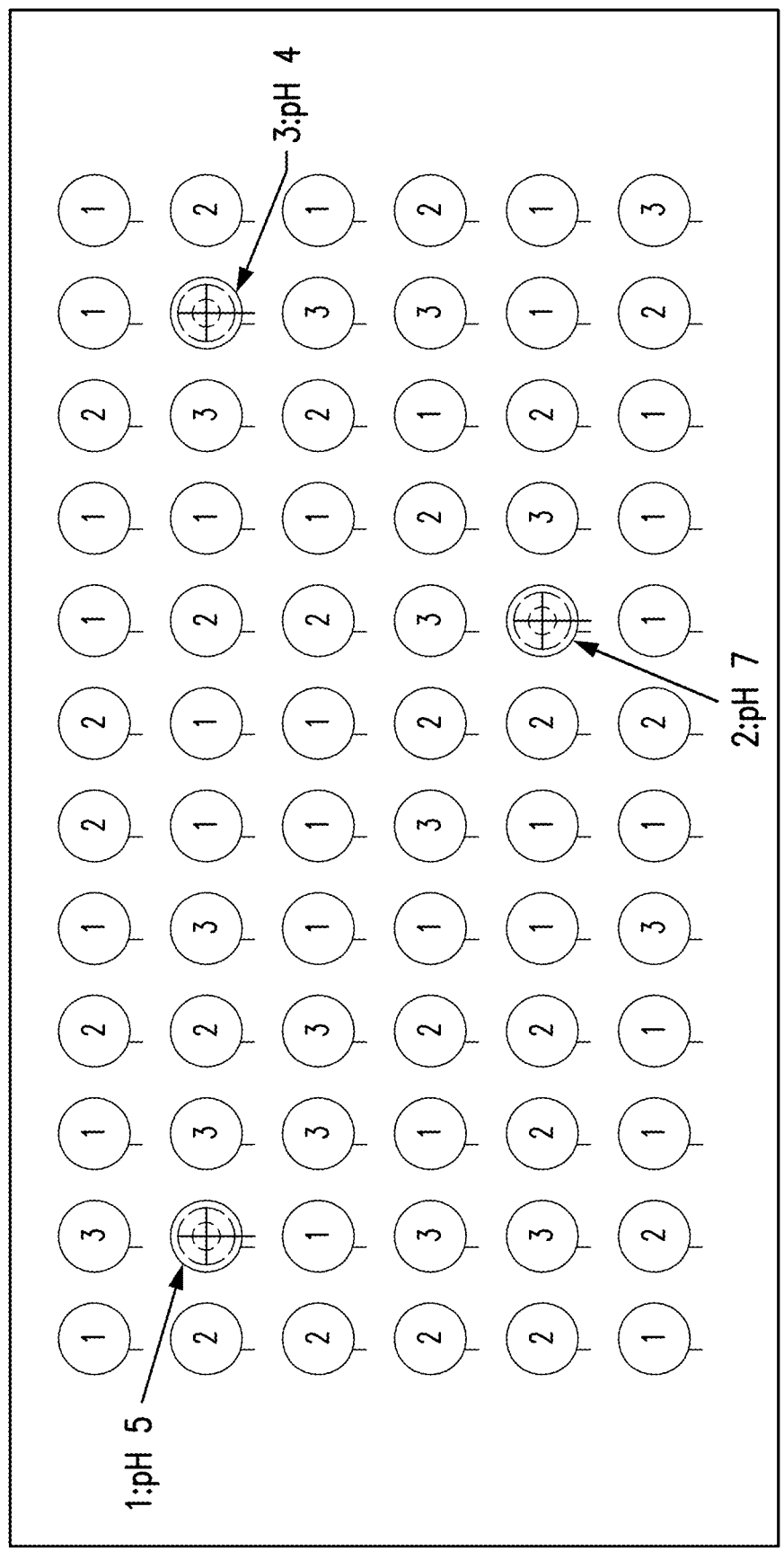
FIG. 51: illustrates a multi-electrode array with the feedback-controlling electrode sets distributed throughout the substrate and dispersed among non-feedback-controlling electrode sets. The feedback-controlling electrode sets can be distributed in a pattern and/or distributed randomly among non-feedback-controlling electrode sets. The feedback-controlling electrode set is composed of a working electrode, a reference electrode, a counter electrode, and a sensing element. A reference electrode and a counter electrode can be shared by multiple electrode sets. Each feedback-controlling electrode set can target independent pH values, the same pH value, or a combination thereof. For each targeted pH value, there are one or more non-feedback-controlling electrode sets that are also assigned to the same target pH value (pH coupled). This configuration helps to attain the same level of control or greater with a simpler device architecture. In some instances this configuration can minimize the effect on a sensing electrode from adjacent working electrodes that have different target pH values, such as when the feedback-controlling electrode set is surrounded by its respective pH coupled non-feedback-controlling electrode sets.

FIG. 51 shows a non-limiting illustration of feedback-controlling electrode sets dispersed among non-feedback-controlling electrode sets. Each feedback-controlling electrode set can target independent pH values, the same pH value, or a combination thereof. For each targeted pH value, there are one or more non-feedback-controlling electrode sets that are also assigned to the same target pH value (pH coupled). This configuration can help to attain the same level of control or a greater level of control with a more simple device architecture. In some instances this configuration can minimize the effect on a sensing electrode from adjacent working electrodes that have different target pH values, such as when the feedback-controlling electrode set is surrounded by its respective pH coupled non-feedback-controlling electrode sets. The non-feedback-controlling electrode sets that are assigned to the same target pH value of feedback-controlling electrode sets can be located adjacent to and/or not adjacent to the respective feedback-controlling electrode sets assigned the same target pH value. The feedback-controlling electrode sets can be distributed in a pattern and/or distributed randomly in regard to the respective non-feedback-controlling electrode sets assigned the same target pH value. In some instances, the feedback-controlling electrode sets are distributed randomly or in a pattern designed to provide a uniform solution pH across the working electrodes. In some instances, the feedback-controlling electrode sets are distributed in a pattern designed to provide maximum versatility in providing unique solution pH and/or unique series of pH changes at each working electrode. In some instances, the feedback-controlling electrode sets are distributed in a pattern designed to provide maximum feedback or to minimize feedback from the aggregate of sensing elements.

As further detailed in the following paragraphs, in non-limiting examples, the multi-electrode array designs contain pH coupled electrode sets that are pH coupled through direct electrical coupling between the working electrodes of the pH coupled electrode sets; in other non-limiting examples, the multi-electrode array designs contain pH coupled electrode sets that are pH coupled through each working electrode of the pH coupled electrode sets receiving the same electrical parameters from a processor; and in other non-limiting examples, the multi-electrode array designs contain pH coupled electrode sets that are pH coupled through each working electrode of the pH coupled electrode sets receiving different electrical parameters from a processor yet configured to produce the same target pH value.

Direct electrical coupling can be electrical coupling that bypasses or does not include a processor in the direct electrical coupling path. In some instances, direct electrical coupling is achieved through coupling through an electrical wire. When the working electrodes of the pH coupled electrode sets are directly electrically coupled, in some instances, the feedback-controlling working electrode obtains electrical parameters from a processor and the feedback-controlling electrode passes the electrical parameters directly to the non-feedback-controlling working electrode through the direct electrical coupling. Preferably the shape and size of the working electrode of the non-feedback-controlling electrode set(s) are similar to the shape and size of the working electrode of the feedback-controlling electrode set(s). In this manner, the working electrodes of the pH coupled electrode sets can receive the same electrical parameters and modify the solution surrounding the working electrodes of the pH coupled electrode sets in the same manner.

When each working electrode of the pH coupled electrode sets receives the same electrical parameters from a processor, the working electrodes of the pH coupled electrode sets preferably have the same size and/or shape so that the working electrodes of the pH coupled electrode sets modify the solution surrounding the working electrodes of the pH coupled electrode sets in the same manner. In some instances, when the electrical parameters are received from a processor, reassignment of which non-feedback-controlling electrode set(s) are pH coupled to which feedback-controlling electrode set(s) can be readily changed.

When each working electrode of the pH coupled electrode sets receive electrical parameters from a processor to produce the same target pH value, the working electrodes of the pH coupled electrode sets can have different sizes and/or shapes from each other. In these instances, the processor can provide (1) electrical parameters to the working electrode(s) of the pH coupled feedback-controlling electrode set to modify the pH of the solution surrounding the working electrode(s) of the pH coupled feedback-controlling electrode set to a target pH value and (2) modified electrical parameters to the working electrode(s) of the pH coupled non-feedback-controlling electrode set that have a different size and/or shape to modify the pH of the solution surrounding the working electrode(s) of the pH coupled non-feedback-controlling electrode to the same target pH value. In some instances, the modified electrical parameters are modified according to predetermined calibration data that correlates electrical parameters required for the working electrode(s) of the pH coupled feedback-controlling electrode set and electrical parameters required for the working electrode(s) of the pH coupled non-feedback-controlling electrode set to both obtain the same target pH value. In some instances, when the electrical parameters are received from a processor, reassignment of which non-feedback-controlling electrode set(s) are pH coupled to which feedback-controlling electrode set(s) can be readily changed.

In some instances, the pH coupling can be changed over time during the same use or between uses of a device containing pH coupled electrode sets. This can be advantageous when a device containing these pH coupled electrodes is used to produce more than one product at the same time, such as a library of products, as the device would be capable of providing a unique series of pH conditions at each individual working electrode to produce a unique product at each working electrode. This can also be advantageous to reduce the number of sensing electrodes and accordingly the amount of feedback from the aggregate of sensing elements to be processed that would otherwise be required. This can further be advantageous when the same device containing the pH coupled electrode sets is used for multiple different purposes between uses. In some instances, changing the pH coupling is controlled through a network of switches and/or through the processor individually controlling each working electrode. In some instances, the pH coupling and/or changes in pH coupling is user defined, such as through selection of pH coupling through a graphical user interface.

Example 24—Closed-Loop Controls and Designs

FIG. 52 shows a non-limiting illustration of a schematic of how a closed-loop pH control can work with surface-patterned electrodes.

FIGS. 54A-54B show a non-limiting illustration of a closed-loop pH control with an external counter electrode and reference electrode FIG. 54A and a non-limiting example of a closed-loop pH control with a surface patterned on-chip counter and reference electrode FIG. 54B.

FIGS. 55A-54D show non-limiting illustration of designs of sensing elements and working electrodes and in some instances, other components. FIG. 55A and FIG. 55B show slide designs that can be used for various applications. In some instances, the sensing element needs physical separation from the working electrode to avoid a crosstalk or shorting. If the working electrode and the sensing element need to be on the same plane, a small gap ranging from 1 nm to 100 microns can be used in between the working electrode and the sensing element FIG. 55C. Another possible design option is to construct a multi-layer stack: a thin insulating layer can be placed in between the sensing element and the working electrode FIG. 55D. The counter electrode can also be patterned around the working electrode, which can minimize the diffusion effect and help control pH with a more definitive shape of the pH modulation zone, especially with non-buffered solution FIG. 55E.

What is claimed is:

1. A device for controlling pH of a solution on an array of electrodes, the device comprising:
   a support; and
   an array of electrodes comprising:
   one or more feedback-controlling electrode set(s) that each includes:
      one or more reference electrode(s);
      one or more counter electrode(s); and
      one or more subset(s) comprising a pH sensing element electrically coupled, directly or indirectly, to a working electrode;

wherein:
a reference electrode of the one or more reference electrode(s) and/or a counter electrode of the one or more counter electrode(s) is electrically coupled, directly or indirectly, with at least one of the one or more subset(s);
one or more non-feedback-controlling electrode set(s) that each does not comprise a pH sensing element and that each comprises:
one or more reference electrode(s) of the respective non-feedback-controlling electrode set(s);
one or more counter electrode(s) of the respective non-feedback-controlling electrode set(s); and
one or more working electrode(s) of the respective non-feedback-controlling electrode set(s);
for each of the non-feedback-controlling electrode set(s), each of the one or more reference electrode(s) of the respective non-feedback-controlling electrode set and/or each of the one or more of the counter electrode(s) of the respective non-feedback-controlling electrode set is electrically coupled, directly or indirectly, with at least one of the working electrode(s) of the respective non-feedback-controlling electrode set;
the device is configured to iteratively perform the following:
a) select a respective amount of current and/or voltage to be applied to at least one of the one or more working electrode(s) of the respective feedback-controlling electrode set(s) in order to minimize a difference between a signal output of the coupled pH sensing element(s) and a target sensing value;
b) apply the selected respective amount of current and/or voltage to the at least one of the one or more working electrode(s) of the respective feedback-controlling electrode set(s) to change pH of a solution close to the respective working electrode(s) of the respective feedback-controlling electrode set(s); and
c) measure the signal output of the coupled pH sensing element(s);
the electrical couplings are through solid electrically conductive material; and
at least one of the feedback-controlling electrode set(s) is (a) electrically coupled, directly or indirectly, to at least one of the non-feedback-controlling electrode set(s), and (b) is configured to apply the selected amount of current and/or voltage, which is applied to the one or more working electrode(s) of the at least one coupled feedback-controlling electrode set(s), also to one or more of the working electrode(s) of the respective coupled at least one non-feedback-controlling electrode set(s).

2. The device of claim 1, wherein one or more of the reference electrode(s) of the respective feedback-controlling electrode set(s) is also a pH sensing element.

3. The device of claim 1, wherein the solution contains one or more redox active species selected from the group consisting of: quinones, catechols, aminophenols, hydrazines, derivatives thereof, and combinations thereof.

4. The device of claim 1, wherein the device comprises or is communicatively coupled to a processor, and wherein selecting an amount of current and/or voltage to be applied comprises executing an algorithm using an input comprising the signal output of the pH sensing element(s).

5. The device of claim 1, wherein one or more of the working electrode(s) of the respective feedback-controlling electrode set(s), one or more of the reference electrode(s) of the respective feedback-controlling electrode set(s), one or more of the counter electrode(s) of the respective feedback-controlling electrode set(s), and/or one or more of the pH sensing element(s) is electrically coupled, directly or indirectly, to a switch-matrix module.

6. The device of claim 1, wherein one or more of the reference electrode(s) of the respective feedback-controlling electrode set(s) and/or one or more of the counter electrode(s) of the respective feedback-controlling electrode set(s) is electrically coupled, directly or indirectly, to two or more of the subsets.

7. The device of claim 1, wherein (i) all of the feedback-controlling electrode set(s) is comprised in one section of the device and all of the non-feedback-controlling electrode set(s) is arranged in a physically separate second section of the device, or (ii) one or more of the feedback-controlling electrode set(s) is interspersed between two or more of the non-feedback-controlling electrode set(s).

8. A method of controlling a pH of a solution using a device that comprises an array of one or more feedback-controlling electrode set(s), the feedback-controlling electrode set(s) comprising (1) one or more reference electrode(s), (2) one or more counter electrode(s), and (3) one or more subset(s), the one or more subset(s) each including a pH sensing element electrically coupled, directly or indirectly, to a working electrode, wherein a reference electrode of the one or more reference electrode(s) and/or a counter electrode of the one or more counter electrode(s) is electrically coupled, directly or indirectly, with one or more of the subset(s), wherein the device further comprises one or more non-feedback-controlling electrode set(s) electrically coupled, directly or indirectly, to one or more of the feedback-controlling electrode set(s), the one or more non-feedback-controlling electrode set(s) each comprising (1) one or more reference electrode(s) of the respective non-feedback-controlling electrode set(s), (2) one or more counter electrode(s), and (3) one or more working electrode(s), each of the one or more reference electrode(s) of the respective non-feedback-controlling electrode set(s) and/or each of the one or more of the counter electrode(s) of the respective non-feedback-controlling electrode set(s) being electrically coupled, directly or indirectly, with at least one of the one or more working electrode(s) of the respective non-feedback-controlling electrode set(s), and each of the one or more non-feedback-controlling electrode set(s) not comprising a pH sensing element, the method comprising:
a. selecting a target sensing value for a pH sensing element based on one or more signal(s) output from a pH sensing element in a solution with a target pH; and
b. iteratively performing the following:
i. selecting a respective amount of current and/or voltage to be applied to at least one of the working electrode(s) of the feedback-controlling electrode set(s) in order to minimize a difference between a signal output of the pH sensing element and the target sensing value;
ii. applying the selected respective amount of current and/or voltage to the at least one of the working electrode(s) of the feedback-controlling electrode set(s) to change pH of a solution close to the respective working electrode of the feedback-controlling electrode set(s); and
iii. measuring the signal output of the pH sensing element;

wherein:
the electrical couplings are through solid electrically conductive material; and
the applying of the selected respective amount of current and/or voltage includes applying the selected amount of current and/or voltage to one or more of the working electrode(s) of the coupled feedback-controlling electrode set and applying the same respective amount of current and/or voltage to one or more of the working electrode(s) of the coupled non-feedback-controlling electrode set(s) to change pH of a solution close to the working electrode(s) of the coupled non-feedback-controlling electrode set(s).

9. The method of claim 8, wherein the solution comprises water and/or one or more redox active specie(s), and wherein the applied current and/or voltage electrochemically generates and/or consumes hydrogen ions by an electrochemical reaction of the water and/or the one or more redox active specie(s).

10. The method of claim 9, wherein the one or more redox active species is selected from the group consisting of: quinones, catechols, aminophenols, hydrazines, derivatives thereof, and combinations thereof.

11. The method of claim 8, comprising determining pH of the solution by comparing the signal output of the pH sensing element to predetermined calibration data that correlates pH to values of a signal output of the pH sensing element.

12. The method of claim 8, wherein the used device comprises an array of two or more of the feedback-controlling electrode set(s).

13. The method of claim 12, wherein at least two of the feedback-controlling electrode set(s) are each controlled individually with independent target pH values and/or independent temporal programs for applying the selected amount of current and/or voltage.

14. The method of claim 8, wherein the feedback-controlling electrode set(s) is electrically coupled, directly or indirectly, to a switch-matrix module and control of each feedback-controlling electrode set(s) is performed by a switch-matrix module.

15. The method of claim 8, wherein at least one of the reference electrode(s) and/or at least one of the counter electrode(s) is electrically coupled, directly or indirectly, to two or more of the subsets.

16. The method of claim 8, wherein the used device comprises an array of two or more of the coupled feedback-controlling electrode set(s).

17. The method of claim 16, wherein at least two of the coupled feedback-controlling electrode set(s) are each controlled individually with independent target pH values and/or independent temporal programs for applying the selected amount of current and/or voltage to the respective one or more working electrode(s) of the coupled feedback-controlling electrode set(s) and the respective one or more working electrode(s) of the coupled non-feedback-controlling electrode set(s).

18. The method of claim 8, wherein the reference electrode and/or the counter electrode of the one or more feedback-controlling electrode set is electrically coupled, directly or indirectly, to subsets of two or more feedback-controlling electrode sets and/or to working electrodes of two or more non-feedback-controlling electrode sets.

19. The method of claim 8, wherein the one or more working electrode(s) of the coupled non-feedback-controlling electrode set(s) has a similar shape and design to the one or more working electrode(s) of the coupled feedback-controlling electrode.

20. The method of claim 8, wherein the respective amount of current and/or voltage selected is determined in part by the measured signal output of the coupled pH sensing element in a closed-loop configuration to change the pH of the solution close to the respective working electrode(s) at the same time as measuring the signal output of the coupled pH sensing element(s).

* * * * *